(12) United States Patent
Bombrun et al.

(10) Patent No.: US 7,696,231 B2
(45) Date of Patent: Apr. 13, 2010

(54) OXINDOLE HYDRAZIDE MODULATORS OF PROTEIN TYROSINE PHOSPHATASES (PTPS)

(75) Inventors: Agnes Bombrun, Monnetier-Mornex (FR); Patrick Gerber, Villars-sous-Yens (CH); Denis Church, Commugny (CH)

(73) Assignee: Laboratoires Serono SA, Coinsins (CH)

( * ) Notice: Subject to any disclaimer, the term of this patent is extended or adjusted under 35 U.S.C. 154(b) by 1110 days.

(21) Appl. No.: 10/493,066

(22) PCT Filed: Oct. 24, 2002

(86) PCT No.: PCT/EP02/11919

§ 371 (c)(1),
(2), (4) Date: Oct. 5, 2004

(87) PCT Pub. No.: WO03/037328

PCT Pub. Date: May 8, 2003

(65) Prior Publication Data

US 2005/0043388 A1 Feb. 24, 2005

(30) Foreign Application Priority Data

Oct. 30, 2001 (EP) .................................. 01125380

(51) Int. Cl.
*A61K 31/44* (2006.01)
*A61K 31/404* (2006.01)
*C07D 209/46* (2006.01)

(52) U.S. Cl. ........................ 514/339; 514/414; 514/418; 546/277.1; 548/472; 548/483

(58) Field of Classification Search ................. 514/223, 514/414, 418, 339; 546/201, 277.1; 548/483, 548/472
See application file for complete search history.

(56) References Cited

U.S. PATENT DOCUMENTS 6,642,381 B2* 11/2003 Guertin et al. .............. 544/184

OTHER PUBLICATIONS

Chemcats 2001:1606258 (2001).*
Buu-Hoi et al. "Tuberculostatic . . . " CA 48:42359 (1954).*
Gupta et al. "Synthesis of some . . . " CA 98:107110 (1983).*
Gupta et al. "Synthesis of some . . . " CA99:105082 (1983).*
Agarwal et al. "Synthesis of 1-dialkyl . . . " CA 100:156566 (1984).*
Varma et al. "Effect of some 5-chloro-. . . " CA102:75531 (1985)So.*
Somoza et al. "Rational design of novel . . . " CA129:22964 (1998).*
Zidovetzki et al. "Inhibition of plasmodium . . . " CA 122:52969 (1995).*
Berlin "The effect of quinidine . . . " CA 105:127028 (1986).*
Database Chemcats 'Online! Specs and BioSPECS product catalogue, Jul. 1, 2001, retrieved from STN, Database accession No. 2001:1606258, XP002228603.
Database Chemcats 'Online! ChemBridge Product List, Jan. 17, 2002, retrieved from STN, Database accession No. 2002:1383245, XP002228604.

Database Chemcats 'Online! ChemBridge Product List, Jan. 17, 2002, retrieved from STN, Database accession No. 2002:1383099, XP002228605.
A.I. El-Sebai, et al., "Synthesis of some new acid hydrazides structurally related to certain tuberculostatic agents", Egyptian Journal of Pharmaceutical Sciences, vol. 14, No. 1, pp. 67-73, 1973.
Database Chemcats 'Online! ChemDiv, Inc. Product Library,, Jan. 21, 2002, retrieved from STN, Database accession No. 2002:648450, XP002228606.
Database Chemcats 'Online! ChemDiv Inc. Product library, Apr. 26, 2001, retrievd from STN Database accession No. 2001:466545, XP002228607.
Database Chemcats 'Online! AsInEx Compound Collection, May 10, 2001, retrieved from STN Database accession No. 2001:649513, XP002228608.
Gerald M. Reaven, et al. The American Journal of Medicine, vol. 60, pp. 80-88 1976.
Robert W. Stout, Metabolism, vol. 34, No. 12, pp. 7-12 1985.
R.J. Jarrett, Diabetes/Metabolism Reviews, vol. 5, No. 7, pp. 547-558 1989.
Evanthia Diamanti-Kandarakis, et al. European Jouranl of Endocrinology, vol. 138, pp. 269-274 1998.
Andrea Dunaif, Endocrine Reviews, vol. 18, No. 6, pp. 774-800 1997.
Ralph A. Defronzo, et al. Diabetes Care, vol. 14, No. 3, pp. 173-194 1991.

(Continued)

*Primary Examiner*—Celia Chang
(74) *Attorney, Agent, or Firm*—Oblon, Spivak, McClelland, Maier & Neustadt, L.L.P.

(57) ABSTRACT

The present invention is related to the use of oxindole hydrazide derivatives of formula (I) for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). In particular, the present invention is related to the use of oxindole hydrazide derivatives of formula (I) to modulate, notably to inhibit the activity of PTPs, in particular of PTP1B, TC-PTP, SHP and GLEPP-1. The present invention is furthermore related to novel oxindole hydrazide derivatives and method of preparation thereof.(I).

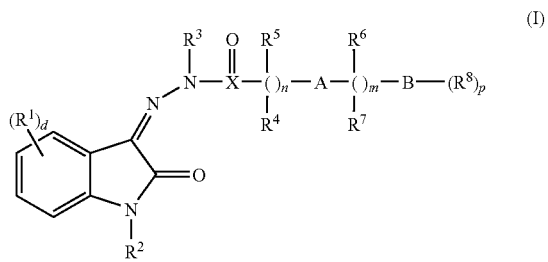

9 Claims, No Drawings

OTHER PUBLICATIONS

Mounib Elchebly, et al. J. Mol. Med, vol. 78, pp. 473-482 2000.
Niels Peter Hundahl Møller, et al. Current Opinion in Drug Discovery & Development, vol. 3, No. 5, pp. 527-540 2000.
Lori D. Klaman, et al. Molecular and Cellular Biology, vol. 20, No. 15, pp. 5479-5489 2000.
Mary C. McGuire, et al. Diabetes, vol. 40, pp. 939-942 1991.
Joseph Meyerovitch, et al. J. Clin. Invest. vol. 84, pp. 976-983 1989.
Janet Sredy, et al. Metabolism: vol. 44, No. 8, pp. 1074-1081 1995.
Zhong-Yin Zhang, Current Opinion in Chemical Biology, vol. 5, No. 4, pp. 416-423 2001.

Jeffrey D. Bjorge, et al. The Journal of Biological Chemistry, vol. 275, No. 52, pp. 41439-41446 Dec. 29, 2000.
Purnima Pathre, et al. Journal of Neuroscience Research, vol. 63, No. 2, pp. 143-150 2001.
Lisa P. Shock, et al. Molecular Brain Research, vol. 28, pp. 110-116 1995.
Brian P. Kennedy, et al. Biochemical Pharmacology, vol. 60, pp. 877-883 2000.
Sebastien Wälchli et al. The Journal of Biological Chemistry, vol. 275, No. 13, pp. 9792-9796 Mar. 31, 2000.

* cited by examiner

OXINDOLE HYDRAZIDE MODULATORS OF PROTEIN TYROSINE PHOSPHATASES (PTPS)

FIELD OF THE INVENTION

The present invention is related to the use of oxindole hydrazide derivatives of formula (I) for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). The compounds of this invention are particularly useful in the treatment of type II or I diabetes. The compounds of this invention are therefore useful for the preparation of a pharmaceutical composition for the treatment and/or prevention of metabolic disorders mediated by insulin resistance or hyperglycemia, comprising diabetes type I and/or II, inadequate glucose tolerance, insulin resistance, obesity, polycystic ovary syndrome (PCOS).

Specifically, the present invention is related to the use of oxindole hydrazides as medicament and the use of oxindole hydrazide derivatives to modulate, notably to inhibit the activity of PTPs, in particular of PTP1B, TC-PTP, SHP and GLEPP-1. The present invention is furthermore related to novel oxindole hydrazide derivatives and a method of preparing them.

BACKGROUND OF THE INVENTION

The prevalence of insulin resistance in glucose intolerant subjects is well known. Reaven et al (*American Journal of Medicine* 1976, 60, 80) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyperinsulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity and with ischemic diseases of the large blood vessels (e.g. atherosclerosis) has been well established by numerous experimental, clinical and epidemiological studies (Stout, *Metabolism* 1985, 34, 7). Statistically significant plasma insulin elevations at 1 and 2 hours after oral glucose load correlate with an increased risk of coronary heart disease.

Since most of these studies actually excluded diabetic subjects, data relating the risk of atherosclerotic diseases to the diabetic condition are not as numerous, but point in the same direction as for non-diabetic subjects. However, the incidence of atherosclerotic diseases in morbidity and mortality statistics in the diabetic population exceeds that of the nondiabetic population (Pyorala et al; Jarrett *Diabetes/Metabolism Reviews* 1989, 5, 547).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* (1998) 138 269-274, Andrea Dunaif; Insulin Resistance and the Polycystic Ovary Syndrome : Mechanism and Implications for Pathogenesis; *Endocrine Reviews* 18(6): 774-800).

The independent risk factors obesity and hypertension for atherosclerotic diseases are also associated with insulin resistance. Using a combination of insulin/glucose clamps, tracer glucose infusion and indirect calorimetry, it was demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of obese people, insulin resistance generates hyperinsulinemia, which is recruited as a mechanism to limit further weight gain via thermogenesis, but insulin also increases renal sodium re-absorption and stimulates the sympathetic nervous system in kidneys, heart, and vasculature, creating hypertension.

It is assumed that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Mounib Elchebly, Alan Cheng, Michel L. Tremblay; Modulation of insulin signaling by protein tyrosine phosphatases; *J. Mol. Med.* (2000) 78:473-482).

Protein-tyrosine phosphatases (PTPs) play an important role in the regulation of phosphorylation of proteins and represent the counterparts of kinases. Among classical PTPs, there are two types : (i) non-receptor or intracellular PTPs; and (ii) receptor-like PTPs. Most intracellular PTPs contain one catalytic domain only, whereas most receptor-like enzymes contain two. The catalytic domain consists of about 250 amino acids (Niels Peter Hundahl Moller et al. Protein tyrosine phosphatases (PTPs) as drug targets: Inhibitors of PTP-1B for the treatment of diabetes; *Current Opinion in Drug Discovery & Development* 2000 3(5):527-540).

The interaction of insulin with its receptor leads to phosphorylation of certain tyrosine molecules within the receptor protein, thus activating the receptor kinase. PTPs dephosphorylate the activated insulin receptor, attenuating the tyrosine kinase activity. PTPs can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTP-alpha. and SH-PTP2 (Lori Klaman et al.; Increased Energy Expenditure, Decreased Adiposity, and Tissue-specific insulin sensitivity in Protein-Tyrosine Phosphatase 1B-Deficient Mice; *Molecular and Cellular Biology* 2000, 5479-5489).

PTP1B is a member of the PTP family. This 50 kDa protein contains a conserved phosphatase domain at residues 30-278 and is localized to the cytoplasmic face of the endoplasmic reticulum by its C-terminal 35 residues. Its interactions with other proteins are mediated by proline-rich regions and SH2 compatible sequence. PTP1B is believed to act as a negative regulator in insulin signaling.

McGuire et al. (*Diabetes* 1991, 40, 939), demonstrated that non-diabetic glucose intolerant subjects possessed significantly elevated levels of PTP activity in muscle tissue vs. normal subjects, and that insulin infusion failed to suppress PTP activity as it did in insulin sensitive subjects.

Meyerovitch et al (*J. Clinical Invest.* 1989, 84, 976) observed significantly increased PTP activity in the livers of two rodent models of IDDM, the genetically diabetic BB rat, and the STZ-induced diabetic rat. Sredy et al (*Metabolism,*

44, 1074, 1995) observed similar increased PTP activity in the livers of obese, diabetic ob/ob mice, a genetic rodent model of NIDDM.

Zhang et al (*Curr. Opin. Chem. Biol.*, 5(4), p.416-23 (English) 2001) mentioned that PTPs are also implicated in a wide variety of other disorders, including cancer. Bjorge, J. D et al. (*J. Biol. Chem.*, 275(52), p.41439-41446 (English) 2000) indicate that PTP1B is the primary protein-tyrosine phosphatase capable of dephosphorylating c-Src in several human breast cancer cell lines and suggests a regulatory role for PTP1B in the control of c-Src kinase activity.

Pathre et al (*J. Neurosci. Res.*, 63(2), p.143-150 (English) 2001) describes that PTP1B regulates neurite extension mediated by cell-cell and cell-matrix adhesion molecules. Further, Shock L. P et al (*Mol. Brain. Res.*, 28(1), p.110-16 (English) 1995) demonstrates that a distinct overlapping set of PTPs is expressed in the developing brain and retinal Mueller glia, including 2 novel PTPs that may participate in neural cell communication.

The insulin receptor (IR) is a prototypical tyrosine kinase receptor whose ligand binding and dimerization results in auto-phosphorylation on multiple tyrosines. This is followed by the recruitment and phosphorylation of IRS1-4 (depending on the tissue) and P13K Although vanadium-containing compounds have been known since the $19^{th}$ century to alleviate diabetes, it was understood only recently that these inhibitors stimulate the insulin signaling pathway by blocking PTP action. Evidence for the involvement of the IR (insulin receptor) and IRS-1 in this phenotype was that both proteins show increased tyrosine phosphorylation in the PTP1B-mutated mice. The available data strongly suggest that in particular PTP1B is a promising target for the development of drugs to treat diabetes and obesity (Brian P. Kennedy and Chidambaram Ramachandran; Protein Tyrosine Phosphatase-1B in Diabetes; *Biochemical Pharmacology*, Vol. 60, pp. 877-883, 2000).

The compounds of this invention turned out to be inhibitors of PTPs. They are particularly useful in the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). In particular the compounds of this invention are useful in the treatment and/or prevention of diabetes type II.

SUMMARY OF THE INVENTION

The invention therefore relates to the use of oxindole hydrazide derivatives of formula (I) for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS)

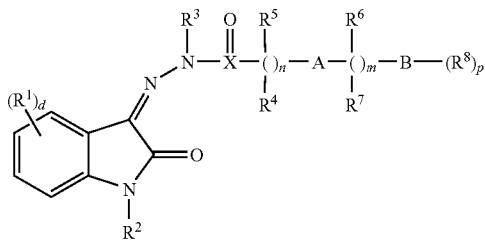

wherein X, $R^1$, $R^2$, $R^3$, $R^4$, $R^5$, $R^6$, $R^7$, $R^8$, m, n and p are defined in detail in the description below.

The invention further relates to the use of oxindole hydrazides as medicament and the use of oxindoel hydrazide derivatives to modulate, notably to inhibit the activity of PTPs, in particular of PTP1B, TC-PTP, SHP and GLEPP-1. The present invention is furthermore related to novel oxindole hydrazide derivatives and a method of preparing them.

DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"PTPs" are protein tyrosine phosphatases and include for instance PTP1B, TC-PTP, PTP-β, DEP-1, LAR, SHP-1, SHP-2, GLEPP-1, PTP-κ, PTP-µ, VHR, hVH5, LMW-PTP, PTEN.

"Aryl" refers to an unsaturated aromatic carbocyclic group of from 6 to 14 carbon atoms having a single ring (e.g., phenyl) or multiple condensed rings (e.g., naphthyl). Specific aryl include phenyl, naphthyl, phenantrenyl and the like.

"$C_1$-$C_6$-alkyl aryl" refers to $C_1$-$C_6$-alkyl groups having an aryl substituent, including benzyl phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4oxadiazolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkanoic acid" refers to monovalent alkyl groups having from 1-6 carbon atoms and comprising a carboxyl group —COOH as functional group e.g. methanoic acid, ethanoic acid or propanoic acid.

"Alkenyl" refers to alkenyl groups preferably having from 2 to 6 carbon atoms and having at least 1 or 2 sites of alkenyl unsaturation. Specific alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"Alkynyl" refers to alkynyl groups preferably having from 2 to 6 carbon atoms and having at least 1-2 sites of alkynyl unsaturation, specific alkynyl groups include ethynyl (-C≡H), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Specific cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"Heterocycloalkyl" refers to a $C_3$-$C_8$-cycloalkyl group according to the definition above, in which 1 to 3 carbon atoms are replaced by heteroatoms chosen from the group consisting of O, S, NR, R being defined as hydrogen or $C_1$-$C_6$ alkyl. Specific heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", heterocycloalkyl"heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NR(CO)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2propionylamino) ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N$^+$RR'R", where each R, R',R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Specific sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, may be substituted by moieties including "nitro", "hydroxy", "halogen", "carboxy", "amino" or groups such as "alkyl" (e.g."trihalomethyl"), "alkenyl", "alkynyl", "aryl" "cycloalkyl" and "heteroaryl". Said groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like Alternatively said substitution could also comprise situations where neighboring substituents have undergone ring closure, notably when viccinal functional substituents are involved, thus forming e.g. lactams, lac-tons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula (I) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR,R',R"+ Z−, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have the inventive set out activity as PTP inhibitors.

Said formula also comprises its tautomers, its geometrical isomers, its optically active forms as enantiomers, diastereomers and its racemate forms, as well as pharmaceutically acceptable salts thereof. Specific pharmaceutically acceptable salts of the formula (I), are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

A first aspect of the present invention consists in the use of compounds of formula (I):

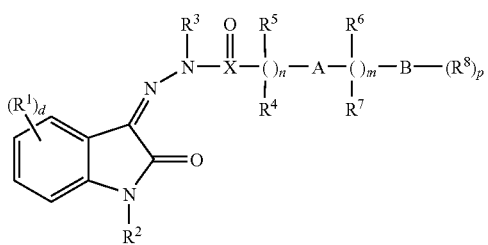

as well as its tautomers, geometrical isomers, its optically active forms as enantiomers, diastereomers and its racemate forms, as well as pharmaceutically acceptable salts thereof, for the preparation of pharmaceutical compositions for the treatment and/or prevention of metabolic disorders mediated by insulin resistance or hyperglycemia, comprising diabetes type I and/or II, inadequate glucose tolerance, insulin resistance, hyperlipidemia, hypercholesterolemia, obesity and poycystic ovary syndrome (PCOS).

In formula I the substituents are as follows:

$R^1$ is either halogen or —(C=O)N—($C_6$-$C_{18}$)-alkyl, d is 1 to 4. In a further embodiment d is 1 or 2, in particular 1.

$R^2$ is selected from the group consisting of H, —CO—NH—R or —$(CH_2)_u$—CO—OR wherein u is an integer from 1 to 7, R is H or substituted or unsubstituted ($C_1$-$C_6$) alkyl (thus giving a $R^2$ being e.g. a methyl methanoate, -ethanoate, -propanoate, -butanoate, -pentanoate or -hexanoate group). In one embodiment $R^2$ is H.

$R^3$ is selected from the group comprising or consisting of H or substituted or unsubstituted $C_1$-$C_6$ alkyl. In one embodiment $R^2$ and/or $R^3$ is H.

$R^4$, $R^5$, $R^6$ and $R^7$ are each independently from each other selected from the group consisting of H, halogen, —$NO_2$, —OH, substituted or unsubstituted ($C_1$-$C_6$)-alkyl, substituted or unsubstituted 3-8 membered cycloalkyl, substituted or unsubstituted 3-8 membered heterocycloalkyl which may contain 1-2 further heteroatoms selected from O, N or S, substituted or unsubstituted ($C_1$-$C_6$)-alkyl-heterocycloalkyl wherein said heterocycloalkyl may contain 1-2 further heteroatoms selected from O, N or S, substituted or unsubstituted aryl, substituted or unsubstituted ($C_1$-$C_6$)-alkyl-aryl, substituted or unsubstituted heteroaryl, substituted or unsubstituted ($C_1$-$C_6$)alkyl-heteroaryl. In one embodiment $R^4$, $R^5$, $R^6$ and $R^7$ are H or substituted or unsubstituted alkyl groups, like methyl or ethyl groups. According to a specific embodiment, all of $R^4$, $R^5$, $R^6$ and $R^7$ are H.

$R^8$ is selected from the group comprising or consisting of H, halogen, hydroxy, acyl, amino, carboxy, cyano, nitro, an unsubstituted or substituted $C_1$-$C_6$-alkyl, an unsubstituted or substituted $C_2$-$C_6$-alkenyl, an unsubstituted or substituted $C_2$-$C_6$-alkynyl, an unsubstituted or substituted $C_1$-$C_6$-alkyl carboxy, an unsubstituted or substituted $C_1$-$C_6$-alkyl acyl, an unsubstituted or substituted $C_1$-$C_6$- allyl alkoxycarbonyl, an unsubstituted or substituted aminocarbonyl, an unsubstituted or substituted carbonylamino, an unsubstituted or substituted $C_1$-$C_6$-alkyl aminocarbonyl, an unsubstituted or substituted hydrazinocarbonyl, an unsubstituted or substituted $C_1$-$C_6$-alkyl acyloxy, acylamino, an unsubstituted or substituted $C_1$-$C_6$-alkyl acylamino, ureido, an unsubstituted or substituted $C_1$-$C_6$-alkyl ureido, an unsubstituted or substituted $C_1$-$C_6$-alkyl carbamate, an unsubstituted or substituted $C_1$-$C_6$-alkyl amino, $C_1$-$C_6$ alkoxy, an unsubstituted or substituted $C_1$-$C_6$-alkyl alkoxy, sulfanyl, an unsubstituted or substituted $C_1$-$C_6$-alkyl sulfanyl, sulfinyl, an unsubstituted or substituted $C_1$-$C_6$-alkyl sulfinyl, sulfonyl, sulfonylamino, an unsubstituted or substituted $C_1$-$C_6$-alkyl sulfonyl, an unsubstituted or substituted $C_1$-$C_6$-alkyl sulfonylaminoaryl, substituted or unsubstituted aryl, substituted or unsubstituted heteroaryl, an unsubstituted or substituted $C_3$-$C_8$-cycloalkyl or heterocycloalkyl, an unsubstituted or substituted $C_1$-$C_6$-alkyl aryl, an unsubstituted or substituted $C_1$-$C_6$-alkyl heteroaryl, an unsubstituted or substituted $C_2$-$C_6$-alkenyl-aryl or -heteroaryl, an unsubstituted or substituted $C_2$-$C_6$-alkynyl aryl or -heteroaryl.

In one embodiment $R^8$ is selected from the group consisting of H, halogen, cyano, substituted or unsubstituted ($C_1$-$C_6$)alkyl (e.g. —$CF_3$ or ($C_1$-$C_6$)-alkanoic acid or ester), substituted or unsubstituted aryl, substituted or unsubstituted heteroaryl, —SO—$R^9$, —SO—$R^9$, substituted or unsubstituted ($C_1$-$C_6$)alkyl-$SO_2$—$R^9$, —$NO_2$, —$N(R)_2$, substituted or unsubstituted ($C_1$-$C_6$)alkyl-O—$R^9$, $—SR^9$, —(C=O)O—$R^9$, —(C=O)—$R^9$, —(C=O)N($R^9$)$_2$, —(C=O)NH—$R^9$, —(C=O)N$R^9$—N($R^9$)$_2$, —N$R^9$—(C=O)—N($R^9$)$_2$, —N$R^9$—($SO_2$—$R^9$), —NH—(C=O)—$R^9$, substituted or unsubstituted ($C_1$-$C_6$)-alkyl-NH—(C=O)—$R^9$, —N$R^9$—(C=O)—$R^9$ wherein $R^9$ is selected from the group consisting of H, substituted or unsubstituted ($C_1$-$C_6$)-alkyl, substituted or unsubstituted $C_3$-$C_8$ cycloalkyl, substituted or unsubstituted 3-8 membered heterocycloalkyl which may contain 1-2 further heteroatoms selected from O, N or S, substituted or unsubstituted ($C_1$-$C_6$)-alkyl-heterocycloalkyl wherein said heterocycloalkyl may contain 1-2 further heteroatoms selected from O, N or S, substituted or unsubstituted aryl, substituted or unsubstituted ($C_1$-$C_6$)-alkyl-aryl, substituted or unsubstituted ($C_1$-$C_6$)-alkoxy-aryl, substituted or unsubstituted heteroaryl, substituted or unsubstituted ($C_1$-$C_6$)-alkyl-heteroaryl or substituted or unsubstituted ($C_1$-$C_6$)-alkoxy-heteroaryl, substituted or unsubstituted ($C_1$-$C_6$)-alkyl-COO$R^{10}$ wherein $R^{10}$ is H or substituted or unsubstituted ($C_1$-$C_6$)alkyl or —$NH_2$.

A is selected from the group consisting of a bond, —O—, —S—, —SO—, —$SO_2$—, amino, urea, sulfonylamino or acylamino;

In one embodiment A is a bond or O.

B is selected from the group consisting of substituted or unsubstituted arylene, substituted or unsubstituted heteroarylene, substituted or unsubstituted heterocycloalkylene or substituted or unsubstituted cycloalkylene.

X is C, S or SO.

m, n and p are each independently from each other an integer from 0 to 6. In one embodiment m is 0, 1 or 2, while n is 0 or 1. In a further embodiment p is 1 or 2. In still a further embodiment p is 1.

Examples of B include optionally substituted phenyl, naphthyl, phenantrenyl, pyrrolyl, furyl, thienyl, imidazolyl, oxazolyl, isoxazolyl, thiazolyl, isothiazolyl, pyrazolyl, [1,3]thiazolo[3,2-b][1,2,4]triazolyl, carbazolyl, 1,2,3-triazolyl, 1,2,4-triazolyl, 1,2,3-oxadiazolyl, benzo(2,1,3)oxadiazolyl, benzo(1,2,5)oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, benzothiazolyl, benzoxazolyl, pyridazinyl, pyrimidyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, cyclopropyl, cyclobutyl, cyclopentyl, cyclohexyl, cycloheptyl, cyclooctyl, oxolanyl, pyrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl or morpholinyl.

According to one embodiment B is selected from the group consisting of phenyl, biphenyl, benzo(1,2,5)oxadiazolyl, furyl, thiadiazolyl, thienyl, thiazolyl, indolyl, piperidinyl, tetrazolyl, 1,2,3-triazolyl, 1,2,4-triazolyl and pyridyl.

According to a further embodiment, B is a substituted or an unsubstituted phenyl.

According to a further embodiment, $R^1$ is Br or I and d is 1.

The substituents $R^4$, $R^5$, $R^6$ and $R^7$ in—one embodiment—are independently from each other selected from the group consisting of H and substituted or unsubstituted ($C_1$-$C_6$)-alkyl.

Still a further embodiment comprises oxindoles of formula I wherein n and m are each 0, A is a bond, B is a substituted or unsubstituted phenyl, p is 1 and $R^8$ is —NH—CO—($C_1$-$C_6$-alkyl)-$Ar_1$ or —O—$Ar_1$ wherein $Ar_1$ is a substituted or unsubstituted phenyl group.

A further aspect of the present invention is related to the use of oxindole hydrazide derivatives of formula (Ia)

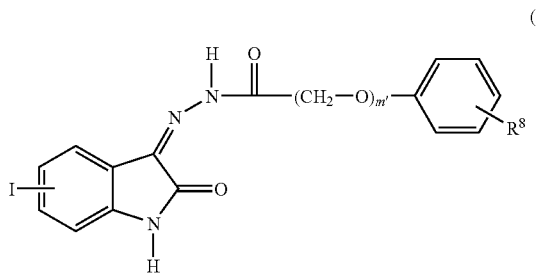

(Ia)

wherein m' is 0 or 1 and $R^8$ is selected from the group consisting of H, halogen, cyano, substituted or unsubstituted ($C_1$-$C_6$)alkyl (e.g. a —$CF_3$ moiety or a ($C_1$-$C_6$)-alkanoic acid or ester), —$SR^9$, —SO—$R^9$, —$SO_2$—$R^9$, substituted or unsubstituted aryl, substituted or unsubstituted heteroaryl, substituted or unsubstituted ($C_1$-$C_6$)alkyl-$SO_2$—$R^9$, —$NO_2$, —$N(R^9)_2$, —O—$R^9$, ($C_1$-$C_6$)alkyl-$OR^9$, —(C═O)O—$R^9$, —(C═O)—$R^9$, —(C═O)N($R^9)_2$, —(C═O)NHR$^9$, —(C═O)NR$^9$—N($R^9)_2$, —N—(C═O)—$R^9$, —$NR^9$—(C═O)—N($R^9)_2$, —$NR^9$—($SO_2$—$R^9$), —NH—(C═O)—$R^9$, ($C_1$-$C_6$)alkyl-NH(C═O)—$R^9$ or —$NR^9$—(C═O)—$R^9$ and where $R^9$ is as above defined, for the preparation of a pharmaceutical composition for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS).

In a further embodiment of the invention, $R^8$ is —$NO_2$ or —$COOR^9$ wherein $R^9$ is as above defined.

Specifically, the compounds according to formula (I) and (Ia) are suitable for the modulation of the activity of PTPs, in particular of PTP1B, TC-PTP, SHP and GLEPP-1. It is assumed that the compounds of the present invention are therefore useful for the treatment and/or prevention of disorders which are mediated by FTPs, in particular of PTP1B, TC-PTP, SHP and GLEPP-1. Said treatment involves the modulation—notably the down regulation or the inhibition—of PTPs, particularly of PTP1B, TC-PTP, SHP and GLEPP-1 and more particularly PTP1B.

More specifically, compounds according to formula (I) and (Ia) are particularly useful for the treatment and/or prevention of diabetes type II.

A further aspect of the present invention is related to novel compounds of the following formula (II)

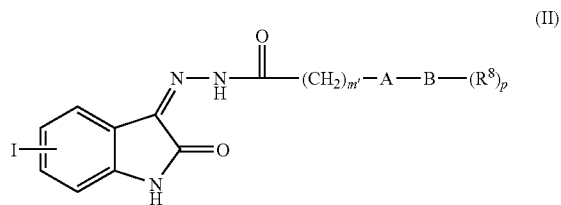

(II)

wherein m' is as above-defined and p is an integer from 1 to 3.

A is O, or a bond, B is selected from the group consisting of substituted or unsubstituted arylene, substituted or unsubstituted heteroarylene, substituted or unsubstituted heterocycloalkylene or substituted or unsubstituted cycloalkylene, further B is substituted or unsubstituted a phenyl group.

$R^8$ is selected from the group consisting of is selected from the group comprising or consisting of H, halogen, hydroxy, acyl, amino, carboxy, cyano, nitro, an unsubstituted or substituted $C_1$-$C_6$-alkyl, an unsubstituted or substituted $C_2$-$C_6$-alkenyl, an unsubstituted or substituted $C_2$-$C_6$-alkynyl, an unsubstituted or substituted $C_1$-$C_6$-alkyl carboxy, an unsubstituted or substituted $C_1$-$C_6$-alkyl acyl, an unsubstituted or substituted $C_1$-$C_6$-alkyl alkoxycarbonyl, an unsubstituted or substituted $C_1$-$C_6$-alkyl aminocarbonyl, an unsubstituted or substituted $C_1$-$C_6$-alkyl acyloxy, acylamino, an unsubstituted or substituted $C_1$-$C_6$-alkyl acylamino, ureido, an unsubstituted or substituted $C_1$-$C_6$-alkyl ureido, an unsubstituted or substituted $C_1$-$C_6$-alkyl carbamate, an unsubstituted or substituted $C_1$-$C_6$-alkyl amino, $C_1$-$C_6$ alkoxy, an unsubstituted or substituted $C_1$-$C_6$-alkyl alkoxy, sulfanyl, an unsubstituted or substituted $C_1$-$C_6$-alkyl sulfanyl, sulfinyl, an unsubstituted or substituted $C_1$-$C_6$-alkyl sulfinyl, sulfonyl, sulfonylamino, an unsubstituted or substituted $C_1$-$C_6$-alkyl sulfonyl, an unsubstituted or substituted $C_1$-$C_6$-alkyl sulfonylaminoaryl, substituted or unsubstituted aryl, substituted or unsubstituted heteroaryl, an unsubstituted or substituted $C_3$-$C_8$-cycloalkyl or heterocycloalkyl, an unsubstituted or substituted $C_1$-$C_6$-alkyl aryl, an unsubstituted or substituted $C_1$-$C_6$-alkyl heteroaryl, an unsubstituted or substituted $C_2$-$C_6$-alkenyl-aryl or -heteroaryl, an unsubstituted or substituted $C_2$-$C_6$-alkynyl aryl or -heteroaryl.

The Formula (II) does not include the following seven compounds, though:

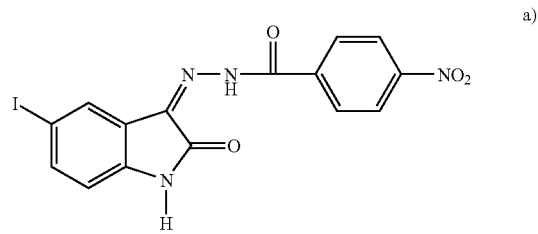

a)

-continued b) 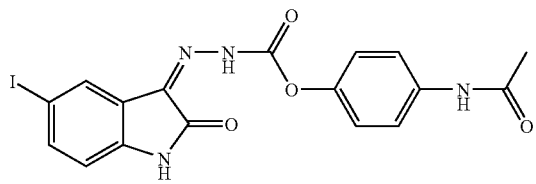

c) 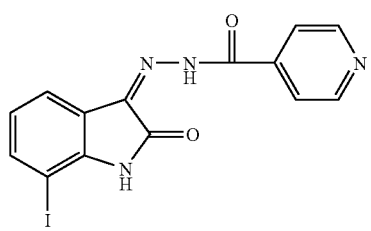

d) 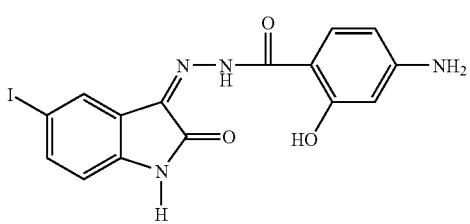

e) 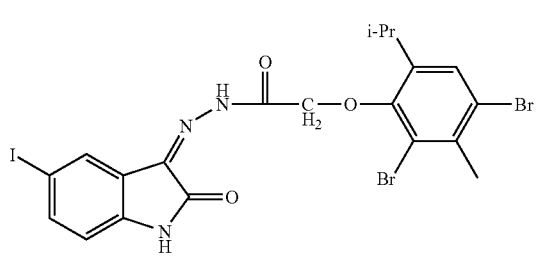

f) 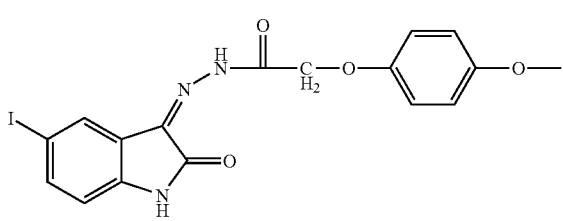

g) 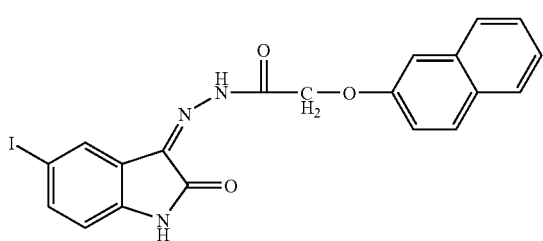

Compounds a), b), e), f) and g) are commercially available from catalogues of ChemDiv. Inc., AsInEx and SPECS and BioSPECS and represent compounds having so far not been described as having any therapeutic utility. Compounds c) and d) are specifically disclosed in *Egypt. J. Pharm. Sci.,* 14(1) English) 1973.

In one embodiment $R^8$ is selected from the group consisting of H, halogen, cyano, substituted or unsubstituted ($C_1$-$C_6$)alkyl (e.g. —$CF_3$ or ($C_1$-$C_6$)-alkanoic acid or ester), substituted or unsubstituted aryl, substituted or unsubstituted heteroaryl, —SO—$R^9$, —$SO_2$—$R^9$, ($C_1$-$C_6$)alkyl-$SO_2$—$R^9$, —$NO_2$, —$N(R^9)_2$, ($C_1$-$C_6$)-alkyl-O—$R^9$, —$SR^9$, —$SO_2$—$R^9$, —(C=O)O—$R^9$, —(C=O)—$R^9$, —(C=O)N($R^9)_2$, —(C=O)NH—$R^9$, —(C=O)N$R^9$—N($R^9)_2$, —$NR^9$—(C=O)—N($R^9)_2$, —$NR^9$—($SO_2$—$R^9$), —NH—(C=O)—$R^9$, ($C_1$-$C_6$)-alkyl—NH—(C=O)—$R^9$, —$NR^9$—(C=O)—$R^9$ wherein $R^9$ is as above-defined.

In a specific embodiment of the invention, m' is 0, p is 0 or 1, A is a bond or O, B is a substituted or unsubstituted phenyl group and $R^8$ is selected in the group consisting of —$NO_2$, —$CO_2$—$R^9$ and —NH—(C=O)—$R^9$ wherein $R^9$ is as above defined.

Novel compounds of Formula II are in particular those of the group consisting of:

N-(4-{[2-(5-Iodo-2-oxo-1,2-dihydro-3H-indol-3-ylidene)hydrazino]carbonyl}phenyl)-3-phenylpropanamide 3,5-Dichloro-N'-(5-iodo-2-oxo-1,2-dihydro-3H-indol-3-ylidene)benzohydrazide N'-(5-Iodo-2-oxo-1,2-dihydro-3H-indol-3-ylidene)benzohydrazide N'-(5-Iodo-2-oxo-1,2-dihydro-3H-indol-3-ylidene)-4-methylbenzohydrazide 4-Hydroxy-N'-(5-iodo-2-oxo-1,2-dihydro-3H-indol-3-ylidene)benzohydrazide 3-Hydroxy-N'-(5-iodo-2-oxo-1,2-dihydro-3H-indol-3-ylidene)benzohydrazide N'-(5-Iodo-2-oxo-1,2-dihydro-3H-indol-3-ylidene)-2-nitrobenzohydrazide N'-(5-Iodo-2-oxo-1,2-dihydro-3H-indol-3-ylidene)-4-phenoxybenzohydrazide N'-(5-Iodo-2-oxo-1,2-dihydro-3H-indol-3-ylidene)-4-(trifluoromethyl)benzohydrazide 4-tert-butyl-N'-(5-Iodo-2-oxo-1,2-dihydro-3H-indol-3-ylidene)benzohydrazide N'-(5-Iodo-2-oxo-1,2-dihydro-3H-indol-3-ylidene)[1,1'-biphenyl]-4-carbohydrazide 4-Bromo-N'-(5-iodo-2-oxo-1,2-dihydro-3H-indol-3-ylidene)benzohydrazide N'-(5-Iodo-2-oxo-1,2-dihydro-3H-indol-3-ylidene)-3-nitrobenzohydrazide N'-(5-Iodo-2-oxo-1,2-dihydro-3H-indol-3-ylidene)-4-methoxybenzohydrazide N'-(5-Iodo-2-oxo-1,2-dihydro-3H-indol-3-ylidene)-3-methoxybenzohydrazide 4-Amino-N'-(5-iodo-2-oxo-1,2-dihydro-3H-indol-3-ylidene)benzohydrazide 4-(Dimethylamino)-N'-(5-iodo-2-oxo-1,2-dihydro-3H-indol-3-ylidene)benzohydrazide N'-(5-Iodo-2-oxo-1,2-dihydro-3H-indol-3-ylidene)-2-(4-nitrophenoxy)acetohydrazide N'-(5-Iodo-2-oxo-1,2-dihydro-3H-indol-3-ylidene)-4-(trifluoromethoxy)benzohydrazide N'-(5-Iodo-2-oxo-1,2-dihydro-3H-indol-3-ylidene)-2,1,3-benzoxadiazole-5-carbohydrazide N'-(5-Iodo-2-oxo-1,2-dihydro-3H-indol-3-ylidene)-(5-nitro-(2-furohydrazide))

Methyl 4-{[2-(5-iodo-2-oxo-1,2-dihydro-3H-indol-3-ylidene)hydrazino]carbonyl}benzoate Methyl 4-{2-[2-(5-iodo-2-oxo-1,2-dihydro-3H-indol-3-ylidene)hydrazino]-2-oxoethoxy}benzoate 4-{[2-(5-Iodo-2-oxo-1,2-dihydro-3H-indol-3-ylidene)hydrazino]carbonyl}benzoic acid 4-Iodo-N'-(5-iodo-2-oxo-1,2-dihydro-3H-indol-3-ylidene)benzohydrazide N'-(5-Iodo-2-oxo-1,2-dihydro-3H-indol-3-ylidene)-3-phenoxybenzohydrazide N'-(5-Iodo-2-oxo-1,2-dihydro-3H-indol-3-ylidene)-2-(4-iodophenoxy)acetohydrazide N'-(5-Iodo-2-oxo-1,2-dihydro-3H-indol-3-ylidene)-2-[(4-methylphenyl)sulfonyl]acetohydrazide 2-{[(2-Furylmethyl)sulfonyl]methyl}-N'-(5-Iodo-2-oxo-1,2-dihydro-3H-indol-3-ylidene)-1,3-thiazole-4-carbohydrazide 2-Hydroxy-N'-(5-Iodo-2-oxo-1,2-dihydro-3H-indol-3-ylidene)benzohydrazide N-(2-Furylmethyl)-N'-{2-[2-5-iodo-2-oxo-1,2-dihydro-3H-indol-3-ylidene)hydrazino]-2-oxoethyl}urea N'-(5-Iodo-2-oxo-1,2-dihydro-3H-indol-3-ylidene)-4-(methylsulfanyl)benzohydrazide Methyl 6-{[2-(5-iodo-2-oxo-1,2-dihydro-3H-indol-3-ylidene)hydrazino]carbonyl}nicotinate Benzyl 4-{2-[2-(5-iodo-2-oxo-1,2-dihydro-3H-indol-3-ylidene)hydrazino]-2-oxoethoxy}benzoate N-(4-{[2-(5-Iodo-2-oxo-1,2-dihydro-3H-indol-3-ylidene)hydrazino]carbonyl}phenyl)-2-furamide N-(4-{[2-(5-Iodo-2-oxo-1,2-dihydro-3H-indol-3-ylidene)hydrazino]carbonyl}phenyl)hexanamide 4-Cyano-N-(4{[2-(5-iodo-2-oxo-1,2-dihydro-3H-indol-3-ylidene)hydrazino]carbonyl}phenyl)benzamide 4-(Hexyloxy)-N-(4-{[2-(5-iodo-2-oxo-1,2-dihydro-3H-indol-3-ylidene)hydrazino]carbonyl}phenyl)benzamide 4-Heptyl-N-(4-{[2-(5-iodo-2-oxo-1,2-dihydro-3H-indol-3-ylidene)hydrazino]carbonyl}phenyl)benzamide 2-{2-Nitro-4,5-dimethoxyphenyl}-N'-[5-iodo-2-oxo-1,2-dihydro-3H-indol-3-yliden)acetohydrazide N'-(5-Iodo-2-oxo-1,2-dihydro-3H-indol-3-ylidene)-1-(3-pyridinylmethyl)-4-piperidinecarbohydrazide 2-Amino-5-nitro-N'-(5-iodo-2-oxo-1,2-dihydro-3H-indol-3-ylidene)benzohydrazide 2-[5-(3-Nitrophenyl)-2H-tetrazol-2-yl]-N'-(5-iodo-2-oxo-1,2-dihydro-3H-indol-3-ylidene)acetohydrazide N'-(5-Iodo-2-oxo-1,2-dihydro-3H-indol-3-ylidene)-2-[5-(1-pyrrolidinyl)-2H-tetrazol-2-yl]acetohydrazide N'-(5-Iodo-2-oxo-1,2-dihydro-3H-indol-3-ylidene)-2-[5-(4-morpholinyl)-2H-tetrazol-2-yl]acetohydrazide 4-{2-[2-(5-Iodo-2-oxo-1,2-dihydro-3H-indol-3-ylidene)hydrazino]-2-oxoethoxy}benzoic acid 4-{[2-(5-Iodo-2-oxo-1,2-dihydro-3H-indol-3-ylidene)hydrazino]carbonyl}-N-phenylbenzamide 4-Cyano-N-(3-{[2-(5-iodo-2-oxo-1,2-dihydro-3H-indol-3-ylidene)hydrazino]carbonyl}phenyl)benzamide N'-[5-Iodo-2-oxo-1,2-dihydro-3H-indol-3-ylidene]-4-[4-(4-morpholinylmethyl) phenoxy]benzohydrazide N-(4-{[2-(5-Iodo-2-oxo-1,2-dihydro-3H-indol-3-ylidene)hydrazino]carbonyl}phenyl) benzamide 4-(Benzyloxy)-N'-(5-iodo-2-oxo-1,2-dihydro-3H-indol-3-ylidene)benzohydrazide N-(3-{[2-(5-Iodo-2-oxo-1,2-dihydro-3H-indol-3-ylidene)hydrazino]carbonyl}phenyl)-3-phenylpropanamide 4-{[2-(5-Iodo-2-oxo-1,2-dihydro-3H-indol-3-ylidene)hydrazino]carbonyl}-N-{3-[(trifluoromethyl)sulfonyl]phenyl}benzamide 4-Chloro-N-(4-{[2-(5-iodo-2-oxo-1,2-dihydro-3H-indol-3-ylidene)hydrazino]carbonyl}benzyl)benzamide Methyl 4-{3-[2-(5-iodo-2-oxo-1,2-dihydro-3H-indol-3-ylidene)hydrazino]-3-oxopropyl}benzoate 2-[(2-Chlorophenoxy)methyl]-N'-(5-iodo-2-oxo-1,2-dihydro-3H-indol-3-ylidene)-1,3-thiazole-4-carbohydrazide N'-(5-Iodo-2-oxo-1,2-dihydro-3H-indol-3-ylidene)-2-(2-phenyl[1,3]thiazolo[3,2-b][1,2,4]triazol-6-yl)acetohydrazide 4-{[3-Chloro-5-(trifluoromethyl)-2-pyridinyl]amino}-N'-[5-iodo-2-oxo-1,2-dihydro-3H-indol-3-ylidene]butanohydrazide 2-{[3-Chloro-5-trifluoromethyl)-2-pyridinyl]amino}-N'-(5-iodo-2-oxo-1,2-dihydro-3H-indol-3-ylidene)acetohydrazide 1-Benzoyl-N'-(5-iodo-2-oxo-1,2-dihydro-3H-indol-3-ylidene)-4-piperidinecarbohydrazide N-(4-{[2-(5-Iodo-2-oxo-1,2-dihydro-3H-indol-3-ylidene)hydrazino]carbonyl}phenyl)-2-phenoxyacetamide N-(4-{[2-(5-Iodo-2-oxo-1,2-dihydro-3H-indol-3-ylidene)hydrazino]carbonyl}phenyl)-nicotinamide 3-Nitro-N-(4-{[2-(5-iodo-2-oxo-1,2-dihydro-3H-indol-3-ylidene)hydrazino]carbonyl}-benzyl)benzamide N-(4-{[2-(5-Iodo-2-oxo-1,2-dihydro-3H-indol-3-ylidene)hydrazino]carbonyl}phenyl)[1,1'-biphenyl]-4-carboxamide Methyl-3-{2-[2-(5-iodo-2-oxo-1,2-dihydro-3H-indol-3-ylidene)hydrazino]-2-oxoethoxy}benzoate Methyl 4-{[[2-(5-iodo-2-oxo-1,2dihydro-3H-indol-3-ylidene)hydrazino](oxo)acetyl]-amino}benzoate 3-(1,3-Benzodioxol-5-yl)-N-(4-{[2-(5-iodo-2-oxo-1,2dihydro-3H-indol-3-ylidene)-hydrazino]carbonyl}phenyl)propanamide 4-[(4-{[2-(5-Iodo-2-oxo-1,2-dihydro-3H-indol-3-ylidene)hydrazino]carbonyl}benzoyl)-amino]benzoic acid 3-(3,4-Dihydroxyphenyl)-N-(4-{[2-(5-iodo-2-oxo-1,2-dihydro-3H-indol-3-ylidene)hydrazino]carbonyl}phenyl)propanamide 3-(3-Hydroxyphenyl)-N-(4-{[2-(5-iodo-2-oxo-1,2-dihydro-3H-indol-3-ylidene)hydrazino]-carbonyl}phenyl)propanamide N'-(5-Iodo-2-oxo-1,2-dihydro-3H-indol-3-ylidene)-6-methoxy-5-nitronicotinohydrazide 3-{[2-(5-Iodo-2-oxo-1,2-dihydro-3H-indol-3-ylidene)hydrazino]sulfonyl}benzoic acid 2-Hydroxy-5-{[2-(5-iodo-2-oxo-1,2-dihydro-3H-indol-3-ylidene)hydrazino]sulfonyl}-benzoic acid N'-(5-Iodo-2-oxo-1,2-dihydro-3H-indol-3-ylidene)-5-(2-pyridinyl)-2-thiophenesulfono-hydrazide 4-Chloro-N'-(5-iodo-2-oxo-1,2-dihydro-3H-indol-3-ylidene)-3-nitrobenzenesulfono-hydrazide Methyl {3-[(4-hydroxybenzoyl)hydrazono]-5-iodo-2-oxo-2,3-dihydro-1H-indol-1-yl}acetate N-Dodecyl-3-[(4-hydroxybenzoyl)hydrazono]-5-iodo-2-oxo-2,3-dihydro-1H-indole-1-carboxamide Methyl (3-{[4-(hexanoylamino)benzoyl]hydrazono}-5-iodo-2-oxo-2,3-dihydro-1H-indol-1-yl)acetate Further novel compounds falling into Formula (I) are selected from the group consisting of:

4-Nitro-N'-(5-bromo-2-oxo-1,2-dihydro-3H-indol-3-ylidene)benzohydrazide

Methyl 4-{2-[2-(5-bromo-2-oxo-1,2-dihydro-3H-indol-3-ylidene)hydrazino]-2-oxoethoxy}benzoate 4-Methoxy-N'-(5-bromo-2-oxo-1,2-dihydro-3H-indol-3-ylidene)benzohydrazide N-(4-{[2-(5-Bromo-2-oxo-1,2dihydro-3H-indol-3-ylidene)hydrazino]carbonyl}phenyl)-3-phenylpropanamide N'-(5-Bromo-2-oxo-1,2-dihydro-3H-indol-3-ylidene)-4-{3-[2-(5-bromo-2-oxo-1,2-dihydro-3H-indol-3-ylidene)hydrazino]-3-oxopropyl}benzohydrazide N-(4-{[2-(5-Bromo-2-oxo-1,2dihydro-3H-indol-3-ylidene)hydrazino]carbonyl}phenyl)-2-phenoxyacetamide N-(4-{[2-(5-Bromo-2-oxo-1,2dihydro-3H-indol-3-ylidene)hydrazino]carbonyl}benzyl)-3-nitrobenzamide Methyl 3-{2-[2-(5-bromo-2-oxo-1,2-dihydro-3H-indol-3-ylidene)hydrazino]-2-oxoethoxy}benzoate N'-(5-Bromo-2-oxo-1,2-dihydro-3H-indol-3-ylidene)-2-[4-(1H-tetrazol-5-yl)phenoxy]-acetohydrazide (3-{[4-(hexanoylamino)benzoyl]hydrazono}-5-iodo-2-oxo-2,3-dihydro-1H-indol-1-yl)acetic acid (3-{[4-(hexanoylamino)benzoyl]hydrazono}-5-iodo-2-oxo-2,3-dihydro-1H-indol-1-yl)acetic acid, tromethanine (2-amino-2-hydroxymethyl-1,3-propanediol) salt (3-{[4-(hexanoylamino)benzoyl]hydrazono}-5-iodo-2-oxo-2,3-dihydro-1H-indol-1-yl)acetic acid, N-methyl-D-glucamine (1-deoxy-1-(methylamino)glucitol) salt 2-(4-cyanophenoxy)-N'-(5-iodo-2-oxo-1,2-dihydro-3H-indol-3-ylidene)acetohydrazide 4-({2-[2-(5-iodo-2-oxo-1,2-dihydro-3H-indol-3-ylidene)hydrazino]-2-oxoethyl}thio)-3-nitrobenzenesulfonamide N-(4-{[2-(5-iodo-2-oxo-1,2-dihydro-3H-indol-3-ylidene)hydrazino]carbonyl}phenyl)-N-methyl-3-phenylpropanamide methyl {3-[(4-{[3-(1,3-benzodioxol-5-yl)propanoyl]amino}benzoyl)hydrazono]-5-iodo-2-oxo-2,3-dihydro-1H-indol-1-yl}acetate methyl 4-[(4-{[2-(5-iodo-2-oxo-1,2-dihydro-3H-indol-3-ylidene)hydrazino]carbonyl}-phenyl)amino]-4-oxobutanoate 3-(1,3-benzodioxol-5-yl)-N-(4-{[2-(5-bromo-2-oxo-1,2-dihydro-3H-indol-3-ylidene)-hydrazino]carbonyl}phenyl)propanamide {3-[(4-{[3-(1,3-benzodioxol-5-yl)propanoyl]amino}benzoyl)hydrazono]-5-iodo-2oxo-2,3-dihydro-1H-indol-1-yl}acetic acid {3-[(4-{[3-(1,3-benzodioxol-5-yl)propanoyl]amino}benzoyl)hydrazono]-5-iodo-2-oxo-2,3-dihydro-1H-indol-1-yl}acetic acid, N-methyl-D-glucamine (1-deoxy-1-(methylamino)glucitol) salt methyl 6-[(4-{[2-(5-iodo-2-oxo-1,2-dihydro-3H-indol-3-ylidene)hydrazino]carbonyl}-phenyl)amino]-6-oxohexanoate methyl 4-{[(4-{[2-(5-iodo-2-oxo-1,2-dihydro-3H-indol-3-ylidene)hydrazino]carbonyl}-phenyl)amino]carbonyl}benzoate methyl 8-[(4-{[2-(5-iodo-2-oxo-1,2-dihydro-3H-indol-3-ylidene)hydrazino]carbonyl}-phenyl)amino]-8-oxooctanoate methyl 5-[(4-{[2-(5-iodo-2-oxo-1,2-dihydro-3H-indol-3-ylidene)hydrazino]carbonyl}-phenyl)amino]-5-oxopentanoate 8-[(4-{[2-(5-iodo-2-oxo-1,2-dihydro-3H-indol-3-ylidene)hydrazino]carbonyl}phenyl)-amino]-8-oxooctanoic acid 8-[(4-{[2-(5-iodo-2-oxo-1,2-dihydro-3H-indol-3-ylidene)hydrazino]carbonyl}phenyl)-amino]-8-oxooctanoic acid, N-methyl-D-glucamine (1-deoxy-1-(methylamino)glucitol) salt 6-[(4-{[2-(5-iodo-2-oxo-1,2-dihydro-3H-indol-3-ylidene)hydrazino]carbonyl}phenyl)-amino]-6-oxohexanoic acid 6-[(4-{[2-(5-iodo-2-oxo-1,2-dihydro-3H-indol-3-ylidene)hydrazino]carbonyl}phenyl)-amino]-6-oxohexanoic acid, N-methyl-D-glucamine (1-deoxy-1-(methylamino)glucitol) salt 4-[(4-{[2-(5-iodo-2-oxo-1,2-dihydro-3H-indol-3-ylidene)hydrazino]carbonyl}phenyl)-amino]-4-oxobutanoic acid 4-[(4-{[2-(5-iodo-2-oxo-1,2-dihydro-3H-indol-3-ylidene)hydrazino]carbonyl}phenyl)-amino]-4-oxobutanoic acid, N-methyl-D-glucamine (1-deoxy-1-(methylamino)glucitol) salt 5-[(4-{[2-(5-iodo-2-oxo-1,2-dihydro-3H-indol-3-ylidene)hydrazino]carbonyl}phenyl)-amino]-5-oxopentanoic acid 5-[(4-{[2-(5-iodo-2-oxo-1,2-dihydro-3H-indol-3-ylidene)hydrazino]carbonyl}phenyl)-amino]-5-oxopentanoic acid N-methyl-D-glucamine (1-deoxy-1-(methylamino)glucitol) salt 4-{[(4-{[2-(5-iodo-2-oxo-1,2-dihydro-3H-indol-3-ylidene)hydrazino]carbonyl}phenyl)-amino]carbonyl}benzoic acid 4-{[(4-{[2-(5-iodo-2-oxo-1,2-dihydro-3H-indol-3-ylidene)hydrazino]carbonyl}phenyl)-amino]carbonyl}benzoic acid, N-methyl-D-glucamine (1-deoxy-1-(methylamino)-glucitol) salt methyl 4-{[(4-{[2-(5-iodo-2-oxo-1,2-dihydro-3H-indol-3-ylidene)hydrazino]carbonyl}-benzyl)amino]carbonyl}benzoate 4-{[(4-{[2-(5-iodo-2-oxo-1,2-dihydro-3H-indol-3-ylidene)hydrazino]carbonyl}benzyl)-amino]carbonyl}benzoic acid 4-{[(4-{[2-(5-iodo-2-oxo-1,2-dihydro-3H-indol-3-ylidene)hydrazino]carbonyl}benzyl)-amino]carbonyl}benzoic acid, N-methyl-D-glucamine (1-deoxy-1-(methylamino)glucitol) salt benzyl (2S)-2-(4-{[2-(5-iodo-2-oxo-1,2-dihydro-3H-indol-3-ylidene)hydrazino]-carbonyl}phenoxy)-3-phenylpropanoate (2S)-2-(4-{[2-(5-iodo-2-oxo-1,2-dihydro-3H-indol-3-ylidene)hydrazino]carbonyl}-phenoxy)-3-phenylpropanoic acid (2S)-2-(4-{[2-(5-iodo-2-oxo-1,2-dihydro-3H-indol-3-ylidene)hydrazino]carbonyl}-phenoxy)-3-phenylpropanoic acid, N-methyl-D-glucamine (1-deoxy-1-(methylamino)glucitol) salt methyl 4-{3-[(4-{[3-(1,3-benzodioxol-5-yl)propanoyl]amino}benzoyl)hydrazono]-5-iodo-2-oxo-2,3-dihydro-1H-indol-1-yl}butanoate 4-{3-[(4-{[3-(1,3-benzodioxol-5-yl)propanoyl]amino}benzoyl)hydrazono]-5-iodo-2-oxo-2,3-dihydro-1H-indol-1-yl}butanoic acid 4-{3-[(4-{[3-(1,3-benzodioxol-5-yl)propanoyl]amino}benzoyl)hydrazono]-5-iodo-2-oxo-2,3-dihydro-1H-indol-1-yl}butanoic acid, N-methyl-D-glucamine (1-deoxy-1-(methylamino)glucitol) salt methyl 3-(4-{[(4-{[2-(5-iodo-2-oxo-1,2-dihydro-3H-indol-3-ylidene)hydrazino]carbonyl}phenyl)amino]sulfonyl}phenyl)propanoate 3-(4-{[(4-{[2-(5-iodo-2-oxo-1,2-dihydro-3H-indol-3-ylidene)hydrazino]carbonyl}-phenyl)amino]sulfonyl}phenyl) propanoic acid 3-(4-{[(4-{[2-(5-iodo-2-oxo-1,2-dihydro-3H-indol-3-ylidene)hydrazino]carbonyl}-phenyl)amino]sulfonyl}phenyl) propanoic acid, N-methyl-D-glucamine (1-deoxy-1-(methylamino)glucitol) salt N'-(5-Bromo-2-oxo-1,2-dihydro-3H-indol-3-ylidene)-4-(1H-tetrazol-5-yl)benzohydrazide A further aspect of the present invention is related to the use of oxindole hydrazide derivatives according to formula II as a medicament in particular for the preparation of pharmaceutical compositions for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS).

Specific compounds according to formula (II) are suitable for the modulation of the activity of PTPs, in particular of PTP1B, TC-PTP, SHP and GLEPP-1. It is assumed that the compounds of the present invention are therefore useful for the treatment and/or prevention of disorders which are mediated by PTPs, in particular of PTP1B, TC-PTP, SHP and GLEPP-1. Said treatment involves the modulation—notably the down regulation or the inhibition—of PTPs, particularly of PTP1B, TC-PTP, SHP and GLEPP-1 and more particularly PTP1B.

More specifically, the compounds of the present invention according to formula (II) are particularly useful for the treatment and/or prevention of diabetes II.

The oxindole hydrazide derivatives exemplified in this invention may be prepared from readily available starting materials using the following general methods and procedures. It will be appreciated that where typical or other experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

In general, the oxindole hydrazide derivatives according to formula (I) of this invention may be prepared from readily available starting materials. If such starting materials is not commercially available, it may be prepared by standard synthetic techniques. The following general methods and procedures described hereinafter in the Examples may be employed to prepare compounds of formula (I).

It will be appreciated that where typical or specific experimental conditions (i.e. reaction temperatures, time, moles of reagents, solvents, etc.) are given, other experimental conditions can also be used unless otherwise stated. Optimum reaction conditions may vary with the particular reactants or solvent used, but such conditions can be determined by a person skilled in the art by routine optimisation procedures.

Generally, oxindole hydrazide derivatives according to formula (I) may be obtained by reacting an isatine derivative of formula (A) with a hydrazide of formula (B) in acetic acid, optionally being in solution with a suitable alcohol such as ethanol or methanol, for several hours, e.g. from 2 to 24 hours as outlined in Scheme 1. Specific conditions involve the heating of the isatine of formula (A) with a hydrazide of formula (B) in acetic acid or in ethanol containing 2% acetic acid between 80 and 120° C. for 2 hours. The oxindole hydrazide derivatives of formula (I) could be obtained by deprotection of any of its protected form, e.g. a protected form of the acid (such as a benzylester) according to procedures known by a person skilled in the art. For all the protection, deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", 3$^{rd}$ edition, John Wiley & Sons Inc., 1999 (NY).

Scheme 1:

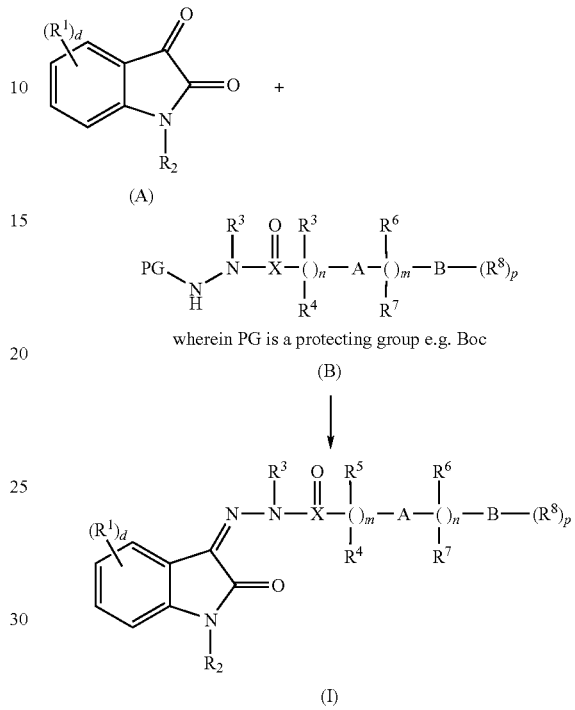

The method of preparation of the oxindole hydrazide compounds of formula (I) according to the above protocol has the specific advantage of being convenient and economic in the sense that it involves only a few chemical steps and typically involves small amounts of cheap solvents. In addition this method of preparation usually does not require any further step of purification.

Specific conditions involve the heating of the isatine of formula (A) with a protected hydrazide of formula (I) in acetic acid at 100° C. for a few hours in the presence of TFA.

Another protection of hydrazide of formula (B) is PG being Boc. Thus protected hydrazide of formula (B) can include highly substituted $R^8$ and the formation of compounds of formula (I) can be obtained in a "one-step" protocol.

The compounds of the present invention are those of formula (I) and/or its isomers such as (I') and/or tautomers such as of formula (I").

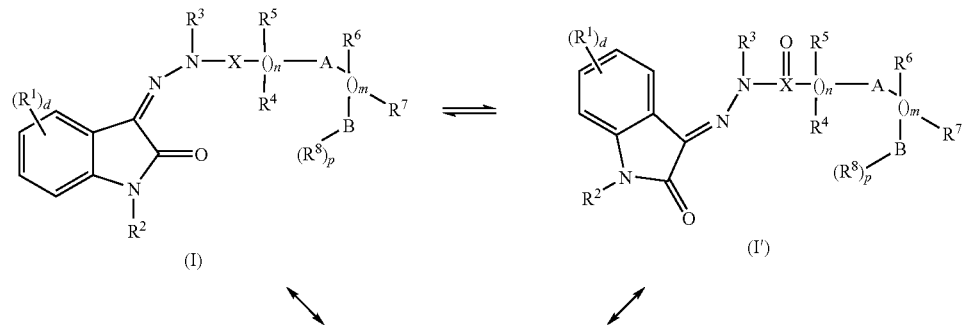

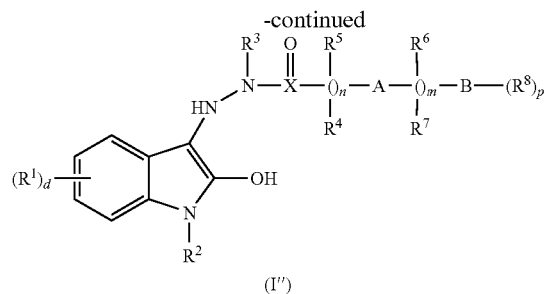

(I″)

Compounds of formula (A) and (B) are either commercially available compounds or may be prepared by standard synthetic techniques as hereinafter described in the Examples.

Specific compounds of formula (B) where X is carbon, can be obtained from the treatment of hydrazine and the ester derivative (C) in an appropriate solvent such as an alcohol, e.g. methanol, for a 2-15 hours, as outlined in Scheme 2. Typically, aromatic ester derivatives of formula (C) require about 15 hours at reflux in a suitable solvent such as ethanol. Aliphatic ester derivatives of formula (C) require a longer time of reaction at rt. Specifically activated ester derivatives, such as ester derivatives of formula (C) bearing a —$CH_2$—(O) spacer between the ester and central aromatic (A), usually require a shorter time of reaction at rt in a suitable solvent such as methanol. Compounds of formula (C) are either commercially available or may be prepared by standard synthetic techniques as hereinafter described.

The preparation of compound of formula (B) either follow the description of Scheme 2 or was achieved by standard synthetic techniques as described carefully hereinafter in the following Examples.

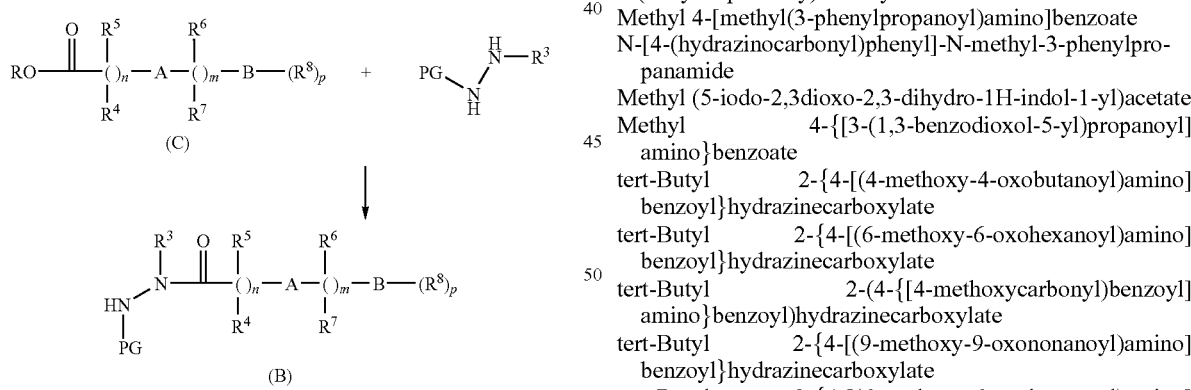

wherein R is a $C_1$-$C_6$ alkyl

Novel intermediate compounds of formula (B) are selected from the group consisting of:
N-[4-(Hydrazinocarbonyl)phenyl]-3-phenylpropanamide
Phenylmethyl-4-[(N-aminocarbamoyl)methoxy]benzoate
N-[4-(Hydrazinocarbonyl)phenyl]-2-furamide
N-[4-(Hydrazinocarbonyl)phenyl]hexanamide
4-Cyano-N-[4-(hydrazinocarbonyl)phenyl]benzamide
4-(Hexyloxy)-N-[4-(hydrazinocarbonyl)phenyl]benzamide
4-Heptyl-N-[4-(hydrazinocarbonyl)phenyl]benzamide
4-(2-Hydrazino-2-oxoethoxy)benzoic acid
4-Cyano-N-[3-(hydrazinocarbonyl)phenyl]benzamide
4-(Hydrazinocarbonyl-N-(3-[(trifluoromethyl)sulfonyl]phenyl)benzamide
4-Chloro-N-[4-(hydrazinocarbonyl)benzyl]benzamide
1-Benzoyl-4-piperidinecarbohydrazide
N-[4-(Hydrazinocarbonyl)phenyl]-2-phenoxyacetamide
N-[4-(Hydrazinocarbonyl)benzyl]-3-nitrobenzamide
N-[4-(Hydrazinocarbonyl)phenyl][1,1′-biphenyl]-4-carboxamide
3-(1,3-Benzodioxol-5-yl)-N-[4-(hydrazinocarbonyl)phenyl]propanamide
4-{[4-(Hydrazinocarbonyl)benzoyl]amino}benzoic acid
3-(3,4-Dihydroxyphenyl)-N-[4-(hydrazinocarbonyl)phenyl]propanamide
N-[4-(Hydrazinocarbonyl)phenyl]-3-(3-hydroxyphenyl)propanamide
N-[4-(Hydrazinocarbonyl)phenyl]-2-phenoxyacetamide
N-[4-(Hydrazinocarbonyl)benzyl]-3-nitrobenzamide
Methyl 3-(2-hydrazino-2-oxoethoxy)benzoate
2-[4-(1H-Tetrazol-5-yl)phenoxy]acetohydrazide
4-(Hydrazinocarbonyl)-N-phenylbenzamide
4-[4-(Morpholinylmethyl)phenoxy]benzohydrazide
4-(2-Hydrazinocarbonyl-ethyl)-benzoic acid methyl ester
2-[4-(1H-Tetrazol-5-yl)phenoxy]acetohydrazide
2-(4-Cyanophenoxy)acetohydrazide
Methyl 4-[methyl(3-phenylpropanoyl)amino]benzoate
N-[4-(hydrazinocarbonyl)phenyl]-N-methyl-3-phenylpropanamide
Methyl (5-iodo-2,3dioxo-2,3-dihydro-1H-indol-1-yl)acetate
Methyl 4-{[3-(1,3-benzodioxol-5-yl)propanoyl]amino}benzoate
tert-Butyl 2-{4-[(4-methoxy-4-oxobutanoyl)amino]benzoyl}hydrazinecarboxylate
tert-Butyl 2-{4-[(6-methoxy-6-oxohexanoyl)amino]benzoyl}hydrazinecarboxylate
tert-Butyl 2-(4-{[4-methoxycarbonyl)benzoyl]amino}benzoyl)hydrazinecarboxylate
tert-Butyl 2-{4-[(9-methoxy-9-oxononanoyl)amino]benzoyl}hydrazinecarboxylate
tert-Butyl 2-{4-[(6-methoxy-6-oxohexanoyl)amino]benzoyl}hydrazinecarboxylate
4-({[4-(Methoxycarbonyl)benzoyl]amino}methyl)benzoic acid
tert-Butyl 2-[4-({[4-(methoxycarbonyl)benzoyl]amino}methyl)benzoyl]hydrazinecarboxylate
tert-Butyl 2-(4-hydroxybenzoyl)hydrazinecarboxylate
tert-Butyl 2-{4-[(1S)-1-benzyl-2-(benzyloxy)-2-oxoethoxy]benzoyl}hydrazinecarboxylate
Methyl 4-(5-iodo-2,3-dioxo-2,3-dihydro-1H-indol-1-yl)butanoate
tert-Butyl 2-[4-({[4-(3-methoxy-3-oxopropyl)phenyl]sulfonyl}amino)benzoyl]hydrazinecarboxylate If the above set out general synthetic methods are not applicable for the obtention of compounds of formula I, suitable methods of preparation known by a person skilled in the art should be used.

When employed as pharmaceuticals, the oxindole hydrazide derivatives of the present invention are typically administered in the form of a pharmaceutical composition. Hence, pharmaceutical compositions comprising a compound of formula (I), (Ia), (II) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds of formula (II) for use as a medicament. The invention provides compounds of formula (I), (Ia), (I) for use as PTP inhibitors, for the treatment or prevention of disorders mediated by PTs, in particular of PTP1B, TC-PTP, SHP and GLEPP-1 in mammals, notably of humans, either alone or in combination with other medicaments, e.g. in combination with a further inhibitor of PTPs. Specifically, the oxindole hydrazide derivatives of the invention are useful in the treatment and/or prevention of metabolic disorders mediated by insulin resistance or hyperglycemia, comprising diabetes type I and/or II, obesity, polycystic ovary syndrome (PCOS). Said compounds are particularyl useful in the treatment of diabete type II.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the oxindole hydrazide derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral adminis-tration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the oxindole hydrazide derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the oxindole hydrazide derivatives of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences, 20<sup>th</sup> Edition*, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: min (minute), h (hour), g (gram), mg (milligram), mmol (millimole), m.p. (melting point), eq (equivalents), mL (milliliter), μL (microliters), mL (milliliters), ACN (Acetonitrile), DBU (Diazabicyclo [5.4.0]undec-7-ene), DIEA (Diisopropylethylamine), $CDCl_3$ (deuterated chloroform), cHex (Cyclohexanes), DCM (Dichloromethane), DIC (Diisopropyl carbodiimide), DMAP (4-Dimethylaminopyridine), $Pd(PPh_3)_4$ (Tetrakis triphenylphosphine palladium), DMF (Dimethylformamide), DMSO (Dimethylsulfoxide), DMSO-$d_6$ (deuterated dimethylsulfoxide), EDC (1-(3-Dimethyl-amino-propyl)-3-ethylcarbodiimide), EtOAc (ethyl acetate), $Et_2O$ (Diethyl ether), EtOH (Ethanol), HOBt (1-Hydroxybenzotriazole), $K_2CO_3$ (potassium carbonate), NaH (Sodium hydride), $NaHCO_3$ (Sodium bicarbonate), nBuLi (n-Butyl-lithium), TEA (Triethylamine), TFA (Trifluoroacetic acid), THF (Tetrahydrofuran), $MgSO_4$ (Magnesium sulfate), PetEther (Petroleum ether), rt (room temperature).

EXAMPLES

Example 1

N-(4-{[2-(5-Iodo-2-oxo-1,2-dihydro-3H-indol-3-ylidene)hydrazino]carbonyl}phenyl)-3-phenylpropanamide a) Preparation of methyl 4-[(3-phenylpropanoyl)amino]benzoate (Compound C of Scheme 2)

To a solution of methyl 4-aminobenzoate (825 mg, 5.46 mmol) in anhydrous pyridine (16 mL) was added dropwise hydrocinnamoyl chloride (990 μL) at 0° C. After 5 min, the temperature was allowed to warm up to rt. After 90 min aminomethyl resin (Polymers Laboratories PL-AMS, 1.93 mmol/g, 1200 mg) was added and the resulting mixture was stirred overnight at rt. After rinsing the resin and filtration, water (200 mL) was added to the filtrate and a white solid precipitated out. Filtration and washing with water gave a solid which was dried under vacuo at 60° C. overnight. The title compound (1.40 g) was obtained as a white solid (90%) in 98.2% purity by HPLC (MaxPlot detection between 230 and 400 nm).

$^1$H NMR (300 MHz, DMSO-$d_6$) δ 10.25 (s, 1H), 7.89 (d, J=8.9 Hz, 2H), 7.71 (d, J=8.9 Hz, 2H), 7.26 (m, 4H), 7.17 (m, 1H), 3.80 (s, 3H), 2.91 (t, J=7.6 Hz, 2H), 2.66 (t, J=7.6 Hz, 2H) M$^-$(APCI$^-$): 282.

b) Preparation of N-[4-(hydrazinocarbonyl)phenyl]-3-phenylpropanamide (Scheme 2, compound B)

To a suspension of methyl 4-[(3-phenylpropanoyl)amino]benzoate (1.40 g, 4.94 mmol) in EtOH (16 mL) was added hydrazine hydrate (3.6 mL). After stirring for 16 h at reflux, the reaction mixture was cooled to rt and a white solid precipitated out. Filtration, washing with water (4×5 mL) and drying under vacuo at 60° C. for 2 hrs gave 1.08 g of the title compound (77%) as a white solid in 99.1% puity by HPLC (MaxPlot detection between 230 and 400 nm).

$^1$H NMR (DMSO-$d_6$, 300 MHz) δ 10.06 (s, 1H), 9.56 (s, 1H), 7.71 (d, J=8.7 Hz, 2H), 7.57 (d, J=8.7 Hz, 2H), 7.21 (m, 4H), 7.12 (m, 1H), 4.37 (s, 2H), 2.85 (t, J=7.7 Hz, 2H), 2.59 (t, J=7.7 Hz, 2H).

c) Preparation of N-(4-{[2-(5-Iodo-2-oxo-1,2-dihydro-3H-indol-3-ylidene)hydrazino]carbonyl}phenyl)-3-phenylpropanamide Into a suspension of 5-iodo-1H-indole-2,3-dione in acetic acid was added N-[4-(hydrazinocarbonyl)phenyl]-3-phenylpropanamide (compound B). After stirring at 100° C., the reaction mixture was cooled to rt and a yellow solid precipitated out. Filtration on a fritté, washing with AcOH, water and drying under vacuo at 60° C. overnight gave 360 mg of the title compound (77%) as a yellow powder in 99.4% purity by HPLC ($R_t$: 4.68, gradient of 8 min, MaxPlot detection between 230 and 400 nm).

M.p. 297° C.

IR(neat) v 3165, 1661, 1521, 1500, 1269, 1141, 1122, 921 cm$^{-1}$.

$^1$H NMR (DMSO-$d_6$, 300 MHz) δ 13.81 (s, 1H), 11.45 (s, 1H), 10.32 (s, 1H), 7.82 (m, 5H), 7.71 (dd, J=8.3, 1.7 Hz, 1H), 7.27 (m, 4H), 7.17 (m, 1H), 6.81 (d, J=8.3 Hz, 2.92 (t, J=7.5 Hz,2H),2.68 (t, J=7.5 Hz, 2H).

M$^-$(ESI$^-$): 537, M$^+$(ESI$^+$): 539.

Analysis calculated for $C_{24}H_{19}IN_4O_3$.0.8 $H_2O$: C, 52.15; H, 3.76; N, 10.14%. Found: C, 52.12; H, 3.74; N, 10.08%.

Example 2

3,5-Dichloro-N'-(5-iodo-2-oxo-1,2-dihydro-3H-indol-3-ylidene) benzohydrazide

Following the general method as outlined in Example 1, into a suspension of 5-iodo-1H-indole-2,3-dione in acetic acid was added 3,5-dichlorobenzohydrazide. After stirring at 100° C., the reaction mixture was cooled to rt and a yellow solid precipitated out. Filtration on a fritté, washing with AcOH, water and drying under vacuo at 60° C. overnight gave 159 mg of the title compound (69%) as a orange solid in 90% purity by HPLC ($R_t$: 5.86, 6.66, gradient of 10 min, MaxPlot detection between 230 and 400 nm).

M.p. 337° C. (decomp).

$^1$H NMR (DMSO-$d_6$, 300 MHz) δ 13.69 (s, 0.4H), 11.89 (s, 0.6H), 11.48 (s, 0.4H); 10.93 (s, 0.6H), 8.33 (br, 0.6H), 7.97 (br s, 0.4H), 7.93-7.80 (m, 3H), 7.72 (br d, J=8.3 Hz, 1H), 6.81 (d, J=8.3 Hz, 0.4H), 6.75 (d, J=8.3 Hz, 0.6H).

M$^-$(APCI$^-$): 460.

Example 3

N'-(5-Iodo-2-oxo-1,2-dihydro-3H-indol-3-ylidene) benzohydrazide

Following the general method as outlined in Example 1, into a suspension of 5-iodo-1H-indole-2,3-dione in acetic acid was added benzohydrazide. After stirring at 100° C., the reaction mixture was cooled to rt and a yellow solid precipitated out. Filtration on a fritté, washing with AcOH, water and drying under vacuo at 60° C. overnight gave 129 mg of the title compound (66%) as a yellow solid in 99.8% purity by HPLC ($R_t$: 4.72, gradient of 10 min, MaxPlot detection between 230 and 400 nm).

M.p. 318° C.

IR (neat) v 3248, 1699, 1673, 1599, 1515, 1458, 1139, 913 cm$^{-1}$.

$^1$H NMR (DMSO-$d_6$, 300 MHz) δ 13.83 (s, 1H), 11.46 (s, 1H), 7.89 (m, 2H), 7.82 (br s, 1H), 7.69 (m, 2H), 7.61 (m, 2H), 6.81 (d, J=8.3 Hz, 1H).

M$^-$(APCI$^-$): 390; M$^+$(APCI$^+$): 392.

Analysis calculated for $C_{15}H_{10}IN_3O_2$.0.3 $H_2O$: C, 45.43; H, 2.69; N, 10.60%. Found: C, 45.21; H, 2.57; N, 10.51%.

Example 4

N'-(5-Iodo-2-oxo-1,2-dihydro-3H-indol-3-ylidene)-4-methylbenzohydrazide

Following the general method as outlined in Example 1, into a suspension of 5-iodo-1H-indole-2,3-dione in acetic acid was added 4-methylbenzohydrazide. After stirring at 100° C., the reaction mixture was cooled to rt and a yellow solid precipitated out. Filtration on a fritté, washing with AcOH, water and drying under vacuo at 60° C. overnight gave 163 mg of the title compound (80%) as a yellow solid in 99.99% purity by HPLC ($R_t$: 5.7, gradient of 10 min, MaxPlot detection between 230 and 400 nm).

M.p. 332° C. (decomp).

IR (neat) v 3218, 1674, 1611, 1459, 1268, 1134, 118, 916 cm$^{-1}$.

$^1$H NMR (DMSO-$d_6$, 300 MHz) δ 13.82 (s, 1H), 11.45 (s, 1H), 7.80 (m, 3H), 7.71 (dd, J=8.1, 1.7 Hz, 1H), 7.42 (d, J=7.9 Hz, 2H), 6.81 (d, J=8.3 Hz, 1H), 2.40 (s, 3H).

M$^-$(APCI$^-$): 404; M$^+$(APCI$^+$): 406.

Analysis calculated for $C_{16}H_{12}IN_3O_2$.0.2 $H_2O$: C, 47.01; H, 3.06; N, 10.28%. Found: C, 47.03; H, 2.98; N, 10.26%.

Example 5

4-Hydroxy-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 4-hydroxybenzohydrazide. After stirring at 100° C., the reaction mixture was cooled to rt and a yellow solid precipitated out. Filtration on a fritté, washing with AcOH, water and drying under vacuo at 60° C. overnight gave 174 mg of the title compound (85%) as a yellow solid in 99.8% purity by HPLC ($R_t$: 4.7, gradient of 10 min, MaxPlot detection between 230 and 400 nm).

M.p. 328° C. (decomp).

IR (neat) v 3139, 1655, 1601, 1538, 1505, 1141, 1114, 916 cm$^{-1}$.

$^1$H NMR (DMSO-d$_6$, 300 MHz) δ 13.77 (s, 1H), 11.43 (s, 1H), 10.42 (s, 1H), 7.81 (d, J=1.5 Hz, 1H), 7.76 (d, J=8.7 Hz, 2H), 7.69 (dd, J=8.3, 1.5 Hz, 1H), 6.94 (d, 8.7 Hz, 2H), 6.80 (d, J=8.3 Hz, 1H).

M$^-$(APCI$^-$): 406; M$^+$(APCI$^+$): 408.

Analysis calculated for $C_{15}H_{10}IN_3O_3$: C, 44.25; H, 2.48; N, 10.32%. Found: C, 44.12; H, 2.52; N, 10.24%.

Example 6

3-Hydroxy-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 3-hydroxybenzohydrazide. After stirring at 100° C., the reaction mixture was cooled to rt and a yellow solid precipitated out. Filtration on a fritté, washing with AcOH, water and drying under vacuo at 60° C. overnight gave 133 mg of the title compound (65%) as a yellow solid in 99.4% purity by HPLC ($R_t$: 4.83, gradient of 10 min, MaxPlot detection between 230 and 400 nm).

M.p. 343° C. (decomp).

IR (neat) v 3269, 3149, 3047, 1665, 1579, 1521, 1481, 1290, 1141, 849, 806 cm$^{-1}$.

$^1$H NMR (DMSO-d$_6$, 300 MHz) δ 13.78 (s, 1H), 11.45 (s, 1H), 9.99 (s, 1H), 7.82 (br s, 1H), 7.71 (dd, J=8.1, 1.5 Hz, 1H), 7.40 (m, 1H), 7.29 (m, 2H), 7.06 (m, 1H), 6.81 (d, J=8.1 Hz, 1H).

M$^-$(APCI$^-$): 406; M$^+$(APCI$^+$): 408.

Analysis calculated for $C_{15}H_{10}IN_3O_3$.0.2 H$_2$O: C, 43.86; H, 2.55; N, 10.23%. Found: C, 43.81; H, 2.48; N, 10.09%.

Example 7

2-nitro-N'-(5-iodo-2-oxo-1,2-dihydro-3H-indol-3-ylidene)benzohydrazide

Following the general method as outlined in Example 1, into a suspension of 5-iodo-1H-indole-2,3dione in acetic acid was added 2-nitrobenzohydrazide. After stirring at 100° C., the reaction mixture was cooled to rt and a yellow solid precipitated out. Filtration on a fritté, washing with AcOH, water and drying under vacuo at 60° C. overnight gave 159 mg of the title compound (73%) as a yellow solid in 99.2% purity by HPLC ($R_t$: 5.67, gradient of 10 min, MaxPlot detection between 230 and 400 nm).

M.p. 321° C. (decomp).

IR (neat) v 3166, 1679, 1519, 142, 1344, 1319 1151, 1127, 791 cm$^{-1}$.

M$^-$(APCI$^-$): 435; M$^+$(APCI$^+$): 437.

Analysis calculated for $C_{15}H_9IN_4O_4$.0.3 H$_2$O: C, 40.80; H, 2.19; N, 12.69%. Found: C, 40.80; H, 2.21; N, 12.63%.

Example 8

N'-(5-Iodo-2-oxo-1,2-dihydro-3H-indol-3-ylidene)-4-phenoxybenzohydrazide

Following the general method as outlined in Example 1, into a suspension of 5-iodo-1H-indole-2,3dione in acetic acid was added 4-phenoxybenzohydrazide. After stirring at 100° C., the reaction mixture was cooled to rt and a yellow solid precipitated out. Filtration on a fritté, washing with AcOH, water and drying under vacuo at 60° C. overnight gave 4940 mg of the title compound (93%) as a yellow solid in 99.9% purity by HPLC ($R_t$: 5.13, gradient of 8 min, MaxPlot detection between 230 and 400 nm).

M.p. 296° C.

IR (neat) v 3252, 1671, 1607, 1580, 1482, 1455, 1230, 1139, 756 cm$^{-1}$.

$^1$H NMR (DMSO-d$_6$, 300 MHz) δ 13.80 (s, 1H), 11.47 (s, 1H), 7.91 (m, 2H), 7.82 (d, J=1.5 Hz, 1H), 7.70 (dd, J=8.3, 1.5 Hz, 1H), 7.45 (m, 2H), 7.25 (m, 1H), 7.15 (m, 4H), 6.80 (d, J=8.3 Hz, 1H).

M$^-$(APCI$^-$): 482; M$^+$(APCI$^+$): 484.

Analysis calculated for $C_{21}H14IN_3O_3$.0.2 H$_2$O: C, 51.81; H, 2.98; N, 8.63%. Found: C, 51.77, H, 3.15; N, 8.65%.

Example 9

N'-(5-Iodo-2-oxo-1,2-dihydro-3H-indol-3-ylidene)-4-trifluoromethyl) benzohydrazide Following the general method as outlined in Example 1, into a suspension of 5-iodo-1H-indole-2,3one in acetic acid was added 4-(trifluoromethyl)benzohydrazide. After stirring at 100° C., the reaction mixture was cooled to rt and a yellow solid precipitated out. Filtration on a fritté, washing with AcOH, water and drying under vacuo at 60° C. overnight gave 151 mg of the title compound (66%) as a yellow solid in 99.9% purity by HPLC ($R_t$: 6.3, gradient of 10 min, MaxPlot detection between 230 and 400 nm).

M.p. 306° C. (decomp).

IR (neat) v 3238, 1703, 1674, 1460, 1326, 1108, 913 cm$^{-1}$.

$^1$H NMR (DMSO-d$_6$, 300 MHz) δ 13.83 (s, 1H), 11.48 (s, 1H), 8.08 (d, J=8.3 Hz, 2H), 7.99 (d, J=8.3 Hz, 2H), 7.82 (br s, 1H), 7.72 (br d, J=8.1 Hz, 1H), 6.80 (d, J=8.1 Hz, 1H).

M$^-$(APCI$^-$): 458; M$^+$(APCI$^+$): 460.

Analysis calculated for $C_{16}H_9F_3IN_3O_2$.0.5 H$_2$O: C, 41.05; H, 2.15; N, 8.98%. Found: C, 40.95; H, 2.02; N, 8.94%.

Example 10

4-tert-Butyl-N'-(5-iodo-2-oxo-1,2-dihydro-3H-indol-3-ylidene) benzohydrazide

Following the general method as outlined in Example 1, into a suspension of 5-iodo-1H-indole-2,3-dione in acetic acid was added 4-tert-butylbenzohydrazide. After stirring at 100° C., the reaction mixture was cooled to rt and a yellow solid precipitated out. Filtration on a fritté, washing with AcOH, water and drying under vacuo at 60° C. overnight gave 168 mg of the title compound (75%) as a yellow solid in 99.8% purity by HPLC ($R_t$: 6.65, gradient of 10 min, MaxPlot detection between 230 and 400 nm).

M.p. 326° C. (decomp).

IR (neat) v 3216, 2961, 1704, 1668, 1609, 1458, 1269, 1207, 1123, 916 cm$^{-1}$.

$^1$H NMR (DMSO-d$_6$, 300 MHz) δ 13.82 (s, 1H), 11.46 (s, 1H), 7.83 (m, 3H), 7.70 (dd, J=8.1, 1.7 Hz, 1H), 7.63 (d, J=8.7 Hz, 2H), 6.80 (d, J=8.1 Hz, 1H), 1.32 (s, 9H).

M$^-$(APCI$^-$): 446; M$^+$(APCI$^+$): 448.

Analysis calculated for $C_{19}H_{18}IN_3O_2$.0.3 H$_2$O: C, 5.41; H, 4.14; N, 9.28%. Found: C, 5.28; H, 3.95; N, 9.25%.

Example 11

N'-(5-Iodo-2-oxo-1,2-dihydro-3H-indol-3-ylidene) [1,1'-biphenyl]-4-carbohydrazide Following the general method as outlined in Example 1, into a suspension of 5-iodo-1H-indole-2,3-dione in acetic acid was added (1,1'-biphenyl)-4-carbohydrazide. After stirring at 100° C., the reaction mixture was cooled to rt and a yellow solid precipitated out. Filtration on a fritté, washing with AcOH, water and drying under vacuo at 60° C. overnight gave 201 mg of the title compound (86%) as a yellow solid in 99.8% purity by HPLC ($R_t$: 6.49, gradient of 10 min, MaxPlot detection between 230 and 400 nm).

M.p. 337° C. (decomp).

IR (neat) v 3247, 1698, 1671, 1606, 1468,;1260, 1120, 915, 736 $cm^{-1}$.

$^1$H NMR (DMSO-$d_6$, 300 MHz) δ 13.89 (s, 1H), 11.47 (s, 1H), 7.98 (d, J=8.4 Hz, 2H), 7.91 (d, J=8.4 Hz, 2H), 7.83 (br s, 1H), 7.77 (d, J=7.2 Hz, 2H), 7.71 (dd, J=8.3, 1.5 Hz, 1H), 7.52 (m, 2H), 7.44 (m, 1H), 6.81 (d, J=8.3 Hz, 1H).

M$^-$(APCI$^-$): 466; M$^+$(APCI$^+$): 468.

Analysis calculated for $C_{21}H_{14}IN_3O_2$: C,53.98; H,3.02; N,8.99%. Found: C, 53.72; H, 2.99; N, 8.92%.

Example 12

4-Bromo-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 4-bromobenzohydrazide. After stirring at 100° C., the reaction mixture was cooled to rt and a yellow solid precipitated out. Filtration on a fritté, washing with AcOH, water and drying under vacuo at 60° C. overnight gave 193 mg of the title compound (82%) as a yellow solid in 99.6% purity by HPLC ($R_t$: 6.03, gradient of 10 min, MaxPlot detection between 230 and 400 nm).

M.p. 337° C. (decomp).

$^1$H NMR (DMSO-$d_4$, 300 MHz) δ 13.79 (s, 1H), 11.47 (s, 1H), 7.83 (m, 5H), 7.71 (dd, J=8.3, 1.7 Hz, 1H), 6.80 (d, J=8.3 Hz, 1H).

M$^-$(APCI$^-$): 470; M$^+$(APCI$^+$): 472.

Example 13

N'-(5-Iodo-2-oxo-1,2dihydro-3H-indol-3-ylidene)-3-nitrobenzohydrazide

Following the general method as outlined in Example 1, into a suspension of 5-iodo-1H-indole-2,3-dione in acetic acid was added 3-nitrobenzohydrazide. After stirring at 100° C., the reaction mixture was cooled to rt and a yellow solid precipitated out. Filtration on a fritté, washing with AcOH, water and drying under vacuo at 60° C. overnight gave 176 mg of the title compound (81%) as a orange solid in 98.4% purity by HPLC ($R_t$: 5.61, gradient of 10 min, MaxPlot detection between 230 and 400 nm).

M.p. 324° C. (decomp).

IR (neat) v 3162, 3078, 1682, 1526, 1354, 1155, 828 $cm^{-1}$.

M$^-$(APCI$^-$): 435.

Analysis calculated for $C_{15}H_9IN_4O_4$: C,41.31; H,2.08; N,12.85%. Found: C, 41.21; H, 2.16; N, 12.67%.

Example 14

N'-(5-Iodo-2-oxo-1,2-dihydro-3H-indol-3-ylidene)-4-methoxybenzohydrazide

Following the general method as outlined in Example 1, into a suspension of 5-iodo-1H-indole-2,3-dione in acetic acid was added 4-methoxybenzohydrazide. After stirring at 100° C., the reaction mixture was cooled to rt and a yellow solid precipitated out. Filtration on a fritté, washing with AcOH, water and drying under vacuo at 60° C. overnight gave,347 mg of the title compound (82%) as a yellow solid in 99.9% purity by HPLC ($R_t$: 5.44, gradient of 10 min, MaxPlot detection between 230 and 400 nm).

M.p. 300° C. (decomp).

IR (neat) v 3208, 1695, 1661, 1461, 1246, 1178, 1113, 1027, 914, 847, 815 $cm^{-1}$.

$^1$H NMR (DMSO-$d_6$, 300 MHz) δ 13.80 (s, 1H), 11.45 (s, 1H), 7.86 (d, J=8.9 Hz, 2H), 7.82 (d, J=1.7 Hz, 1H), 7.70 (dd, J=8.1, 1.7 Hz, 1H), 7.14 (d, J=8.9 Hz, 2H), 6.80 (d, J=8.1 Hz, 1H), 3.85 (s, 3H).

M$^-$(APCI$^-$): 420; M$^+$(APCI$^+$): 422.

Analysis calculated for $C_{16}H_{12}IN_3O_3$: C, 45.63; H, 2.87; N, 9.98%. Found: C, 45.49; H, 2.86; N, 9.92%.

Example 15

N'-(5-Iodo-2-oxo-1,2-dihydro-3H-indol-3-ylidene)-3-methoxybenzohydrazide

Following the general method as outlined in Example 1, into a suspension of 5-iodo-1H-indole-2,3-dione in acetic acid was added 3-methoxybenzohydrazide. After stirring at 100° C., the reaction mixture was cooled to rt and a yellow solid precipitated out. Filtration on a fritté, washing with AcOH, water and drying under vacuo at 60° C. overnight gave 345 mg of the title compound (82%) as a yellow solid in 99.7% purity by HPLC ($R_t$: 5.5, gradient of 10 min, MaxPlot detection between 230 and 400 nm).

M.p. 287° C.

IR (neat) v 3137, 1677, 1588, 1517, 1441, 1204, 1130, 837, 745 $cm^{-1}$.

$^1$H NMR (DMSO-$d_6$, 300 MHz) δ 13.82 (s, 1H), 11.45 (s, 1H), 7.83 (br s, 1H), 7.71 (dd, J=8.1, 1.7 Hz, 1H), 7.53 (m, 1H), 7.42 (m, 2H), 7.26 (m, 1H), 6.81 (d, J=8.1 Hz, 1H), 3.84 (s, 3H).

M$^-$(APCI$^-$): 420; M$^+$(APCI$^+$): 422.

Analysis calculated for $C_{16}H_{12}IN_3O_3.0.2 H_2O$: C,45.24; H,2.94; N,9.89%. Found: C, 45.19; H, 2.85; N, 9.86%.

Example 16

4-Amino-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 4-aminobenzohydrazide. After stirring at 100° C., the reaction mixture was cooled to rt and a yellow solid precipitated out. Filtration on a fritté, washing with AcOH, water and drying under vacuo at 60° C. overnight gave 395 mg of the title compound (97%) as a yellow solid in 99.2% purity by HPLC ($R_t$: 4.41, gradient of 10 min, MaxPlot detection between 230 and 400 nm).

M.p. 299° C. (decomp).

IR (neat) v 3452, 3350, 3091. 1695, 1598, 1495, 1149, 756 $cm^{-1}$.

$^1$H NMR (DMSO-$_6$, 300 MHz) δ 13.74 (s, 1H), 11.40 (s, 1H), 7.80 (d, J=1.7 Hz, 1H), 7.68 (dd, J=8.1, 1.7 Hz, 1H), 7.60 (d, J=8.7 Hz, 2H), 6.80 (d, J=8.1 Hz, 1H), 6.65 (d, J=8.7 Hz, 2H), 6.10 (s, 2H).

M$^-$(APCI$^-$): 405; M$^+$(APCI$^+$): 407.

Analysis calculated for $C_{15}H_{11}IN_4O_2.H_2O$: C,43.80; H,3.24; N,12.02%. Found: C, 43.67; H, 3.24; N, 11.95%.

Example 17

4-(Dimethylamino)-N'-(5-iodo-2-oxo-1,2-dihydro-3H-indol-3-ylidene)-benzohydrazide Following the general method as outlined in Example 1, into a suspension of 5-iodo-1H-indole-2,3-dione in acetic acid was added 4-(dimethylamino)benzohydrazide. After stirring at 100° C., the reaction mixture was cooled to rt and a yellow solid precipitated out.

Filtration on a fritté, washing with AcOH, water and drying under vacuo at 60° C. overnight gave 346 mg of the title compound (80%) as a orange solid in 99.5% purity by HPLC ($R_t$: 5.38, gradient of 10 min, MaxPlot detection between 230 and 400 nm).

M.p. 324° C.

IR (neat) v 3186, 1661, 1601, 1506, 1441, 1267, 1120, 755 cm$^{-1}$.

$^1$H NMR (DMSO-$_6$, 300 MHz) δ 13.80 (s, 1H), 11.41 (s, 1H), 7.81 (br s, 1H), 7.73 (d, J=9.0 Hz, 2H), 7.68 (br d, J=7.9 Hz, 1H), 6.82 (d, J=9.0 Hz, 2H), 6.80 (d, J=7.9 Hz, 1H), 3.02 (s, 6H).

M$^-$(APCI$^-$): 433.

Analysis calculated for $C_{17}H_{15}IN_4O_2$: C,47.02; H,3.48; N,12.90%. Found: C, 46.74; H, 3.46; N, 12.73%.

Example 18

N'-(5-Iodo-2-oxo-1,2 dihydro-3H-indol-3-ylidene)-2-(4-nitrophenoxy)acetohydrazide Following the general method as outlined in Example 1, into a suspension of 5-iodo-1H-indole-2,3-dione in acetic acid was added 2-(4-nitrophenoxy)acetohydrazide. After stirring at 100° C., the reaction mixture was cooled to rt and a yellow solid precipitated out. Filtration on a fritté, washing with AcOH, water and drying under vacuo at 60° C. overnight gave 395 mg of the title compound (85%) as a yellow solid in 97.3% purity by HPLC ($R_t$: 5.76, gradient of 10 min, MaxPlot detection between 230 and 400 nm).

M.p. 308° C. (decomp).

IR (neat) v 3172, 3071, 1693, 1594, 1491, 1340, 1264, 1118, 838 cm$^{-1}$.

$^1$H NMR (DMSO-$_6$, 300 MHz) δ 13.59 (br s, 0.5H), 12.49 (br s, 0.5H), 11.37 (s, 1H), 8.24 (m, 2H), 7.85 (m, 1H), 7.71 (dd, J=8.3, 1.9 Hz, 1H), 7.24 (m, 2H), 6.80 (d, J=8.3 Hz, 1H), 5.49 (br s, 1H), 5.09 (br s, 1H).

M$^-$(APCI$^-$): 465.

Analysis calculated for $C_{16}H_{11}IN_4O_5$: C,41.22; H,2.38; N,12.02%. Found: C, 41.04; H, 2.41; N, 11.85%.

Example 19

N'-(5-Iodo-2-oxo-1,2-dihydro-3H-indol-3-ylidene)-4-(trifluoromethoxy)-benzohydrazide Following the general method as outlined in Example 1, into a suspension of 5-iodo-1H-indole-2,3dione in acetic acid was added 4-(trifluoromethoxy)benzohydrazide. After stirring at 100° C., the reaction mixture was cooled to rt and a yellow solid precipitated out. Filtration on a fritté, washing with AcOH, water and drying under vacuo at 60° C. overnight gave 135 mg of the title compound (57%) as a yellow solid in 99.7% purity by HPLC ($R_t$: 6.39, gradient of 10 min, MaxPlot detection between 230 and 400 nm).

M.p. 306° C.

IR (neat) v 3285, 1707, 1672, 1605, 1496, 1461, 1248, 1599, 1141, 914 cm$^{-1}$.

$^1$H NMR (DMSO-d$_6$, 300 MHz) δ 13.79 (s, 1H), 11.47 (s, 1H), 8.01 (d, J=8.5 Hz, 2H), 7.81 (br s, 1H), 7.71 (dd, J=8.3, 1.9 Hz, 1H), 7.61 (d, J=8.5 Hz, 2H), 6.80 (d, J=8.3 Hz, 1H).

M$^-$(APCI$^-$): 474.

Analysis calculated for $C_{16}H_9F_3IN_3O_3$: C,40.44; H,1.91; N,8.84%. Found: C, 40.39; H, 2.12; N, 8.80%.

Example 20

N'-(5-Iodo-2-oxo-1,2-dihydro-3H-indol-3-ylidene)-2,1,3-benzoxadiazole-5-carbohydrazide Following the general method as outlined in Example 1, into a suspension of 5-iodo-1H-indole-2,3-dione in acetic acid was added 2,1,3-benzoxadiazole-5-carbohydrazide. After stirring at 100° C., the reaction mixture was cooled to rt and a yellow solid precipitated out. Filtration on a fritté, washing with AcOH, water and drying under vacuo at 60° C. overnight gave 166 mg of the title compound (77%) as a orange solid in 99.1% purity by HPLC ($R_t$: 5.65, gradient of 10 min, MaxPlot detection between 230 and 400 nm).

M.p. 348° C. (decomp).

IR (neat) v 3212, 1698, 1681, 1613, 1520, 1459, 1237, 1130, 881, 748 cm$^{-1}$.

M$^-$(APCI$^-$): 432.

Analysis calculated for $C_{15}H_8IN_5O_3 \cdot 0.35\ H_2O$: C,41.00; H,2.00; N,15.94%. Found: C, 41.00; H, 2.01; N, 15.80%.

Example 21

N'-(5-Iodo-2-oxo-1,2-dihydro-3H-indol-3-ylidene)-((5-nitro)-2-furohydrazide)

Following the general method as outlined in Example 1, into a suspension of 5-iodo-1H-indole-2,3-dione in acetic acid was added 5-nitro-2-furohydrazide. After stirring at 100° C., the reaction mixture was cooled to rt and a yellow solid precipitated out. Filtration on a fritté, washing with AcOH, water and drying under vacuo at 60° C. overnight gave 158 mg of the title compound (74%) as a Orange solid in 98.3% purity by HPLC ($R_t$: 5.31, gradient of 10 min, MaxPlot detection between 230 and 400 nm).

M.p. 351° C. (decomp).

IR (neat) v3131, 1678, 1538, 1256, 1145, 1026, 820cm$^{-1}$.

$^1$H NMR (DMSO-$_6$, 300 MHz) δ 13.86 (br s, 1H), 11.46 (s, 1H), 7.88 (br s, 1H), 7.84 (d, J=3.8 Hz, 7.73 (m, 2H), 6.81 (d, J=7.9 Hz, 1H).

M$^-$(APCI$^-$): 425.

Analysis calculated for $C_{13}H_7IN_4O_5$: C,36.64; H,1.66; N,13.15%. Found: C, 36.52; H, 1.87; N, 12.88%.

Example 22

Methyl 4-{[2-(5-iodo-2-oxo-1,2-dihydro-3H-indol-3-ylidene)hydrazino]-carbonyl}benzoate Following the general method as outlined in Example 1, into a suspension of 5-iodo-1H-indole-2,3-dione in acetic acid was added methyl 4-(hydrazinocarbonyl)benzoate. After stirring at 100° C., the reaction mixture was cooled to rt and a yellow solid precipitated out. Filtration on a fritté, washing with AcOH, water and drying under vacuo at 60° C. overnight gave 334 mg of the title compound (86%) as a yellow solid in 98.3% purity by HPLC ($R_t$: 5.21, gradient of 10 min, MaxPlot detection between 230 and 400 nm).

M.p. 342° C. (decomp).

IR (neat) v 3222, 1674, 1531, 1436, 1286, 1112, 917, 810 cm$^{-1}$.

$^1$H NMR (DMSO-d$_6$, 300 MHz) δ 13.84 (s, 1H), 11.47 (s, 1H), 8.16 (d, J=8.1 Hz, 2H), 8.01 (d, J=8.1 Hz, 2H), 7.82 (s, 1H), 7.72 (d, J=8.3 Hz, 1H), 6.81 (d, J=8.3 Hz, 1H), 3.90 (s, 3H).

M$^-$(APCI$^-$): 448.

Analysis calculated for C$_{17}$H$_{12}$IN$_3$O$_4$.0.5 H$_2$O: C,44.56; H,2.86; N,9.17%. Found: C, 44.47; H, 2.81; N, 9.16%.

Example 23

Methyl 4-{2-[2-(5-iodo-2-oxo-1,2-dihydro-3H-indol-3-ylidene)hydrazino]-2-oxoethoxy}benzoate Following the general method as outlined in Example 1, into a suspension of 5-iodo-1H-indole-2,3-dione in acetic acid was added methyl 4-(2-hydrazino-2-oxoethoxy)benzoate. After stirring at 100° C., the reaction mixture was cooled to rt and a yellow solid precipitated out. Filtration on a fritté, washing with AcOH, water and drying under vacuo at 60° C. overnight gave 185 mg of the title compound (77%) as a yellow solid in 99.1% purity by HPLC (R$_t$: 5.34, gradient of 10 min, MaxPlot detection between 230 and 400 nm).

M.p.288° C.

IR (neat) v 3307, 3208, 1698, 1605, 1503, 1428, 1168, 1114, 763 cm$^{-1}$.

$^1$H NMR (DMSO-d$_6$, 300 MHz) δ 13.61 (br s, 0.5H), 12.49 (br s, 0.5H), 11.35 (s, 1H), 7.94 (d, J=8.5 Hz, 2H), 7.83 (m, 1H), 7.70 (dd, J=8.1, 1.9 Hz, 1H), 7.13 (d, J=8.5 Hz, 2H), 6.79 (d, J=8.1 Hz, 1H), 5.40 (br s, 1H), 4.99 (br s, 1H), 3.81 (s, 3H).

M$^-$(APCI$^-$): 478.

Analysis calculated for C$_{18}$H$_{14}$IN$_3$O$_5$.0.4 H$_2$O: C,44.45; H,3.07; N,8.64%. Found: C, 44.46; H, 2.96; N, 8.68%.

Example 24

4-{[2-(5-Iodo-2-oxo-1,2-dihydro-3H-indol-3-ylidene)hydrazino]-carbonyl}benzoic acid Into a suspension of methyl 4-{[2-(5-iodo-2-oxo-1,2-dihydro-3H-indol-3-ylidene)hydrazino]carbonyl}benzoate (80 mg, 0.18 mmol) in THF (5 mL) was added NaOH (0.2 M, 2.5 mL). The resulting solution was stirred at rt for 5 hrs and quenched with HCl (1N, 2 mL) and water (5 mL). A yellow solid precipitated out. Filtration, washing with water (2×1 mL) and drying under vacuo at rt for 72 hrs to give the tilte compound as a yellow powder (58 mg, 75%) in 98.6% purity by HPLC (MaxPlot detection between 230 and 400 nm).

M.p. 370° C. (decomp).

$^1$H NMR (300 MHz, DMSO-d$_6$) δ 13.85 (s, 1H), 13.30 (s, 1H), 11.48 (s, 1H), 8.13 (d, J=7.9 Hz, 2H), 7.99 (d, J=7.9 Hz, 2H), 7.83 (s, 1H), 7.72 ((d, J=7.9 Hz, 1H), 6.81 (d, J=7.9 Hz, 1H).

M$^-$(APCI$^-$): 434. M$^+$(APCI$^+$): 436.

Example 25

4-Iodo-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 4-iodobenzohydrazide. After stirring at 100° C., the reaction mixture was cooled to rt and a yellow solid precipitated out. Filtration on a fritté, washing with AcOH, water and drying under vacuo at 60° C. overnight gave 430 mg of the title compound (83%) as a yellow solid in 98.7% purity by HPLC (R$_t$: 6.19, gradient of 10 min, MaxPlot detection between 230 and 400 nm).

M.p. 326° C.

IR (neat) v 3263, 1704, 1673, 1471, 1455, 1264, 1524, 884, 741 cm$^{-1}$.

$^1$H NMR (DMSO-$_6$, 300 MHz) δ 13.79 (s, 1H), 11.47 (s, 1H), 8.01 (d, J=8.5 Hz, 2H), 7.82 (br s, 1H), 7.71 (dd, J=8.3, 1.5 Hz, 1H), 7.65 (d, J=8.5 Hz, 2H), 6.80 (d, J=8.3 Hz, 1H).

M$^-$(APCI$^-$): 516; M$^+$(APCI$^+$): 518.

Analysis calculated for C$_{15}$H$_9$I$_2$N$_3$O$_2$: C,34.84; H,1.75; N,8.13%. Found: C, 34.88; H, 1.73; N, 8.18%.

Example 26

N'-(5-Iodo-2-oxo-1,2-dihydro-3H-indol-3-ylidene)-3-phenoxybenzohydrazide

Following the general method as outlined in Example 1, into a suspension of 5-iodo-1H-indole-2,3-dione in acetic acid was added 3-phenoxybenzohydrazide. After stirring at 100° C., the reaction mixture was cooled to rt and a yellow solid precipitated out. Filtration on a fritté, washing with AcOH, water and drying under vacuo at 60° C. overnight gave 403 mg of the title compound (83%) as a yellow solid in 99.5% purity by HPLC (R$_t$: 6.58, gradient of 10 min, MaxPlot detection between 230 and 400 nm).

M.p. 283° C.

IR (neat) v 3163, 1688, 1585, 1513, 1444, 1244, 1135, 1006, 738 cm$^{-1}$.

$^1$H NMR (DMSO-d$_6$, 300 MHz) δ 13.79(s, 1H), 11.46 (s, 1H), 7.81 (br s, 1H), 7.71 (dd, J=8.1, 1.7 Hz, 1H), 7.64 (m, 2H), 7.45 (m, 3H), 7.32 (m, 1H), 7.21 (t, J=7.5 Hz, 1H), 7.11 (d, J=7.5 Hz, 2H), 6.80 (d, J=8.1 Hz, 1H).

M$^-$(APCI$^-$): 482, M$^+$(APCI$^+$): 484.

Analysis calculated for C$_{21}$H$_{14}$IN$_3$O$_3$: C,52.19; H,2.92; N,8.69%. Found: C, 52.22; H, 2.97; N, 8.62%.

Example 27

N'-(5-Iodo-2-oxo-1,2dihydro-3H-indol-3-ylidene)-2-(4-iodophenoxy)-acetohydrazide Following the general method as outlined in Example 1, into a suspension of 5-iodo-1H-indole-2,3-dione in acetic acid was added 2-(4-iodophenoxy)acetohydrazide. After stirring at 100° C., the reaction mixture was cooled to rt and a yellow solid precipitated out. Filtration on a fritté, washing with AcOH, water and drying under vacuo at 60° C. overnight gave 173 mg of the title compound (79%) as a yellow solid in 96.4% purity by HPLC (R$_t$: 6.41, gradient of 10 min, MaxPlot detection between 230 and 400 nm).

M.p. 275° C.

M$^-$(APCI$^-$): 546; M$^+$(APCI$^+$): 548.

Example 28

N'-(5-Iodo-2-oxo-1,2-dihydro-3H-indol-3-ylidene)-2-[(4-methylphenyl)sulfonyl]acetohydrazide Following the general method as outlined in Example 1, into a suspension of 5-iodo-1H-indole-2,3-dione in acetic acid was added 2-[(4-methylphenyl)sulfonyl]acetohydrazide. After stirring at 100° C., the reaction mixture was cooled to rt and a yellow solid precipitated out. Filtration on a fritté, washing with AcOH, water and drying under vacuo at 60° C. overnight gave 199 mg of the title compound (82%) as a yellow solid in 91.1% purity by HPLC ($R_t$: 5.38, gradient of 10 min, MaxPlot detection between 230 and 400 nm).

M.p. 257° C.

$^1$H NMR (DMSO-d$_6$, 300 MHz) δ 12.98 (s, 0.33H), 12.41 (s, 0.67H), 11.32 (s, 1H), 7.78 (d, J=7.9 Hz, 2H), 7.69 (m, 2H), 7.45 (d, J=7.9 Hz, 0.67H), 7.30 (d, J=7.9 Hz, 1.33H), 6.76 (m, 1H), 4.96 (s, 1.33H), 4.83 (s, 0.67H), 2.40 (s, 1H), 2.17 (s, 2H).

M$^-$(APCI$^-$): 482; M$^+$(APCI$^+$): 484.

Example 29

2-{[(2-Furylmethyl)sulfonyl]methyl}-N'-(5-iodo-2-oxo-1,2-dihydro-3H-indol-3-ylidene)-1,3-thiazole-4-carbohydrazide Following the general method as outlined in Example 1, into a suspension of 5-iodo-1H-indole-2,3-dione in acetic acid was added 2-{[(2-furylmethyl)sulfonyl]methyl}-1,3-thiazole-4-carbohydrazide. After stirring at 100° C., the reaction mixture was cooled to rt and a yellow solid precipitated out. Filtration on a fritté, washing with AcOH, water and drying under vacuo at 60° C. overnight gave 32 mg of the title compound (63%) as a yellow solid in 99.3% purity by HPLC ($R_t$: 4.8, gradient of 10 min, MaxPlot detection between 230 and 400 nm).

M.p. 306° C. (decomp).

$^1$H NMR (DMSO-d$_6$, 300 MHz) δ 14.24 (s, 1H), 11.39 (s, 1H), 8.73 (s, 1H), 7.84 (br s, 1H), 7.74 (br s, 1H), 7.70 (dd, J=8.1, 1.5 Hz, 1H), 6.76 (d, J=8.1 Hz, 1H), 6.67 (d, J=3.0 Hz, 6.51 (m, 1H), 5.17 (s, 2H), 4.94 (s, 2H).

M$^-$(APCI$^-$): 555; M$^+$(APCI$^+$): 557.

Example 30

2-Hydroxy-N'-(-5-iodo-2-oxo-1,2-dihydro-3H-indol-3-ylidene)-benzohydrazide

Following the general method as outlined in Example 1, into a suspension of 5-iodo-1H-indole-2,3-dione in acetic acid was added 2-hydroxybenzohydrazide. After stirring at 100° C., the reaction mixture was cooled to rt and a yellow solid precipitated out. Filtration on a fritté, washing with AcOH, water and drying under vacuo at 60° C. overnight gave 344 mg of the title compound (84%) as a yellow solid in 98.5% purity by HPLC ($R_t$: 4.61, gradient of 10 min, MaxPlot detection between 230 and 400 nm).

M.p. 327° C. (decomp).

IR (neat) v 3298, 1704, 1646, 1610, 1530, 1444, 1294, 1202, 1121, 914, 743 cm$^{-1}$.

$^-$H NMR (DMSO-d$_6$, 300 MHz) δ 14.33 (s, 1H), 11.71 (s, 1H), 11.24 (s, 1H), 7.99,(d, J=7.2 Hz, 1H), 7.79 (br s, 1H), 7.68 (dd, J=8.1, 1.5 Hz, 1H), 7.45 (m, 1H), 6.99 (m, 2H), 6.77 (d, J=8.1 Hz, 1H).

M$^-$(APCI$^-$): 406.

Analysis calculated for $C_{15}H_{10}IN_3O_3$: C,44.25; H,2.48; N,10.32%. Found: C, 44.21; H, 2.66; N, 10.27%.

Example 31

N-(2-Furylmethyl)-N'-{2-[2-(5-iodo-2-oxo-1,2-dihydro-3H-indol-3-ylidene)hydrazino]-2-oxoethyl}urea Following the general method as outlined in Example 1, into a suspension of 5-iodo-1H-indole-2,3-dione in acetic acid was added N-(2-furylmethyl)-N'-(2-hydrazino-2-oxoethyl)urea. After stirring at 100° C., the reaction mixture was cooled to rt and a yellow solid precipitated out. Filtration on a fritté, washing with AcOH, water and drying under vacuo at 60° C. overnight gave 71 mg of the title compound (71%) as a yellow solid in 95.6% purity by HPLC ($R_t$: 4.26, gradient of 10 min, MaxPlot detection between 230 and 400 nm).

M.p. 257° C. (decomp).

$^1$H NMR (DMSO-d$_6$, 300 MHz) δ 13.20 (br s, 0.5H), 12.42 (br s, 0.5H), 11.33 (s, 1H), 7.81 (s, 1H), 7.69 (d, J=7.9 Hz, 1H), 7.55 (s, 1H), 6.78 (d, J=7.9 Hz, 1H), 6.71 (br s, 1H), 6.53 (br s, 1H), 6.36 (s, 1H), 6.22 (s, 1H), 4.32 (br s, 1H), 4.21 (s, 2H), 3.89 (br s, 1H).

M$^-$(APCI$^-$): 466; M$^+$(APCI$^+$): 468.

Example 32

N'-(5-Iodo-2oxo-1,2-dihydro-3H-indol-3-ylidene)-4-(methylsulfanyl)-benzohydrazide Following the general method as outlined in Example 1, into a suspension of 5-iodo-1H-indole-2,3-dione in acetic acid was added 4-(methylsulfanyl)benzohydrazide. After stirring at 100° C., the reaction mixture was cooled to rt and a yellow solid precipitated out. Filtration on a fritté, washing with AcOH, water and drying under vacuo at 60° C. overnight gave 411 mg of the title compound (94%) as a yellow solid in 99.3% purity by HPLC ($R_t$: 5.75, gradient of 10 min, MaxPlot detection between 230 and 400 nm).

M.p. 298° C.

M$^-$(APCI$^-$): 436; M$^+$(APCI$^+$): 438.

Example 33

Methyl 6-{[2-(5-iodo-2-oxo-1,2-dihydro-3H-indol-3-ylidene)hydrazino]-carbonyl}nicotinate Following the general method as outlined in Example 1, into a suspension of 5-iodo-1H-indole-2,3-dione in acetic acid was added methyl 6-(hydrazinocarbonyl)nicotinate. After stirring at 100° C., the reaction mixture was cooled to rt and a yellow solid precipitated out. Filtration on a fritté, washing with AcOH, water and drying under vacuo at 60° C. overnight gave 33 mg of the title compound (73%) as a yellow solid in 89.7% purity by HPLC ($R_t$: 4.44, gradient of 8 min, MaxPlot detection between 230 and 400 nm).

M.p. 349° C. (decomp).

M$^-$(APCI$^-$): 449; M$^+$(APCI$^+$): 451.

Example 34

Benzyl 4-{2-[2-(5-iodo-2-oxo-1,2-dihydro-3H-indol-3-ylidene)hydrazino]-2-oxoethoxy}benzoate a) Preparation of benzyl 4-(2-hydrazino-2-oxoethoxy)benzoate (Scheme 2, compound B)

To a suspension of benzyl 4-(2-methoxy-2-oxoethoxy) benzoate (1.0 g, 3.33 mmol) in MeOH (15 mL) was added hydrazine hydrate (1.7 mL). After stirring for 1 h at rt, the reaction mixture was filtered. The cake was washed with MeOH (3×4 mL) and dryed under vacuo at 50° C. overnight gave 936 mg of the title compound (94%) as a white solid in 99.7% purity by HPLC (MaxPlot detection between 230 and 400 nm).

$^1$H NMR (DMSO-d$_6$, 300 MHz) δ 9.40 (s, 1H), 7.94 (d, J=8.8 Hz, 2H), 7.46-7.31 (m, 5H), 7.06 (d, J=8.8 Hz, 2H), 5.31 (s, 2H), 4.57 (s, 2H), 4.34 (s, 2H).

b) Preparation of benzyl 4-{2-[2-(5-iodo-2-oxo-1,2-dihydro-3H-indol-3-ylidene)-hydrazino]-2-oxoethoxy}benzoate Following the general method as outlined in Example 1, into a suspension of 5-iodo-1H-indole-2,3-dione in acetic acid was added benzyl 4-(2-hydrazino-2-oxoethoxy)benzoate. After stirring at 100° C. the reaction mixture was cooled to rt and a yellow solid precipitated out. Filtration on a fritté, washing with AcOH, water and drying under vacuo at 60° C. overnight gave 215 mg of the title compound (77%) as a orange powder in 98.3% purity by HPLC ($R_t$: 5.16, gradient of 8 min, MaxPlot detection between 230 and 400 nm).

M.p. 221° C.

IR (neat) v 3223, 1698, 1606, 1506, 1288, 1243, 1167, 1127, 765 cm$^{-1}$.

$^1$H NMR (DMSO-d$_6$, 300 MHz) δ 13.62 (s, 0.6H), 12.47 (s, 0.4H), 11.36 (s, 1H), 7.97 (d, J=8.3 Hz, 2H), 7.82 (br s, 1H), 7.70 (dd, J=8.3, 1.9 Hz, 1H), 7.47-7.41 (m, 5H), 7.14 (d, J=8.3 Hz, 2H), 6.79 (d, J=8.3 Hz, 1H), 5.41 (br s, 0.8H), 5.32 (s, 2H), 4.98 (br s, 1.2H).

M$^-$(ESI$^-$): 554; M$^+$(ESI$^+$): 556.

Example 35

N-4-{[2-(5-Iodo-2-oxo-1,2-dihydro-3H-indol-3-ylidene)hydrazino]-carbonyl}phenyl)-2-furamide a) Preparation of N-[4-hydrazinocarbonyl)phenyl]-2-furamide (Scheme 2, compound B)

To a suspension of methyl 4-(2-furoylamino)benzoate (483 mg, 1.97 mmol) in EtOH (6 mL) was added hydrazine hydrate (1.5 mL). After stirring for 15 h at reflux, the reaction mixture was cooled to rt and a white solid precipitated out. Filtration, washing with EtOH (2 mL) and water (2×2 mL), and drying under vacuo at rt for 72 hrs gave 242 mg of the title compound (50%) as a white solid in 99.5% purity by HPLC (MaxPlot detection between 230 and 400 nm).

$^1$H NMR (DMSO-d$_6$, 300 MHz) δ 10.36 (s, 1H), 9.65 (s, 1H), 7.95 (br s, 1H), 7.80 (s, 4H), 7.36 (d, J=3.4 Hz, 1H), 6.71 (dd, J=3.4, 1.5 Hz, 1H), 4.43 (s, 2H).

b) Preparation of N-(4-{[2-(5-Iodo-2-oxo-1,2-dihydro-3H-indol-3-ylidene)hydrazino]-carbonyl}phenyl)-2-furamide Following the general method as outlined in Example 1, into a suspension of 5-iodo-1H-indole-2,3-dione in acetic acid was added N-[4-(hydrazinocarbonyl)phenyl]-2-furamide. After stirring at 100° C. the reaction mixture was cooled to rt and a yellow solid precipitated out. Filtration on a fritté, washing with AcOH, water and drying under vacuo at 60° C. overnight gave 81 mg of the title compound (81%) as a yellow powder in 96.7% purity by HPLC ($R_t$: 4.05, gradient of 8 min, MaxPlot detection between 230 and 400 nm).

M.p. 343° C. (decomp.).

$^1$H NMR (DMSO-d$_6$, 300 MHz) δ 13.83 (s, 1H), 11.46 (s, 1H), 10.55 (s, 1H), 8.00 (m, 3H), 7.89 (d, J=9.0 Hz, 2H), 7.83 (d, J=1.7 Hz, 1H), 7.71 (dd, J=8.1, 1.7 Hz, 1H), 7.41 (d, J=3.4 Hz, 1H), 6.81 (d, J=8.1 Hz, 1H), 6.73 (dd, J=3.4, 1.8 Hz, 1H).

M$^-$(APCI$^-$): 499; M$^+$(APCI$^+$): 501.

Example 36

N-(4-{[2-(5-Iodo-2-oxo-1,2-dihydro-3H-indol-3-ylidene)hydrazino]carbonyl}phenyl)hexanamide a) Preparation of methyl 4-(hexanoylamino)benzoate (Compound C of Scheme 2)

To a solution of methyl 4-aminobenzoate (500 mg, 3.31 mmol) in anhydrous pyridine (10 mL) was added dropwise hexanoyl chloride (550 μl) at 0° C. After 5 min the temperature was allowed to warm up to rt. After 90 min aminomethyl resin (Polymers Laboratories PL-AMS, 1.93 mmol/g, 720 mg) was added and the resulting mixture was stirred overnight at rt. After filtration and rinsing the resin, water (125 mL) was added to the filtrate and a white solid precipated out. Filtration and washing with water gave a solid which was dried under vacuo at 60° C. overnight. The title compound (699 mg) was obtained as a white solid (85%) in 96.9% purity by HPLC (MaxPlot detection between 230 and 400 mn).

$^1$H NMR (300 MHz, DMSO-d$_6$) δ 10.20 (s, 1H), 7.89 (d, J=8.7 Hz, 2H), 7.72 (d, J=8.7 Hz, 2H), 3.80 (s, 3H), 2.32 (t, J=7.4 Hz, 2H), 1.58 (m, 2H), 1.28 (m, 4H), 0.86 (t, J=6.8 Hz, 3H).

M$^-$(APCI$^-$): 248.

b) Preparation of N-[4-(hydrazinocarbonyl)phenyl]hexanamide (Scheme 2, compound B)

To a suspension of methyl 4-(hexanoylamino)benzoate (583 mg, 2.34 mmol) in EtOH (8 mL) was added hydrazine hydrate (1.8 mL). After stirring for 15 h at reflux, the reaction mixture was cooled to rt and a white solid precipitated out. Filtration, washing with water (2×2 mL), and drying under vacuo at rt for 72 hrs gave 321 mg of the title compound (55%) as a white solid in 96.6% purity by HPLC (MaxPlot detection between 230 and 400 nm).

$^1$H NMR (DMSO-d$_6$, 300 MHz) δ 10.06 (s, 1H), 9.60 (s, 1H), 7.75 (d, J=8.5 Hz, 2H), 7.62 (d, J=8.5 Hz, 2H), 4.42 (s, 2H), 2.30 (t, J=7.2 Hz, 2H), 1.58 (m, 2H), 1.28 (m, 4H), 0.86 (m, 3H).

c) Preparation of N-(4-{[2-(5-Iodo-2-oxo-1,2-dihydro-3H-indol-3-ylidene)hydrazino]carbonyl}phenyl)hexanamide Into a suspension of 5-iodo-1H-indole-2,3-dione in acetic acid was added N-[4-(hydrazinocarbonyl)phenyl]hexanamide. After stirring at 100° C. the reaction mixture was cooled to rt and a yellow solid precipitated out. Filtration on a fritté, washing with AcOH, water and drying under vacuo at 60° C. overnight gave 87 mg of the title compound (86%) as a yellow powder in 98.5% purity by HPLC ($R_t$: 4.71, gradient of 8 min, MaxPlot detection between 230 and 400 nm).

M.p. 305° C.

$^1$H NMR (DMSO-d$_6$, 300 MHz) δ 13.81 (s, 1H), 11.45 (s, 1H), 10.27 (s, 1H), 7.82 (m, 5H), 7.71 (d, J=8.3 Hz, 1H), 6.81 (d, J=8.3 Hz, 1H), 2.34 (t, J=7.4 Hz, 2H), 1.60 (m, 2H), 1.29 (m, 4H), 0.87 (t, J=6.6 Hz, 3H).

M$^-$(APCI$^-$): 503; M$^+$(APCI$^+$): 505.

Example 37

4-Cyano-N-(4-{[2-(5-iodo-2-oxo-1,2-dihydro-3H-indol-3-ylidene)hydrazino]-carbonyl}phenyl)benzamide a) Preparation of ethyl 4-[(4-cyanobenzoyl)amino]benzoate (Compound C of Scheme 2)

To a solution of methyl 4-aminobenzoate (500 mg, 3.31 mmol) in anhydrous pyridine (10 mL) was added dropwise 4-cyanobenzoyl chloride (660 mg) at 0° C. After 5 min the temperature was allowed to warm up to rt. After 90 min aminomethyl resin (Polymers Laboratories PL-AMS, 1.93 mmol/g, 720 mg) was added and the resulting mixture was stirred overnight at rt. After filtration and rinsing the resin, water (125 mL) was added to the filtrate and a white solid precipitated out. Filtration and washing with water gave a solid which was dried under vacuo at 60° C. overnight. The title compound (854 mg) was obtained as a pale yellow solid (92%) in 95.2% purity by HPLC (MaxPlot detection between 230 and 400 nm).

$^1$H NMR (300 MHz, DMSO-$d_6$) δ 10.78 (s, 1H), 8.11 (d, J=8.3 Hz, 2H), 8.03 (d, J=8.3 Hz, 2H), 7.97 (d, J=8.8 Hz, 2H), 7.93 (d, J=8.8 Hz, 2H), 3.83 (s, 3H).

M$^-$(APCI$^-$): 279.

b) Preparation of 4-cyano-N-[4-(hydrazinocarbonyl)phenyl]benzamide (Scheme 2, compound B)

To a suspension of methyl 4-[(4-cyanobenzoyl)amino]benzoate (680 mg, 2.43 mmol) in EtOH (8 mL) was added hydrazine hydrate (1.8 mL). After stirring for 15 h at reflux, the reaction mixture was cooled to rt and a white solid precipitated out. Filtration, washing with EtOH (1×2 mL) and water (2×2 mL), and drying under vacuo at rt for 72 hrs gave 432 mg of the title compound (64%) as a pale yellow solid in 94.2% purity by HPLC (MaxPlot detection between 230 and 400 nm).

$^1$H NMR (DMSO-$d_6$, 300 MHz) δ 10.65 (s, 1H), 9.68 (s, 1H), 8.10 (d, J=8.3 Hz, 2H), 8.03 (d, J=8.3 Hz, 2H), 7.83 (s, 4H), 4.46 (s, 2H).

c) Preparation of 4-Cyano-N-(4-{[2-(5-iodo-2-oxo-1,2-dihydro-3H-indol-3-ylidene)-hydrazino]carbonyl}phenyl)benzamide Into a suspension of 5-iodo-1H-indole-2,3-dione in acetic acid was added 4-cyano-N-[4-(hydrazinocarbonyl)phenyl]benzamide. After stirring at 100° C. the reaction mixture was cooled to rt and a yellow solid precipitated out. Filtration on a fritté, washing with AcOH, water and drying under vacuo at 60° C. overnight gave 95 mg of the title compound (89%) as a orange powder in 94.7% purity by HPLC ($R_t$: 4.37, gradient of 8 min, MaxPlot detection between 230 and 400 nm).

M.p. 349° C. (decomp.).

$^1$H NMR (DMSO-$d_6$, 300 MHz) δ 13.84 (s, 1H), 11.46 (s, 1H), 10.84 (s, 1H), 8.13 (d J=8.5 Hz, 2H), 8.05 (d, J=8.5 Hz, 2H), 8.01 (d, J=8.6 Hz, 2H), 7.92 (d, J=8.6 Hz, 2H), 7.84 (d, J=1.5 Hz, 1H), 7.72 (dd, J=8.3, 1.5 Hz, 1H), 6.82 (d, J=8.3 Hz, 1H).

M$^-$(APCI$^-$): 534.

Example 38

4-(Hexloxy)-N-(4-{[2-(5-iodo-2-oxo-1,2-dihydro-3H-indol-3-ylidene)hydrazino]carbonyl}phenyl)benzamide a) Preparation of methyl 4-{[4-(hexyloxy)benzoyl]amino}benzoate (Compound C of Scheme 2)

To a solution of methyl 4-aminobenzoate (500 mg, 3.31 mmol) in anhydrous pyridine (10 mL) was added dropwise 4-(hexyloxy)benzoyl chloride (890 µL) at 0° C. After 5 min the temperature was allowed to warm up to rt. After 90 min aminomethyl resin (Polymers Laboratories PL-AMS, 1.93 mmol/g, 720 mg) was added and the resulting mixture was stirred overnight at rt. After filtration and rinsing the resin, water (125 mL) was added to the filtrate and a white solid precipitated out. Filtration and washing with water gave a solid which was dried under vacuo at 60° C. overnight. The title compound (1073 mg) was obtained as a white solid (91%) in 99.7% purity by HPLC (MaxPlot detection between 230 and 400 nm).

$^1$H NMR (300 MHz, DMSO-$d_6$) δ 10.38 (s, 1H), 7.94 (m, 6H), 7.05 (d, J=9.1 Hz, 2H), 4.04 (t, J=6.4 Hz, 2H), 3.82 (s, 3H), 1.72 (m, 2H), 1.41 (m, 2H), 1.30 (m, 4H), 0.87 (t, J=6.8 Hz, 3H).

M$^-$ $^{(APCI-)}$: 354. M$^+$(APCI$^+$): 356.

b) Preparation of 4-(hexyloxy)-N-[4-(hydrazinocarbonyl)phenyl]benzamide (Scheme 2, compound B)

To a suspension of methyl 4-{[4-(hexyloxy)benzoyl]amino}benzoate (856 mg, 2.41 mmol) in EtOH (10 mL) was added hydrazine hydrate (1.8 mL). After stirring for 15 h at reflux, the reaction mixture was cooled to rt and a white solid precipitated out. Filtration, washing with EtOH (1×2 mL) and water (2×2 mL), and drying under vacuo at rt for 72 hrs gave 681 mg of the title compound (80%) as a white solid in 99.7% purity by HPLC (MaxPlot detection between 230 and 400 nm).

$^1$H NMR (DMSO-$d_6$, 300 MHz) δ 10.25 (s, 1H), 9.64 (s, 1H), 7.94 (d, J=8.9 Hz, 2H), 7.83 (d, J=9.0 Hz, 2H), 7.80 (d, J=9.0 Hz, 2H), 7.05 (d, J=8.9 Hz, 2H), 4.43 (s, 2H), 4.04 (t, J=6.4 Hz, 2H), 1.73 (m, 2H), 1.42 (m, 2H), 1.30 (m, 4H), 0.87 (t, J=6.8 Hz, 3H).

c) Preparation of 4-(Hexyloxy)-N-(4-{[2-(5-iodo-2-oxo-1,2-dihydro-3H-indol-3-ylidene)hydrazino]carbonyl}phenyl)benzamide Into a suspension of 5-iodo-1H-indole-2,3-dione in acetic acid was added 4-(hexyloxy)-N-[4-(hydrazinocarbonyl)phenyl]-benzamide. After stirring at 100° C., the reaction mixture was cooled to rt and a yellow solid precipitated out. Filtration on a fritté, washing with AcOH, water and drying under vacuo at 60° C. overnight gave 110 mg of the title compound (90%) as a yellow powder in 91.1% purity by HPLC ($R_t$: 5.86, gradient of 8 min, MaxPlot detection between 230 and 400 nm).

M.p. 313° C.

$^1$H NMR (DMSO-$d_6$, 300 MHz) δ 13.84 (s, 1H), 11.46 (s, 1H), 10.44 (s, 1H), 7.99.(m, 4H), 7.89 (d, J=7.5 Hz, 2H), 7.84 (s, 1H), 7.72 (d, J=7.9 Hz, 1H), 7.07 (d, J=7.6 Hz, 2H), 6.82 (d, J=7.9 Hz, 1H), 4.05 (m, 2H), 1.73 (m, 2H), 1.42 (m, 2H), 1.31 (m, 4H), 0.88 (m, 3H).

M$^-$(APCI$^-$): 609; M$^+$(APCI$^+$): 611.

Example 39

4-Heptyl-N-(4-{[2-(5-iodo-2-oxo-1,2-dihydro-3H-indol-3-ylidene)hydrazino]carbonyl}phenyl)benzamide a) Preparation of methyl 4-[(4-heptylbenzoyl)amino]benzoate (Scheme 2, compound C)

To a solution of methyl 4-aminobenzoate (500 mg, 3.31 mmol) in anhydrous pyridine (10 mL) was added dropwise 4-heptylbenzoyl chloride (950 µL) at 0° C. After 5 min the temperature was allowed to warm up to rt. After 90 min aminomethyl resin (Polymers Laboratories PL-AMS, 1.93 mmol/g, 720 mg) was added and the resulting mixture was stirred overnight at rt. After filtration and rinsing the resin, water (125 mL) was added to the filtrate and a white solid precipitated out. Filtration and washing with water gave a solid which was dried under vacuo at 60° C. overnight. The title compound (1051 mg) was obtained as a white solid (90%) in 96.9% purity by HPLC (MaxPlot detection between 230 and 400 nm).

$^1$H NMR (300 MHz, DMSO-d$_6$) δ 10.47 (s, 1H), 7.94 (s, 4H), 7.88 (d, J=8.1 Hz, 2H), 7.35 (d, J=8.1 Hz, 2H), 3.82 (s, 3H), 2.64 (t, J=7.6 Hz, 2H), 1.58 (m, 2H), 1.26 (m, 8H), 0.84 (t, J=6.5 Hz, 3H).

M$^-$(APCI$^-$): 352. M$^+$(APCI$^+$): 354.

b) Preparation of 4-heptyl-N-[4-(hydrazinocarbonyl)phenyl]benzamide (Scheme 2, compound B)

To a suspension of methyl 4-[(4-heptylbenzoyl)amino] benzoate (823 mg, 2.33 mmol) in EtOH (10 mL) was added hydrazine hydrate (1.8 mL). After stirring for 15 h at reflux, the reaction mixture was cooled to rt and a white solid precipitated out. Filtration, washing with EtOH (1×2 mL) and water (2×2 mL), and drying under vacuo at rt for 72 hrs gave 619 mg of the title compound (75%) as a white solid in 99.4% purity by HPLC (MaxPlot detection between 230 and 400 nm).

$^1$H NMR (DMSO-d$_6$, 300 MHz) δ 10.34 (s, 1H), 9.66 (s, 1H), 7.87 (d, J=8.1 Hz, 2H), 7.82 (m, 4H), 7.34 (d, J=8.1 Hz, 2H), 4.43 (s, 2H), 2.64 (t, J=7.6 Hz, 2H), 1.58 (m, 2H), 1.25 (m, 8H), 0.84 (t, J=6.6 Hz, 3H).

c) Preparation of 4-Heptyl-N-(4-{[2-(5-iodo-2-oxo-1,2-dihydro-3H-indol-3-ylidene)hydrazino]carbonyl}phenyl)benzamide Into a suspension of 5-iodo-1H-indole-2,3-dione in acetic acid was added 4-heptyl-N-[4-(hydrazinocarbonyl)phenyl]-benzamide. After stirring at 100° C. the reaction mixture was cooled to rt and a yellow solid precipitated out. Filtration on a fritté, washing with AcOH, water and drying under vacuo at 60° C. overnight gave 111 mg of the title compound (91%) as a yellow powder in 93.1% purity by HPLC (R$_t$: 6.3, gradient of 8 min, MaxPlot detection between 230 and 400 nm).

M.p. 306° C.

$^1$H NMR (DMSO-d$_6$, 300 MHz) δ 13.84 (s, 1H), 11.46 (s, 1H), 10.53 (s, 1H), 8.02 (d, J=8.7 Hz, 2H), 7.89 (m, 4H), 7.84 (d, J=1.5 Hz, 1H), 7.71 (dd, J=8.3, 1.5 Hz, 1H), 7.36 (d, J=8.2 Hz, 2H), 6.81 (d, J=8.3 Hz, 1H), 2.65 (t, J=7.6 Hz, 2H), 1.59 (m, 2H), 1.26 (m, 8H), 0.85 (t, J=6.8 Hz, 3H).

M$^-$(APCI$^-$): 607; M$^+$(APCI$^+$): 609.

Example 40

2-(2-Nitro-4,5-dimethoxyphenyl)-N'-[5-iodo-2-oxo-1,2-dihydro-3H-indol-3-yliden)acetohydrazide Following the general method as outlined in Example 1, into a suspension of 5-iodo-1H-indole-2,3one in acetic acid was added 2-(3-nitro-4,5-dihydroxyphenyl)acetohydrazide. After stirring at 100° C. the reaction mixture was cooled to rt and a yellow solid precipitated out. Filtration on a fritté, washing with AcOH, water and drying under vacuo at 60° C. overnight gave 78 mg of the title compound (76%) as a yellow powder in 90.6% purity by HPLC (R$_t$: 4.49, gradient of 8 min, MaxPlot detection between 230 and 400 nm).

M.p. 307° C. (decomp.).

M$^-$(APCI$^-$): 509; M$^+$(APCI$^+$): 511.

Example 41

N'-(5-Iodo-2-oxo-1,2-dihydro-3H-indol-3-ylidene)-1-(3-pyridinylmethyl)-4-piperidinecarbohydrazide Following the general method as outlined in Example 1, into a suspension of 5-iodo-1H-indole-2,3-dione in acetic acid was added 2-[1-(3-pyrdinylmethyl)-4-piperidinyl]acetohydrazide. After stirring at 100° C. the reaction mixture was cooled to rt and a yellow solid precipitated out. Filtration on a fritté, washing with AcOH, water and drying under vacuo at 60° C. overnight gave 72 mg of the title compound (74%) as a yellow powder in 86.8% purity by HPLC (R$_t$: 2.02, gradient of 8 min, MaxPlot detection between 230 and 400 nm).

M.p. 125° C.

M$^-$(APCI$^-$): 488; M$^+$(APCI$^+$): 490.

Example 42

N'-(5-Iodo-2-oxo-1,2-dihydro-3H-indol-3-ylidene)2-amino-5-nitro-benzohydrazide Following the general method as outlined in Example 1, into a suspension of 5-iodo-1H-indole-2,3-dione in acetic acid was added 2-amino-5-nitrobenzohydrazide. After stirring at 100° C. the reaction mixture was cooled to rt and a yellow solid precipitated out. Filtration on a fritté, washing with AcOH, water and drying under vacuo at 60° C. overnight gave 69 mg of the title compound (76%) as a yellow powder in 98.8% purity by HPLC (R$_t$: 4.22, gradient of 8 min, MaxPlot detection between 230 and 400 nm).

M.p. 344° C. (decomp.).

M$^-$(APCI$^-$): 450.

Example 43

2-[5-(3-Nitrophenyl)-2H-tetrazol-2-yl]-N'-(5-iodo-2-oxo-1,2-dihydro-3H-indol-3-ylidene)acetohydrazide Following the general method as outlined in Example 1, into a suspension of 5-iodo-1H-indole-2,3-dione in acetic acid was added 2-[5-(3-nitrophenyl)-2H-tetrazol-2-yl]acetohydrazide. After stirring at 100° C. the reaction mixture was cooled to rt and a yellow solid precipitated out. Filtration on a fritté, washing with AcOH, water and drying under vacuo at 60° C. overnight gave 80 mg of the title compound (77%) as a yellow powder in 97% purity by HPLC (R$_t$: 4.96, gradient of 8 min, MaxPlot detection between 230 and 400 nm).

M.p. 254° C. (decomp.).

M$^-$(APCI$^-$): 517.

Example 44

N'-(5-Iodo-2-oxo-1,2-dihydro-3H-indol-3-ylidene)-2-[5-(1pyrrolidinyl)-2H-tetrazol-2-yl]acetohydrazide Following the general method as outlined in Example 1, into a suspension of 5-iodo-1H-indole-2,3-dione in acetic acid was added 2-[5-(1-pyrrolidinyl)-2H-tetrazol-2-yl]acetohydrazide. After stirring at 100° C. the reaction mixture was cooled to rt and a yellow solid precipitated out. Filtration on a fritté, washing with AcOH, water and drying under vacuo at 60° C. overnight gave 67 mg of the title compound (72%) as a yellow powder in 95% purity by HPLC ($R_t$: 4.24, gradient of 8 min, MaxPlot detection between 230 and 400 nm).

M.p. 265° C. (decomp.).
M$^-$(APCI$^-$): 465; M$^+$(APCI$^+$): 467.

Example 45

N'-(5-Iodo-2-oxo-1,2-dihydro-3H-indol-3-ylidene)-2-[5-(4-morpholinyl)-2H-tetrazol-2-yl]acetohydrazide Following the general method as outlined in Example 1, into a suspension of 5-iodo-1H-indole-2,3-dione in acetic acid was added 2-[5-(4-morpholinyl)-2H-tetrazol-2-yl]acetohydrazide. After stirring at 100° C. the reaction mixture was cooled to rt and a yellow solid precipitated out. Filtration on a fritté, washing with AcOH, water and drying under vacuo at 60° C. overnight gave 73 mg of the title compound (76%) as a yellow powder in 86.7% purity by HPLC ($R_t$: 3.84, gradient of 8 min, MaxPlot detection between 230 and 400 nm).

M.p. 253° C. (decomp.).
M$^-$(APCI$^-$): 481; M$^+$(APCI$^+$): 483.

Example 46

4-{2-[2-(5-Iodo-2-oxo-1,2-dihydro-3H-indol-3-ylidene)hydrazino]-2-oxoethoxy}benzoic acid a) Preparation of 4-(2-hydrazino-2-oxoethoxy)benzoic acid (compound C, Scheme 2)

In an Parr autoclave, a solution of benzyl 4-(2-hydrazino-2-oxoethoxy)benzoate (400 mg, 1.3 mmol) and a catalytic amount Pd/C in AcOH (25 mL) was stirred under hydrogen pressure (5 Bars) at rt for 45 min. After filtration over celite, the filtrate was evaporated off. The residue was taken up in MeOH and a beige solid precipitated out. Filtration and drying under vacuo at 50° C. overnight gave the title compound as a beige solid (118 mg) in a 42% yield.

$^1$H NMR (DMSO-d$_6$/CD$_3$OD (35/1), 300 MHz) δ 7.87 (m, 2H), 7.06 (d, J=8.6 Hz, 0.5H), 7.00 (d, J=8.6 Hz, 0.5H), 6.93 (d, J=8.6 Hz, 1H), 5.05 (s, 1H), 4.71 (s, 1H).

b) Preparation of 4-{2-[2-(5-Iodo-2-oxo-1,2-dihydro-3H-indol-3-ylidene)hydrazino]-2-oxoethoxy}benzoic acid Into a suspension of 5-iodo-1H-indole-2,3-dione in acetic acid was added 4-(2-hydrazino-2-oxoethoxy)benzoic acid. After stirring at 100° C., the reaction mixture was cooled to rt and a yellow solid precipitated out. Filtration on a fritté, washing with AcOH, water and drying under vacuo at 60° C. overnight gave 6 mg of the title compound (7%) as a yellow solid in 97.8% purity by HPLC ($R_t$: 3.63, gradient of 8 min, MaxPlot detection between 230 and 400 nm).

$^1$H NMR (DMSO-d$_6$, 300 MHz) δ 13.62 (br s, 0.6H), 12.64 (br s, 1H), 12.48 (br s, 0.4H), 11.36 (s, 1H), 7.92 (d, J=8.1 Hz, 2H), 7.84 (br s, 1H), 7.71 (dd, J=8.3, 1.9 Hz, 1H), 7.11 (d, J=8.1 Hz, 2H), 6.80 (d, J=8.3 Hz, 1H), 5.39 (br s, 0.8H), 4.97 (br s, 1.2H).

M$^-$(APCI$^-$): 464.

Example 47

4-{[2-(5-Iodo-2-oxo-1,2-dihydro-3H-indol-3-ylidene)hydrazino]carbonyl}-N-phenylbenzamide a) Preparation of 4-(hydrazinoarbonyl-N-phenylbenzamide (Scheme 2, compound B)

To a suspension of methyl 4-(anilinocarbonyl)benzoate (634 mg, 2.48 mmol) in EtOH (8 mL) was added hydrazine hydrate (1.81 mL). After stirring for 15 h at reflux, the reaction mixture was cooled to rt and a white solid precipitated out. Filtration, washing with EtOH (3×3 mL) and water (3×3 mL), and drying under vacuo at 60° C. for 2 hrs gave 548 mg of the title compound (86%) as a white solid in 96.3% purity by HPLC (MaxPlot detection between 230 and 400 nm).

$^1$H NMR (DMSO-d$_6$, 300 MHz) δ 10.33 (s, 1H), 9.93 (s, 1H), 8.00 (d, J=8.3 Hz, 2H), 7.94 (d, J=8.3 Hz, 2H), 7.77 (d, J=7.7 Hz, 2H), 7.35 (dd, J=7.7, 7.4 Hz, 2H), 7.10 (t, J=7.4 Hz, 1H), 4.55 (s, 2H).

b) Preparation of 4-{[2-(5-Iodo-2-oxo-1,2-dihydro-3H-indol-3-ylidene)hydrazino]carbonyl}-N-phenylbenzamide Following the general method as outlined in Example 1, into a suspension of 5-iodo-1H-indole-2,3-dione in acetic acid was added 4-(hydrazinoarbonyl)-N-phenylbenzamide. After stirring at 100° C. the reaction mixture was cooled to rt and a yellow solid precipitated out. Filtration on a fritté, washing with AcOH, water and drying under vacuo at 60° C. overnight gave 198 mg of the title compound (71%) as a yellow powder in 94.6% purity by HPLC ($R_t$: 4.48, gradient of 8 min, MaxPlot detection between 230 and 400 nm).

M.p. 374° C. (decomp).
$^1$H NMR (DMSO-d$_6$, 300 MHz) δ 13.87 (s, 1H), 11.49 (s, 1H), 10.44 (s, 1H), 8.14 (d, J=8.3 Hz, 2H), 8.02 (d, J=8.3 Hz, 2H), 7.84 (br s, 1H), 7.78 (d, J=7.9 Hz, 2H), 7.73 (dd, J=7.9, 1.5 Hz), 7.37 (dd, J=7.9, 7.4 Hz, 2H), 7.12 (t, J=7.4 Hz, 1H), 6.82 (d, J=7.9 Hz, 1H).

M$^-$(APCI$^-$): 509; M$^+$(APCI$^+$): 511.

Example 48

4-Cyano-N-(3-{[2-(5-iodo-2-oxo-1,2-dihydro-3H-indol-3-ylidene)hydrazino]carbonyl}phenyl)benzamide a) Preparation of methyl 3-[(4-cyanobenzoyl)amino]benzoate (compound C, Scheme 2)

To a solution of methyl 4-aminobenzoate (500 mg, 3.31 mmol) in anydrous pyridine (10 mL) was added dropwise 4-cyanobenzoyl chloride (660 mg, 4.0 mmol) at 0° C. After 5 min the temperature was allowed to warm up to rt. After 3 hrs aminomethyl resin (Polymers Laboratories PL-AMS, 1.96 mmol/g, 720 mg) was added and the resulting mixture was stirred overnight at rt. After rinsing the resin and filtration, water (25 mL) was added to the filtrate and a beige solid precipated out. Filtration and washing with water gave a solid which was dried under vacuo at 60° C. for 5 hrs. The title compound (774 mg) was obtained as a beige solid (83%) in 97.7% purity by HPLC (MaxPlot detection between 230 and 400 nm) $^1$H NMR (300 MHz, DMSO-d$_6$) δ 10.68 (s, 1H), 8.45 (m, 1H), 8.12 (d, J=8.3 Hz, 2H), 8.05 (m, 3H), 7.71 (d, J=7.8 Hz, 1H), 7.52 (dd, J=7.9, 7.8 Hz, 1H), 3.86 (s, 3H).

b) Preparation of 4-cyano-N-[3-(hydrazinocarbonyl)phenyl]benzamide (compound B, Scheme 2)

To a suspension of methyl 3-[(4-cyanobenzoyl)amino] benzoate (762 mg, 2.72 mmol) in EtOH (8 mL) was added hydrazine hydrate (1.79 mL). After stirring for 15 h at reflux, the reaction mixture was cooled to rt and a white solid precipitated out. Filtration, washing with EtOH (3 mL) and water (3×3 mL) and drying under vacuo at 60° C. for 2 hrs gave 518 mg of the title compound (68%) as a white solid in 98.8% purity by HPLC (MaxPlot detection between 230 and 400 nm).

$^1$H NMR (DMSO-d$_6$, 300 MHz) δ 10.61 (s, 1H), 9.76 (s, 1H), 8.22 (s, 1H), 8.12 (d, J=8.2 Hz, 2H), 8.03 (d, J=8.2 Hz, 2H), 7.3 (d, J=7.7 Hz, 1H), 7.5 (d, J=7.8 Hz, 1H), 7.42 (dd, J=7.8, 7.7 Hz, 1H), 4.48 (s, 2H).

c) Preparation of 4-Cyano-N-(3-{[2-(5-iodo-2-oxo-1,2-dihydro-3H-indol-3-ylidene)-hydrazino]-carbonyl}phenyl)benzamide Into a suspension of 5-iodo-1H-indole-2,3-dione in acetic acid was added 4-cyano-N-[3-hydrazinocarbonyl)phenyl] benzamide. After stirring at 100° C. the reaction mixture was cooled to rt and a yellow solid precipitated out. Filtration on a fritté, washing with AcOH, water and drying under vacuo at 60° C. overnight gave 181 mg of the title compound (61%) as a orange powder in 96.5% purity by HPLC (R$_t$: 4.4, gradient of 8 min, MaxPlot detection between 230 and 400 nm).

M.p. 309° C. (decomp).

$^1$H NMR (DMSO-d$_6$, 300 MHz) δ 13.84 (s, 1H), 11.45 (s, 1H), 10.77 (s, 1H), 8.45 (s, 1H), 8.10 (m, 5H), 7.86 (s, 1H), 7.72 (br d, J=8.3 Hz, 1H), 7.61 (m, 2H), 6.81 (d, J=8.3 Hz, 1H).

M$^-$(APCI$^-$): 534; M$^+$(APCI$^+$): 536.

Example 49

N'-[5-Iodo-2-oxo-1,2-dihydro-3H-indol-3-ylidene]-4-[4-(4-morpholinyl-methyl)phenoxy]benzohydrazide a) Preparation of methyl 4-[4(bromomethyl)phenoxy]benzoate (Compound C of Scheme 2)

At 10° C. a mixture of HBr (400 mL) and sulfuric acid (20 mL) was added a solution of methyl 4-[4-(bromomethyl) phenoxy]benzoate (100 g) in 1,2-dichloroethane. Then the reaction mixture was allowed to stir at 60° C. for 3 hrs. After extraction the organic layer was washed with water and a saturated aqueous solution of NaHCO$_3$. Drying over sodium sulfate and evaporation under vacuo gave the title compound (110 g) in a 88% yield.

b) Preparation of methyl 4-[4-(morpholinylmethyl)phenoxy benzoate (Compound C of Scheme 2)

To a stirred solution of morpholine (10.7 g, 0.12 mol) and methyl amine (35 mL, 0.21 M) in absolute alcohol (550 mL) was added methyl 4-[4-(bromomethyl)phenoxy)]benzoate (55 g, 0.17 mol) in 250 mL of dry THF. The reaction mixture was allowed to stir overnight at rt. Then the reaction mixture was concentrated and the residue was tretaed with HCl (4N). The acidic mixture was washed with diethyl ether to remove organic impurities and basified using an aqueous solution of NaHCO$_3$ (10%). Further extraction with diethyl ether, washing with brine and drying under vacuo gave the title compound (34 g) in a 87% yield.

$^1$H NMR (300 MHz, DMSO-d$_6$) δ 7.92 (d, J=7.7 Hz, 2H), 7.39 (d, J=7.7 Hz, 2H), 7.1 (m, 4H), 3.82 (s, 3H), 3.58 (m, 4H), 3.47 (s, 2H), 2.38 (m, 4H).

c) Preparation of 4-[4-(1,3-oxazinan-3-ylmethyl) phenoxy]benzohydrazide (Scheme 2, compound B)

To a suspension of methyl 4-(4-(morpholinylmethyl)phenoxy benzoate (1309 mg, 4.00 mmol) in EtOH (6 mL) was added hydrazine hydrate (1.46 mL). After stirring for 18 h at reflux, the reaction mixture was cooled to rt and poured into water (20 mL). A white solid precipitated out. Filtration, washing with water (3×3 mL) and drying under vacuo at 60° C. for 4 hrs gave 919 mg of the title compound as a white solid in a 70% yield.

$^1$H NMR (DMSO-d$_6$, 300 MHz) δ 9.67 (s, 1H), 7.82 (d, J=9.0 Hz, 2H), 7.34 (d, J=8.5 Hz, 2H), 7.02 (d, J=8.5 Hz, 2H), 6.98 (d, J=9.0 Hz, 2H), 4.45 (s, 2H), 3.56 (m, 4H), 3.44 (s, 2H), 2.34 (m, 4H).

d) Preparation of N'-[5-Iodo-2-oxo-1,2-dihydro-3H-indol-3-ylidene]-4-[4-(4-morpholinyl-methyl)phenoxy]benzohydrazide Into a suspension of 5-iodo-1H-indole-2,3-dione in acetic acid was added 4-[4-(1,3-oxazinan-3-ylmethyl)phenoxy] benzohydrazide. After stirring at 100° C., the reaction mixture was cooled to rt and a yellow solid precipitated out. Filtration on a fritté, washing with AcOH, water and drying under vacuo at 60° C. overnight gave 194 mg of the title compound (67%) as a yellow solid in 98.9% purity by HPLC (R$_t$: 3.27, gradient of 8 min, MaxPlot detection between 230 and 400 nm).

M.p. 252° C.

$^1$H NMR (DMSO-d$_6$, 300 MHz) δ 13.79 (s, 1H), 11.46 (s, 1H), 7.90 (d, J=8.8 Hz, 2H), 7.83 (d, J=1.5 Hz, 1H), 7.71 (dd, J=8.3, 1.5 Hz, 1.5), 7.38 (d, J=8.5 Hz, 2H), 7.14 (d, J=8.8 Hz, 2H), 7.10 (d, J=8.5 Hz, 2H), 6.80 (d., J=8.3 Hz, 1H), 3.57 (m, 4H), 3.47 (s, 2H), 2.36 (m, 4H).

M$^-$(APCI$^-$): 581; M$^+$(APCI$^+$): 583.

Example 50

N-(4-{[2-(5-Iodo-2-oxo-1,2-dihydro-3H-indol-3-ylidene)hydrazino]-carbonyl}phenyl)benzamide Following the general method as outlined in Example 1, into a suspension of 5-iodo-1H-indole-2,3-dione in acetic acid was added N-[4-(hydrazinocarbonyl)phenyl]benzamide. After stirring at 100° C. the reaction mixture was cooled to rt and a yellow solid precipitated out. Filtration on a fritté, washing with AcOH, water and drying under vacuo at 60° C.

overnight gave 114 mg of the title compound (89%) as a yellow powder in 96.3% purity by HPLC ($R_t$: 4.4, gradient of 8 min, MaxPlot detection between 230 and 400 nm).

M.p. 338° C. (decomp).

$^1$H NMR (DMSO-$d_6$, 300 MHz) δ 13.85 (s, 1H), 11.47 (s, 1H), 10.62 (s, 1H), 8.00 (m, 4H), 7.90 (d, J=8.6 Hz, 2H), 7.83 (d, J=1.5 Hz, 1H), 7.71 (dd, J=8.2, 1.5 Hz, 1H), 7.59 (m, 3H), 6.81 (d, J=8.2 Hz, 1H).

M$^-$(APCI$^-$): 509.

Example 51

4-(Benzyloxy)-N'-(5-iodo-2-oxo-1,2-dihydro-3H-indol-3-ylidene)benzohydrazide

Following the general method as outlined in Example 1, into a suspension of 5-iodo-1H-indole-2,3-dione in acetic acid was added 4-(benzyloxy)benzohydrazide. After stirring at 100° C., the reaction mixture was cooled to rt and a yellow solid precipitated out. Filtration on a fritté, washing with AcOH, water and drying under vacuo at 60° C. overnight gave 247 mg of the title compound (90%) as a yellow powder in 98.9% purity by HPLC ($R_t$: 5.03, gradient of 8 min, MaxPlot detection between 230 and 400 nm).

M.p. 298° C.

IR (neat) v 3240, 1693, 1667, 1603, 1494, 1448, 1244, 1172, 1140, 1121, 1025, 916 cm$^{-1}$.

$^1$H NMR (DMSO-$d_6$, 300 MHz) δ 13.80 (s, 1H), 11.46 (s, 1H), 7.86 (d, J=8.8 Hz, 2H), 7.81 (br s, 1H), 7.70 (dd, J=8.3, 1.5 Hz, 1H), 7.48-7.42 (m, 5H), 7.22 (d, J=8.8 Hz, 2H), 6.80 (d, J=8.3 Hz, 1H), 5.22 (s, 2H).

M$^-$(ESI (LC/MS)$^-$): 496; M$^+$(ESI (LC/MS)$^+$): 498.

Example 52

N-(3-{[2-(5-Iodo-2-oxo-1,2-dihydro-3H-indol-3-ylidene)hydrazino]-carbonyl}phenyl)-3-phenylpropanamide a) Preparation of N-[3-hydrazinocarbonyl)phenyl]-3-phenylpropanamide (Scheme 2, compound B)

To a suspension of methyl 3-[(3-phenylpropanoyl)amino]benzoate (623 mg, 2.20 mmol) in EtOH (8 mL) was added hydrazine hydrate (1.79 mL). After stirring for 15 h at reflux, the reaction mixture was cooled to rt an treated with water (30 mL). A white solid precipitated out. Filtration, washing with water (3×3 mL) and drying under vacuo at 60° C. for 2 hrs gave 377 mg of the title compound (65%) as a white solid in 95.8% purity by HPLC (MaxPlot detection between 230 and 400 nm).

$^1$H NMR (DMSO-$d_6$, 300 MHz) δ 10.03 (s, 1H), 9.69 (s, 1H), 7.98 (s, 1H), 7.74 (d, J=7.7 Hz, 1H), 7.43 (d, J=7.6 Hz, 1H), 7.35-7.17 (m, 6H), 4.47 (s, 2H), 2.90 (t, J=7.6 Hz, 2H), 2.62 (t, J=7.6 Hz, 2H).

b) Preparation of N-(3-{[2-(5-Iodo-2-oxo-1,2-dihydro-3H-indol-3-ylidene)hydrazino]-carbonyl}phenyl)-3-phenylpropanamide Following the general method as outlined in Example 1, into a suspension of 5-iodo-1H-indole-2,3-dione in acetic acid was added N-[3-hydrazinocarbonyl)phenyl]-3-phenyl-propanamide. After stirring at 100° C., the reaction mixture was cooled to rt and a yellow solid precipitated out. Filtration on a fritté, washing with AcOH, water and drying under vacuo at 60° C. overnight gave 210 mg of the title compound (78%) as a yellow powder in 96.95% purity by HPLC ($R_t$: 4.53, gradient of 8 min, MaxPlot detection between 230 and 400 nm).

M.p. 293° C.

$^1$H NMR (DMSO-$d_6$, 300 MHz) δ 13.80 (s, 1H), 11.46 (s, 1H), 10.23 (s, 1H), 8.23 (s, 1H), 7.85 (m, 2H), 7.72 (dd, J=8.3, 1.5 Hz, 1H), 7.53 (m, 2H), 7.28 (m, 4H), 7.18 (m, 1H), 6.81 (d, J=8.3 Hz, 1H), 2.93 (t, J=7.6 Hz, 2H), 2.66 (t, J=7.6 Hz, 2H).

M$^-$(APCI$^-$): 537.

Example 53

4-{[2-(5-Iodo-2-oxo-1,2-dihydro-3H-indol-3-ylidene)hydrazino]carbonyl}-N-{3-[(trifluoromethyl)sulfonyl]phenyl}benzamide a) Preparation of methyl 4-({3-[(trifluoromethyl)sulfonyl]anilino}carbonyl)benzoate (Compound C of Scheme 2)

To a solution of 3-aminophenyltrifluoromethylsulfone (750 mg, 3.33 mmol) in anhydrous DMF (10 mL) were added DIEA (0.7 mL, 4 mmol) and terephtalic acid monomethyl ester chloride (794 mg, 4 mmol) at 0° C. After 5 min the reaction mixture was allowed to warm up to rt. After 1 hr, water (5 mL) was added and the resulting reaction mixture was allowed to stir at rt overnight The reaction mixture was poured into water (100 mL) and a brown solid precipitated out. Filtration and washing with water (3×5 mL) of the solid gave a residue which was purified by flash chromatography using EtOAc/cyclohexane as eluant The title compound was collected as a white solid (390 mg, 30%) in a 99.8% purity by HPLC (MaxPlot detection between 230 and 400 nm).

$^1$H NMR (300 MHz, DMSO-$d_6$) δ 10.98 (s, 1H), 8.68 (br s, 1H), 8.38 (m, 1H), 8.11 (s, 4H), 7.86 (m, 2H), 3.89 (s, 3H).

M$^-$(APCI$^-$): 386.

b) Preparation of 4-(hydrazinocarbonyl)-N-{3-[(trifluoromethyl)sulfonyl]phenyl}-benzamide (Scheme 2 compound B)

To a suspension of methyl 4-({3-[(trifluoromethyl)sulfonyl]anilino}carbonyl)benzoate (390 mg, 1.1 mmol) in EtOH (6 mL) was added hydrazine hydrate (1 mL). After stirring for 15 hrs at reflux, the reaction mixture was cooled to rt and a white solid precipitated out Filtration, washing with EtOH (1×1 mL) and water (3×1 mL), and drying under vacuo at 60° C. for 2 hrs gave 247 mg of the title compound (63%) as a white solid in 95% purity by HPLC (MaxPlot detection between 230 and 400 nm).

$^1$H NMR (DMSO-$d_6$, 300 MHz) δ 10.89 (s, 1H), 9.95 (s, 1H), 8.69 (s, 1H), 8.38 (n, 1H), 8.05 (d, J=8.4 Hz, 2H), 7.97 (d, J=8.4 Hz, 2H), 7.86 (m, 2H), 4.58 (s, 2H).

c) Preparation of 4-{[2-(5-Iodo-2-oxo-1,2-dihydro-3H-indol-3-ylidene)hydrazino]carbonyl}-N-{3-[(trifluoromethyl)sulfonyl]phenyl}benzamide Into a suspension of 5-iodo-1H-indole-2,3-dione in acetic acid was added 4-(hydrazinocarbonyl)-N-{3-[(trifluoromethyl)sulfonyl]phenyl}benzamide. After stirring at 100° C., the reaction mixture was cooled to rt and a yellow solid precipitated out. Filtration on a fritté, washing with AcOH, water and drying under vacuo at 60° C. overnight gave 80 mg of the title compound (76%) as a yellow solid in 76% purity by HPLC ($R_t$: 4.96, gradient of 8 min, MaxPlot detection between 230 and 400 nm).

$^1$H NMR (DMSO-d$_6$, 300 MHz) δ 13.88 (s, 1H), 11.50 (s, 1H), 11.01 (s, 1H), 8.69 (s, 1H), 8.38 (m, 1H), 8.19 (d, J=8.3 Hz, 2H), 8.05 (d, J=8.3Hz, 2H), 7.86 (m, 3H), 7.73 (dd, J=8.3, 1.5 Hz, 1H), 6.82 (d, J=8.3 Hz, 1H).

M$^-$(ESI$^-$): 641.

Example 54

4-Chloro-N-(4-{[2-(5-iodo-2-oxo-1,2-dihydro-3H-indol-3-ylidene)hydrazino]carbonyl}benzyl)benzamide a) Preparation of methyl 4-{[(4-chlorobenzoyl)amino]methyl}benzoate (Compound C of Scheme 2)

To a stirred solution of methyl 4-(aminomethyl)benzoate (75 g, 0.46 mol) and TEA (315 mL, 2.27 mol) in anhydrous DCM (1.5 L) was added a solution of freshly prepared 4-chloro benzoyl chloride (0.91 mol) in DCM (400 mL). The resulting mixture was allowed to stir for 12 hrs. The reaction was quenched with a 10% aqueous solution of sodium hydrogenocarbonate. The organic layer was washed with a 1.5N HCl solution and water. After drying over MgSO$_4$ and evaporation of the solvent in vacuo, a solid was obtained. Recrystallization form MeOH gave the title compound (80 g) in a 60% yield as a white powder.

$^1$H NMR (300 MHz, DMSO-d$_6$) δ 9.22 (t, J=5.23 Hz, 1H), 7.92 (dd, J=7.0, 1.7 Hz, 4H), 7.58 (d, J=7.0 Hz, 2H), 7.45 (d, J=7.0 Hz, 2H), 4.57 (d, J=4.5 Hz, 2H), 3.86 (s, 3H).

b) Preparation of 4-chloro-N-[4-(hydrazinocarbonyl)benzyl]benzamide (Scheme 2, compound B)

To a suspension of methyl 4-{[(4-chlorobenzoyl)amino]methyl}benzoate (303 mg, 1.0 mmol) in EtOH (6 mL) was added hydrazine hydrate (1.0 mL). After stirring for 15 h at reflux, the reaction mixture was cooled to rt and a white solid precipitated out. Filtration, washing with water (3×2 mL) and drying under vacuo at 60° C. for 2 hrs gave 213 mg of the title compound (70%) as a white solid in 96.5% purity by HPLC (MaxPlot detection between 230 and 400 nm).

$^1$H NMR (300 MHz, DMSO-d$_6$) δ 9.69 (s, 1H), 9.16 (br s, 1H), 7.90 (d, J=7.9 Hz, 2H), 7.76 (d, J=7.9 Hz, 2H), 7.55 (d, J=7.9 Hz, 2H), 7.35 (d, J=7.9 Hz, 2H), 4.50 (d, J=5.3 Hz, 2H), 4.44 (s, 2H).

c) Preparation of 4-Chloro-N-(4-{[2-(5-iodo-2-oxo-1,2-dihydro-3H-indol-3-ylidene)hydrazino]carbonyl}benzyl)benzamide Into a suspension of 5-iodo-1H-indole-2,3-dione in acetic acid was added 4-chloro-N-[4-(hydrazinocarbonyl)benzyl]benzamide. After stirring at 100° C. the reaction mixture was cooled to rt and a yellow solid precipitated out. Filtration on a fritté, washing with AcOH, water and drying under vacuo at 60° C. overnight gave 126 mg of the title compound (92%) as a yellow solid in 89.18% purity by HPLC (R$_t$: 4.48, gradient of 8 min, MaxPlot detection between 230 and 400 nm).

$^1$H NMR (DMSO-d$_6$, 300 MHz) δ 13.81 (s, 1H), 11.46 (s, 1H), 9.23 (t, J=5.3 Hz, 1H), 7.88 (m, 5H), 7.71 (d, J=8.3 Hz, 1H), 7.55 (m, 4H), 6.81 (d, J=8.3 Hz, 1H), 4.57 (d, J=5.3 Hz, 1H).

M$^-$(ESI$^-$): 557; M$^+$(ESI$^+$): 559.

Example 55

Methyl 4-{3-[2-(5-iodo-2-oxo-1,2-dihydro-3H-indol-3-ylidene)hydrazino]-3-oxopropyl}benzoate a) Preparation of methyl 3-(3-hydrazino-3-oxopropyl)benzoate (Compound C of Scheme 2)

To a suspension of methyl 4-(3-methoxy-3-oxopropyl)benzoate (500 mg, 2.25 mmol) in MeOH (10 mL) was added hydrazine hydrate (1.09 mL). After stirring for 18 h at rt, the reaction mixture was poured into water (30 mL). The solvent was evaporated off until a final volume of 5 mL and a white solid precipitated out. Filtration and drying under vacuo at 70° C. overnight gave a white solid which was identified as methyl 3-(3-hydrazino-3-oxopropyl)benzoate (38 mg, 8%) [$^1$H NMR (300 MHz, DMSO-d$_6$) δ 8.95 (s, 1H), 7.85 (d, J=7.9 Hz, 2H), 7.33 (d, J=7.9 Hz, 2H), 4.17 (s, 2H), 3.82 (s, 3H), 2.87 (t, J=7.7 Hz, 2H), 2.33 (t, J=7.7 Hz, 2H)]. And the filtrate was evaporated off under vacuo. The white residue was washed with MeOH and dryed under vacuo at 70° C. overnight to give 4-(3-hydrazino-3-oxopropyl)benzohydrazide (278 mg, 56%) [$^1$H NMR (300 MHz, DMSO-d$_6$) δ 9.66 (s, 1H), 8.94 (s, 1H), 7.71 (d, J=8.3 Hz, 2H), 7.25 (d, J=8.3 Hz, 2H), 4.43 (s, 2H), 4.14 (s, 2H), 2;84 (t, J=7.8 Hz, 2H), 2.32 (t, J=7.8 Hz, 2H)].

b) Preparation of methyl 4-{3-[2-(5-iodo-2-oxo-1,2-dihydro-3H-indol-3-ylidene)hydrazino]-3-oxopropyl}benzoate Following the general method as outlined in Example 1, into a suspension of 5-iodo-1H-indole-2,3-dione in acetic acid was added methyl 3-(3-hydrazino-3-oxopropyl)benzoate. After stirring at 100° C. the reaction mixture was cooled to rt and a yellow solid precipitated out. Filtration on a fritté, washing with AcOH, water and drying under vacuo at 60° C. overnight gave 42 mg of the title compound (60%) as a yellow powder in 86% purity by HPLC (R$_t$: 4.56, gradient of 8 min, MaxPlot detection between 230 and 400 nm).

M$^-$(APCI$^-$): 476.

Example 56

2-[(2-Chlorophenoxy)methyl]-N'-(5-iodo-2-oxo-1,2-dihydro-3H-indol-3-ylidene)-1,3-thiazole-4carbohydrazide Following the general method as outlined in Example 1, into a suspension of 5-iodo-1H-indole-2,3-dione in acetic acid was added 2-[(2-chlorophenoxy)methyl]-1,3-thiazole-4-carbohydrazide. After stirring at 100° C., the reaction mixture was cooled to rt and a yellow solid precipitated out. Filtration on a fritté, washing with AcOH, water and drying under vacuo at 60° C. overnight gave 47 mg of the title compound (79%) as a orange powder in 98.2% purity by HPLC (R$_t$: 5.07, gradient of 8 min, MaxPlot detection between 230 and 400 nm).

M$^-$(ESI (LC/MS)$^-$): 537; M$^+$(ESI (LC/MS)$^+$): 539.

Example 57

N'-(5-Iodo-2-oxo-1,2-dihydro-3H-indol-3-ylidene)-2-(2-phenyl[1,3]thiazolo-[3.2-b][1,2,4]triazol-6-yl)acetohydrazide Following the general method as outlined in Example 1, into a suspension of 5-iodo-1H-indole-2,3-dione in acetic acid was added 2-(2-phenyl[1,3]thiazolo[3,2-b][1,2,4]triazol-6-yl)acetohydrazide. After stirring at 100° C., the reaction mixture was cooled to rt and a yellow solid precipitated out. Filtration on a fritté, washing with AcOH, water and drying under vacuo at 60° C. overnight gave 28 mg of the title compound (48%) as a yellow powder in 94.7% purity by HPLC ($R_t$: 4.65, gradient of 8 min, MaxPlot detection between 230 and 400 nm).

M⁻(ESI (LC/MS)⁻): 527; M⁺(ESI (LC/MS)⁺): 529.

Example 58

4-{[3-Chloro-5-(trifluoromethyl)-2-pyridinyl]amino}-N'-[5-iodo-2-oxo-1,2-dihydro-3H-indol-3-ylidene]butanohydrazide Following the general method as outlined in Example 1, into a suspension of 5-iodo-1H-indole-2,3-dione in acetic acid was added 4-{[3-methyl-5-(trifluoromethyl)-2-pyridinyl]amino}butanohydrazide. After stirring at 100° C. the reaction mixture was cooled to rt and a yellow solid precipitated out. Filtration on a fritté, washing with AcOH, water and drying under vacuo at 60° C. overnight gave 5 mg of the title compound (8%) as a yellow powder in 98.1% purity by HPLC ($R_t$: 5.23, gradient of 8 min, MaxPlot detection between 230 and 400 nm).

M⁻(ESI (LC/MS)⁻): 550; M⁺(ESI (LC/MS)⁺): 552.

Example 59

2-{[3-Chloro-5-(trifluoromethyl)-2-pyridinyl]amino}-N'-(5-iodo-2-oxo-1,2-dihydro-3H-indol-3-ylidene)acetohydrazide Following the general method as outlined in Example 1, into a suspension of 5-iodo-1H-indole-2,3-dione in acetic acid was added 2-{[3-methyl-5-(trifluoromethyl)-2-pyridinyl]amino}acetohydrazide. After stirring at 100° C. the reaction mixture was cooled to rt and a yellow solid precipitated out. Filtration on a fritté, washing with AcOH, water and drying under vacuo at 60° C. overnight gave 38 mg of the title compound (66%) as a orange powder in 98.5% purityby HPLC ($R_t$: 5.1, gradient of 8 min, MaxPlot detection between 230 and 400 nm).

M⁻(ESI (LC/MS)⁻): 522; M⁺(ESI (LC/MS)⁺): 524.

Example 60

1-Benzoyl-N'-(5-iodo-2-oxo-1,2-dihydro-3H-indol-3-ylidene)-4-piperidinecarbohydrazide a) Preparation of (±)-1-benzoyl-4-piperidinecarbohydrazide (Scheme 2, compound B)

To a suspension of (±)-methyl 1-benzoyl-4-piperidinecarboxylate (502 mg, 2.03 mmol) in MeOH (10 mL) was added hydrazine hydrate (1.6 mL). After stirring for 24 h at rt, the reaction mixture and water (40 mL) was added. After washing with Et₂O (2×20 mL), the aqueous layer was evaporated off under vacuo. The title compound was obtained as an amorphous beige solid (469 mg, 93%) in a 91.0% purity by HPLC (MaxPlot detection between 230 and 400 nm).

$^1$H NMR (300 MHz, DMSO-$d_6$) δ 9.01 (s, 1H), 7.43 (m, 3H), 7.35 (m, 2H), 4.60-3.20 (m, 4H), 3.10-2.65 (m, 2H), 2.34 (m, 1H), 1.81-1.52 (m, 4H).

b) Preparation of 1-Benzoyl-N'-(5-iodo-2-oxo-1,2-dihydro-3H-indol-3-ylidene)-4-piperidinecarbohydrazide Into a suspension of 5-iodo-1H-indole-2,3-dione in acetic acid was added (±)-1-benzoyl-4-piperidinecarbohydrazide. After stirring at 100° C. the reaction mixture was cooled to rt and a yellow solid precipitated out. Filtration on a fritté, washing with AcOH, water and drying under vacuo at 60° C. overnight gave 221 mg of the title compound (88%) as a yellow solid in 94.1% purity by HPLC ($R_t$: 3.93, gradient of 8 min, MaxPlot detection between 230 and 400 nm).

M.p. 160° C.
M⁻(APCI⁻): 501; M⁺(APCI⁺): 503.

Example 61

N-(4-{[2-(5-Iodo-2-oxo-1,2-dihydro-3H-indol-3-ylidene)hydrazino]-carbonyl}phenyl)-2-phenoxyacetamide a) Preparation of N-[4-(hydrazinocarbonyl)phenyl]-2-phenoxyacetamide (Scheme 2, compound B)

To a suspension of methyl 4-[(phenoxyacetyl)amino]benzoate (843 mg, 2.95 mmol) in EtOH (10 mL) was added hydrazine hydrate (2.15 mL). After stirring for 15 hrs at reflux, the reaction mixture was cooled to rt. Water (10 mL) was added to the reaction mixture and a white solid precipitated out. Filtration, washing with EtOH/water (2×2 mL) and water (3×1 mL), and drying under vacuo at 70° C. for 6 hrs gave 389 mg of the title compound (46%) as a white solid in 95.4% purity by HPLC (MaxPlot detection between 230 and 400 nm).

$^1$H NMR (DMSO-$d_6$, 300 MHz) δ 10.28 (s, 1H), 9.65 (s, 1H), 7.79 (d, J=8.3 Hz, 2H), 7.69 (d, J=8.3 Hz, 2H), 7.31 (m, 2H), 6.98 (m, 3H), 4.71 (s, 2H), 4.42 (s, 2H).

b) Preparation of N-(4-{[2-(5-Iodo-2-oxo-1,2-dihydro-3H-indol-3-ylidene)hydrazino]-carbonyl}phenyl)-2-phenoxyacetamide Following the general method as outlined in Example 1, into a suspension of 5-iodo-1H-indole-2,3-dione in acetic acid was added N-[4-(hydrazinocarbonyl)phenyl]-2-phenoxyacetamide. After stirring at 100° C. the reaction mixture was cooled to rt and a yellow solid precipitated out. Filtration on a fritté, washing with AcOH, water and drying under vacuo at 60° C. overnight gave 222 mg of the title compound (82%) as a yellow solid in 98.1% purity by HPLC ($R_t$: 4.41, gradient of 8 min, MaxPlot detection between 230 and 400 nm).

M.p. 305° C. (decomp).
$^1$H NMR (DMSO-$d_6$, 300 MHz) δ 13.82 (s, 1H), 11.46 (s, 1H), 10.50 (s, 1H), 7.87(s, 4H), 7.83 (br s, 1H), 7.71 (dd, J=8.3, 1.5 Hz, 1H), 7.31 (m, 2H), 6.98 (m, 3H), 6.81 (d, J=8.3 Hz, 1H), 4.75 (s, 2H).
M⁻(APCI⁻): 539; M⁺(APCI⁺): 541.

Example 62

N-(4-{[2-(5-Iodo-2-oxo-1,2-dihydro-3H-indol-3-ylidene)hydrazino]-carbonyl}phenyl)nicotinamide Following the general method as outlined in Example 1, into a suspension of 5-iodo-1H-indole-2,3-dione in acetic acid was added N-[4-hydrazinocarbonyl)phenyl]nicotinamide. After stirring at 100° C. the reaction mixture was cooled to rt and a yellow solid precipitated out. Filtration on a fritté, washing with AcOH, water and drying under vacuo at 60° C. overnight gave 181 mg of the title compound (71%) as a orange solid in 96.8% purity by HPLC ($R_t$: 3.01, gradient of 8 min, MaxPlot detection between 230 and 400 nm).

M.p. 344° C. (decomp).

$^1$H NMR (DMSO-$d_6$, 300 MHz) δ 13.85 (s, 1H), 11.47 (s, 1H), 10.81 (s, 1H), 9.13 (d, J=1.9 Hz, 1H), 8.78 (dd, J=4.9, 1.5 Hz, 1H), 8.32 (dd,d, J=7.9, 1.9, 1.5 Hz, 1H), 8.01 (d, J=8.7 Hz, 2H), 7.92 (d, J=8.7 Hz, 2H), 7.83 (br s, 1H), 7.72 (dd, J=7.9, 1.5 Hz, 1H), 7.59 (dd, J=7.9,4.9 Hz, 1H), 6.82 (d, J=7.9 Hz, 1H).

M$^-$(APCI$^-$): 510; M$^+$(APCI$^+$): 512.

Example 63

3-(Nitro)-N-(4-{[2-(5-iodo-2-oxo-1,2-dihydro-3H-indol-3-ylidene)-hydrazino]carbonyl}benzyl)benzamide a) Preparation of methyl 4-{[(3-nitrobenzoyl)amino]methyl}benzoate (Sheme 2, compound C)

Under an inert atmosphere, to a stirred solution of methyl 4-(aminomethyl)benzoate (50 g, 0.436 mol) and TEA (210 mL, 1.5 mol) in anhydrous DCM (1.0 L) was added a solution of freshly prepared 3-nitro benzoyl chloride (0.59 mol) in DCM (250 mL). The resulting mixture was allowed to stir for 2 hrs. The reaction was quenched with a 10% aqueous solution of sodium hydrogenocarbonate. The organic layer was washed with a 1.5N HCl solution and water. After drying over MgSO$_4$ and evaporation of the solvent in vacuo, a solid was obtained and purified by flash chromatography to give the title compound (50 g) in a 52% yield as a white powder.

$^1$H NMR (300 MHz, DMSO-$d_6$) δ 9.51 (t, J=5.7 Hz, 1H), 8.73 (t, J=1.9 Hz, 1H), 8.41 (ddd, J=8.3, 2.0, 0.7 Hz, 1H), 8.34 (d, J=7.9 Hz, 1H), 7.93 (d, J=8.3 Hz, 2H), 7.79 (t, J=8.1 Hz, 1H), 7.47 (d, J=8.3 Hz, 2H), 4.59 (d, J=5.7Hz, 2H), 3.83 (s, 3H).

b) Preparation of N-[4-(hydrazinocarbonyl)benzyl]-3-nitrobenzamide (Sheme 2, compound B)

To a suspension of 4-{[(3-nitrobenzoyl)amino]methyl}benzoate (500 mg, 1.59 mmol) in EtOH (6 mL) was added hydrazine hydrate (1.16 mL). After stirring for 15 h at reflux, the reaction mixture was cooled to rt and a white solid precipitated out. Filtration, washing with EtOH (2×2 mL), EtOH/water (2×2 mL) and water (2×2 mL), and drying under vacuo at 70° C. for 5 hrs gave 379 mg of the title compound (76%) as a pale yellow solid in 96.5% purity by HPLC (MaxPlot detection between 230 and 400 nm).

$^1$H NMR (300 MHz, DMSO-$d_6$) δ 9.71 (s, 1H), 9.47 (t, J=5.7 Hz, 1H), 8.73 (s, 1H), 8.40 (d, J=8.3 Hz, 1H), 8.33 (d, J=7.5 Hz, 1H), 7.79 (m, 3H), 7.39 (d, J=8.3 Hz, 2H), 4.55 (d, J=5.7 Hz, 2H), 4.45 (s, 2H).

c) Preparation of 3-(Nitro)-N-(4-{[2-(5-iodo-2-oxo-1,2-dihydro-3H-indol-3-ylidene)-hydrazino]carbonyl}benzyl)benzamide Into a suspension of 5-iodo-1H-indole-2,3-dione in acetic acid was added N-[4-(hydrazinocarbonyl)benzyl]-3-nitrobenzamide. After stirring at 100° C. the reaction mixture was cooled to rt and a yellow solid precipitated out. Filtration on a fritté, washing with AcOH, water and drying under vacuo at 60° C. overnight gave 252 mg of the title compound (89%) as a orange solid in 95.4% purity by HPLC ($R_t$: 4.15, gradient of 8 min, MaxPlot detection between 230 and 400 nm).

M.p. 331° C. (decomp).

$^1$H NMR (DMSO-$d_6$, 300 MHz) δ 13.82 (s, 1H), 11.46 (s, 1H), 9.54 (t, J=5.6 Hz, 1H), 8.75 (br s, 1H), 8.40 (dd, J=7.9, 1.2 Hz, 1H), 8.35 (d, J=8.0 Hz, 1H), 7.87 (d, J=8.3 Hz, 2H), 7.83 (br s, 1H), 7.80 (dd, J=8.0, 7.9 Hz, 1H), 7.71 (dd, J=8.3, 1.5 Hz, 1H), 7.57 (d, J=8.3 Hz, 2H), 6.80 (d, J=8.3 Hz, 1H), 4.61 (d, J=5.6 Hz, 2H).

M$^-$(APCI$^-$): 568; M$^+$(APCI$^+$): 570.

Example 64

N-(4-{[2-(5-Iodo-2-oxo-1,2-dihydro-3H-indol-3-ylidene)hydrazino]-carbonyl}phenyl)[1,1'-biphenyl]-4-carboxamide a) Preparation of N-[4-(hydrazinocarbonyl)phenyl][1,1'-biphenyl]-4-carboxamide (Scheme 2, compound B)

To a suspension of methyl 4-[([1,1'-biphenyl]-4-ylcarbonyl)amino]benzoate (880 mg, 2.66 mmol) in EtOH (10 mL) was added hydrazine hydrate (1.8 mL). After stirring for 7 days at reflux, the reaction mixture was cooled to rt and a white solid precipitated out. Filtration, washing with EtOH (3×2 mL) and water (3×2 mL), and drying under vacuo at rt for 6 hrs gave 585 mg of the title compound (66%) as a white solid in 96.4% purity by HPLC (MaxPlot detection between 230 and 400 nm).

$^1$H NMR (DMSO-$d_6$, 300 MHz) δ 10.48 (s, 1H), 9.67 (s, 1H), 8.06 (d, J=8.6 Hz, 2H), 7.85 (m, 6H), 7.76 (m, 2H), 7.51 (m, 2H), 7.42 (m, 1H), 4.46 (s, 2H).

b) Preparation of N-(4-{[2-(5-Iodo-2-oxo-1,2-dihydro-3H-indol-3-ylidene)hydrazino]-carbonyl}phenyl)[1,1'-biphenyl]-4-carboxamide (Compound C of Scheme 2)

Following the general method as outlined in Example 1, into a suspension of 5-iodo-1H-indole-2,3-dione in acetic acid was added N-[4-(hydrazinocarbonyl)phenyl][1,1'-biphenyl]-4-carboxamide. After stirring at 100° C. the reaction mixture was cooled to rt and a yellow solid precipitated out. Filtration on a fritté, washing with AcOH, water and drying under vacuo at 60° C. overnight gave 243 mg of the title compound (83%) as a yellow powder in 95.7% purity by HPLC ($R_t$: 5.34, gradient of 8 min, MaxPlot detection between 230 and 400 nm).

M.p. 349° C. (decomp).

$^1$H NMR (DMSO-$d_6$, 300 MHz) δ 13.85 (s, 1H), 11.47 (s, 1H), 10.67 (s, 1H); 8.08 (d, J=8.3 Hz, 2H), 8.04 (d, J=8.8 Hz, 2H), 7.91 (d, J=8.8 Hz, 2H), 7.86 (m, 3H), 7.76 (m, 2H), 7.71 (dd, J=8.3, 1.9 Hz, 1H), 7.51 (m, 2H), 7.42 (m, 1H), 6.82 (d, J=8.3 Hz, 1H).

M$^-$(APCI$^-$): 585; M$^+$(APCI$^+$): 587.

Example 65

Methyl 3-{2-[2-(5-iodo-2-oxo-1,2-dihydro-3H-indol-3-ylidene)hydrazino]-2-oxoethoxy}benzoate a) Preparation of methyl 3-(2-hydrazino-2-oxoethoxy)benzoate (Compound C of Scheme 2)

To a suspension of methyl 3-(2-methoxy-2-oxoethoxy) benzoate (887 mg, 3.96 mmol) in MeOH (50 mL) was added hydrazine hydrate (1.92 mL). After stirring for 0.5 h at rt, water (50 mL) was added and the reaction mixture was filtered. Washing with water (3×5 mL) and drying under vacuo at 70° C. overnight gave 713 mg of the title compound (80%) as a white solid in 98.3% purity by HPLC (MaxPlot detection between 230 and 400 nm).

$^1$H NMR (DMSO-$d_6$, 300 MHz) δ 9.38 (s, 1H), 7.56 (d, J=7.5 Hz, 1H), 7.50 (br s, 1H), 7.44 (dd, J=8.3, 7.5 Hz, 1H), 7.24 (dd, J=8.3, 1.5 Hz, 1H), 4.55 (s, 2H), 4.32 (s, 2H), 3.84 (s, 3H).

b) Preparation of methyl 3-{2-[2-(5-Iodo-2-oxo-1,2-dihydro-3H-indol-3-ylidene)-hydrazino]-2-oxoethoxy}benzoate Following the general method as outlined in Example 1, into a suspension of 5-iodo-1H-indole-2,3-dione in acetic acid was added methyl 3-(2-hydrazino-2-oxoethoxy)benzoate. After stirring at 100° C. the reaction mixture was cooled to rt and a yellow solid precipitated out. Filtration on a fritté, washing with AcOH, water and drying under vacuo at 60° C. overnight gave 380 mg of the title compound (79%) as a orange powder in 98.9% purity by HPLC ($R_t$: 4.3, gradient of 8 min, MaxPlot detection between 230 and 400 nm).

M.p. 237° C.

IR (neat) ν 3173, 1715, 1690, 1431, 1243, 1206, 1137, 752 cm$^{-1}$.

$^1$H NMR (DMSO-$d_6$, 300 MHz) δ 13.64 (br s, 0.6), 12.48 (br s, 0.4H), 11.36 (s, 1H), 7.82 (br s, 1H), 7.70 (dd, J=8.3, 1.9 Hz, 1H), 7.62-7.46 (m, 3H), 7.33 (m, 1H), 6.79 (d, J=8.3 Hz, 1H), 5.40 (br s, 0.8H), 4.97 (br s, 1.2 H), 3.85 (s, 3H).

M$^-$(APCI$^-$): 478; M$^+$(APCI$^+$): 480.

Example 66

Methyl 4-{[[2-(5-Iodo-2-oxo-1,2-dihydro-3H-indol-3-3-ylidene)hydrazino]-(oxo)acetyl]amino}benzoate a) Preparation of methyl 3-{[methoxy(oxo)acetyl]amino}benzoate (Compound C of Scheme 2)

To a solution of methyl 4-aminobenzoate (500 mg, 3.31 mmol) in anydrous pyridine (10 mL) was added dropwise methyl chlorooxoacetate (370 μL, 3.97 mmol) at 0° C. After 5 min the temperature was allowed to warm up to rt. After 90 min, aminomethyl resin (Polymers Laboratories PL-AMS, 1.96 mmol/g, 720 mg) was added and the resulting mixture was stirred overnight at rt. After filtration and rinsing the resin, water (50 mL) was added into the filtrate and a white solid precipated out. Filtration and washing with water gave a solid which was dried under vacuo at 70° C. for 5 hrs. The title compound (554 mg) was obtained as a white solid (71%) in 99.6% purity by HPLC (MaxPlot detection between 230 and 400 nm).

$^1$H NMR (300 MHz, DMSO-$d_6$) δ 11.09 (s, 1H), 7.95 (d, J=8.6 Hz, 2H), 7.90 (d, J=8.6 Hz, 2H), 3.85 (s, 3H), 3.82 (s, 3H).

b) Preparation of methyl 3-{[hydrazino(oxo)acetyl]amino}benzoate (Scheme 2, compound B):

To a suspension of methyl 3-{[methoxy(oxo)acetyl]amino}benzoate (100 mg, 0.42 mmol) in MeOH (8 mL) was added hydrazine hydrate (0.2 mL). After stirring for 0.5 h at rt, the reaction mixture was filtered. Washing with MeOH (2×1 mL) and water (3×1 mL) and drying under vacuo at 70° C. for 2 hrs gave 82 mg of the title compound (82%) as a white solid in 97.1% purity by HPLC (MaxPlot detection between 230 and 400 nm).

$^1$H NMR (DMSO-$d_6$, 300 MHz) δ 10.91 8s, 1H), 10.33 (s, 1H), 7.97 (d, J=9.0 Hz, 2H), 7.92 (d, J=9.0 Hz, 2H), 4.64 (s, 2H), 3.82 (s, 3H).

c) Preparation of Methyl 4-{[[2-(5-iodo-2-oxo-1,2-dihydro-3H-indol-3-ylidene)hydrazino]-(oxo)acetyl]amino}benzoate Into a suspension of 5-iodo-1H-indole-2,3-dione in acetic acid was added methyl 3-{[hydrazino(oxo)acetyl]amino}benzoate. After stirring at 100° C. the reaction mixture was cooled to rt and a yellow solid precipitated out. Filtration on a fritté, washing with AcOH, water and drying under vacuo at 60° C. overnight gave 123 mg of the title compound (83%) as a orange solid in 94.45% purity by HPLC ($R_t$: 4.19, gradient of 8 min, MaxPlot detection between 230 and 400 nm).

M.p. 364° C. (decomp).

$^1$H NMR (DMSO-$d_6$, 300 MHz) δ 14.15 (s, 1H), 11.43 (s, 1H), 11.36 (s, 1H), 8.00 (m, 4H), 7.86 (s, 1H), 7.74 (d, J=7.9 Hz, 1H), 6.80 (d, J=7.9 Hz, 1H), 3.83 (s, 3H).

M$^-$(APCI$^-$): 491.

Example 67

3-(1,3-Benzodioxol-5-yl)-N-(4-{[2-(5-iodo-2-oxo-1,2-dihydro-3H-indol-3-ylidene)hydrazino]carbonyl}phenyl)propanamide a) Preparation of methyl 4-{[3-(1,3-benzodioxol-5-yl)propanoyl]amino}benzoate (Compound C of Scheme 2)

To a solution of 3-(3,4-methylenedioxyphenyl)-propionic acid (501 mg, 2.58 mmol) in anhydrous THF (10 mL) were added N-methylmorpholine (0.28 mL, 2.58 mmol) and isobutylchloroformate (0.33 mL, 2.58 mmol) at 0° C. After 30 min, at 0° C., a solution of methyl 4-aminobenzoate (390 mg, 2.58 mmol) in anhydrous THF (2 mL) was added to the reaction mixture. After 30 min the temperature was allowed to warm up to rt and stir for 24 hrs. After extraction with EtOAc (100 mL), washing with HCl (0.1N, 50 mL) and a saturated aqueous solution of NaHCO$_3$ (50 mL), the organic layer was dryed over sodium sulfate and evaporated under vacuo to give a solid. The residue was taken up in Et$_2$O, filtrated and washed with Et$_2$O gave the title compound as a white solid (62%) in a 99.4% purity by HPLC (MaxPlot detection between 230 and 400 nm).

$^1$H NMR (DMSO-$d_6$, 300 MHz) δ 10.22 (s, 1H), 7.89 (d, J=8.7 Hz, 2H), 7.70 (d, J=8.7 Hz, 2H), 6.82 (d, J=1.6 Hz, 1H), 6.80 (d, J=7.9 Hz, 1H), 6.68 (dd, J=7.9, 1.6 Hz, 1H), 5.94 (s, 2H), 3.80 (s, 3H), 2.82 (t, J=7.5 Hz, 2H), 2.61 (t, J=7.5 Hz, 2H).

b) Preparation of 3-(1,3-benzodioxol-5-yl)-N-[4-hydrazinocarbonyl)phenyl]propanamide (Scheme 2, compound B)

To a suspension of methyl 4-{[3-(1,3-benzodioxol-5-yl)propanoyl]amino}benzoate (200 mg, 0.61 mmol) in EtOH (3.5 mL) was added hydrazine hydrate (0.5 mL). After stirring for 15 hrs at reflux, the reaction mixture was cooled to rt and a white solid precipitated out. Filtration, washing with EtOH (2×1 mL) and water (3×1 mL), and drying under vacuo at 70° C. for 1 hr gave 130 mg of the title compound (65%) as a white solid in 95.5% purity by HPLC (MaxPlot detection between 230 and 400 nm). $^1$H NMR (DMSO-$d_6$, 300 MHz) δ 10.08 (s, 1H), 9.60 (s, 1H), 7.75 (d, J=8.5 Hz, 2H), 7.61 (d, J=8.5 Hz, 2H), 6.82 (d, J=1.5 Hz, 1H), 6.80 (d, J=7.9 Hz, 1H), 6.68 (dd, J=7.9, 1.5 Hz, 1H), 5.94 (s, 2H), 4.41 (s, 2H), 2.82 (t, J=7.6 Hz, 2H), 2.59 (t, J=7.6 Hz, 2H).

c) Preparation of 3-(1,3-Benzodioxol-5-yl)-N-(4-{[2-(5-iodo-2-oxo-1,2-dihydro-3H-indol-3-ylidene)hydrazino]carbonyl}phenyl)propanamide Into a suspension of 5-iodo-1H-indole-2,3-dione in acetic acid was added 3-(1,3-benzodioxol-5-yl)-N-[4-(hydrazinocarbonyl)phenyl]propanamide. After stirring at 100° C. the reaction mixture was cooled to rt and a yellow solid precipitated out. Filtration on a fritté, washing with AcOH, water and drying under vacuo at 60° C. overnight gave 97 mg of the title compound (76%) as a yellow solid in 98.8% purity by HPLC ($R_t$: 4.33, gradient of 8 min, MaxPlot detection between 230 and 400 nm).

M.p. 314° C. (decomp.).

IR (neat) v (cm$^{-1}$) 3188, 1720, 1655, 1593, 1488, 1245, 1119, 1039, 918 and 812.

$^1$H NMR (DMSO-$d_6$, 300 MHz) δ 13.81 (s, 1H), 11.45 (s, 1H), 10.29 (s, 1H), 7.82 (m, 5H), 7.71 (dd, J=8.3, 1.5 Hz, 1H), 6.81 (m, 3H), 6.70 (dd, J=7.9, 1.1 Hz, 1H), 5.95 (s, 2H), 2.84 (t, J=7.5 Hz, 2H), 2.63 (t, J=7.5 Hz, 2H).

M$^-$(ESI (LC/MS)$^-$): 581; M$^+$(ESI (LC/MS)$^+$): 583.

Example 68

4-[(4-{[2-(5-Iodo-2-oxo-1,2-dihydro-3H-indol-3-ylidene)hydrazino]-carbonyl}benzoyl)amino]benzoic acid a) Preparation of 4-{[4-(methoxycarbonyl)benzoyl]amino}benzoic acid (Compound C of Scheme 2)

To a solution of 4-aminobenzoic acid (500 mg, 3.65 mmol) in anhydrous THF (20 mL) were added DIEA (1.36 mL, 8.02 mmol) and tert-butyldimethylchlorosilane (4 mL, 1M in THF). The resulting mixture was allowed to stir at rt for 45 min. A solution of terephtalic acid monomethyl ester chloride (800 mg, 4 mmol) in THF (5 mL) was added and the resulting mixture was stirred for 90 min at rt until the disappearance of the starting material and finally TBAF (4 mL, 1M in THF) was added. After 25 min at rt, the reaction was quenched with a solution of 0.1N HCl (100 mL). Extraction with EtOAc (3×200 mL), drying over sodium sulfate and evaporation under vacuo gave a pale yellow solid. Washing with hot EtOH (50 mL) gave the tilte compound as a white solid (698 mg, 64%) in a 84% purity by HPLC (MaxPlot detection between 230 and 400 nm).

$^1$H NMR (DMSO-$d_6$, 300 MHz) δ 12.77 (s, 1H), 10.71 (s, 1H), 8.09 (m, 4H), 7.95 (d, J=9.0 Hz, 2H), 7.91 (d, J=9.0 Hz, 2H), 3.89 (s, 3H).

b) Preparation of 4-{[4-(hydrazinocarbonyl)benzoyl]amino}benzoic acid (Scheme 2, compound B)

To a suspension of 4-{[4-(methoxycarbonyl)benzoyl]amino}benzoic acid (300 mg g, 1 mmol) in EtOH (4.5 mL) was added hydrazine hydrate (0.73 mL). After stirring for 15 h at reflux, the reaction mixture was cooled to rt and a white solid precipitated out. Filtration, washing with EtOH (3×1 mL) and drying under vacuo at 70° C. for 2 hrs gave a white solid. This residue was taken up in water (25 mL) and AcOH (5 mL) was added. A white solid precipitated out which was further washed with water (3×2 mL). Drying at 80° C. for 1 hr gave 220 mg of the title compound (73%) as a white solid in 91.2% purity by HPLC (MaxPlot detection between 230 and 400 nm).

$^1$H NMR (DMSO-$d_6$, 300 MHz) δ10.61 (s, 1H), 9.95 (s, 1H), 8.02 (d, J=8.3 Hz, 2H), 7.96 (d, J=8.3 Hz, 2H), 7.93 (s, 4H).

c) Preparation of 4-[(4-{[2-(5-Iodo-2-oxo-1,2-dihydro-3H-indol-3-ylidene)hydrazino]-carbonyl}benzoyl)amino]benzoic acid Into a suspension of 5-iodo-1H-indole-2,3-dione in acetic acid was added 4-{[4-(hydrazinocarbonyl)benzoyl]amino}benzoic acid. After stirring at 100° C. the reaction mixture was cooled to rt and a yellow solid precipitated out. Filtration on a fritté, washing with AcOH, water and drying under vacuo at 60° C. overnight gave 126 mg of the title compound (75%) as a orange solid in 83.3% purity by HPLC ($R_t$: 3.78, gradient of 8 min. MaxPlot detection between 230 and 400 nm).

$^1$H NMR (DMSO-$d_6$, 300 MHz) δ 13.88 (br s, 1H), 12.64 (br s, 1H), 11.49 (s, 1H), 10.73 (s, 1H), 8.14-7.85 (m, 9H), 7.73 (d, J=7.1 Hz, 1H), 6.82 (d, J=7.1 Hz, 1H).

M$^-$(ESI (LC/MS)$^-$): 553; M$^+$(ESI (LC/MS)$^+$): 555.

Example 69

3-(3,4-Dihydroxyphenyl)-N-(4-{[2-(5-iodo-2-oxo-1,2-dihydro-3H-indol-3-ylidene)hydrazino]carbonyl}phenyl)propanamide a) Preparation of methyl 4-{[3-(3,4-dihydroxyphenyl)propanoyl]amino}benzoate (Compound C of Scheme 2)

To a solution of 3,4-dihydroxyhydrocinnamic acid (723 mg, 3.97 mmol) in anhydrous THF (20 mL) were added N-methylmorpholine (0.44 mL, 3.97 mmol) and isobutylchloroformate (0.52 mL, 3.97 mmol) at 0° C. After 45 min, at 0° C., a solution of methyl 4-aminobenzoate (500 mg, 3.31 mmol) in anhydrous THF (4 mL) was added to the reaction mixture. After 5 min the temperature was allowed to warm up to rt and stir overnight. After extraction with EtOAc (100 mL), washing with HCl (0.1N, 50 mL) and a saturated aqueous solution of NaHCO$_3$ (50 mL), the organic layer was dried over sodium sulfate and evaporated under vacuo to give a yellow oil. Purification by flash chromatography using DCM/MeOH (95/5) as eluant gave the title compound as a colourless oil (22%) in a 94.8% purity by HPLC (MaxPlot detection between 230 and 400 nm).

¹H NMR (DMSO-d₆, 300 MHz) δ 10.21 (s, 1H), 8.68 (s, 2H), 7.89 (d, J=8.8 Hz, 2H), 7.71 (d, J=8.8 Hz, 2H), 6.61 (m, 2H), 6.46 (dd, J=8.0, 1.8 Hz, 1H), 3.80 (s, 3H), 2.72 (t, J=7.4 Hz, 2H), 2.56 (t, J=7.4 Hz, 2H).

b) Preparation of 3-(3,4-dihydroxyphenyl)-N-[4-(hydrazinocarbonyl)phenyl]propanamide (Scheme 2, compound B)

To a suspension of methyl 4-{[3-(3,4-dihydroxyphenyl)propanoyl]amino}benzoate (227 mg, 0.72 mmol) in EtOH (3.5 mL) was added hydrazine hydrate (0.55 mL). After stirring for 15 h at reflux, the reaction mixture was cooled to rt and a white solid precipitated out. Filtration, washing with EtOH (2×1 mL) and water (3×1 mL) and drying under vacuo at 70° C. for 2 hrs gave 117 mg of the title compound (52%) as a white solid in 99.6% purity by HPLC (MaxPlot detection between 230 and 400 nm).

¹H NMR (DMSO-d₆, 300 MHz) δ 10.07 (s, 1H), 9.61 (s, 1H), 8.65 (s, 4H), 7.75 (d, J=8.7 Hz, 2H), 7.61 (d, J=8.7 Hz, 2H), 6.60 (m, 2H), 6.46 (dd, J=7.9, 1.5 Hz, 1H), 4.41 (s, 2H), 2.72 (t, J=7.5 Hz, 2H), 2.54 (t, J=7.5 Hz, 2H).

c) Preparation of 3-(3,4-Dihydroxyphenyl)-N-(4-{[2-(5-iodo-2-oxo-1,2-dihydro-3H-indol-3-ylidene)hydrazino]carbonyl}phenyl)propanamide Into a suspension of 5-iodo-1H-indole-2,3-dione in acetic acid was added 3-(3,4-dihydroxyphenyl)-N-[4-(hydrazinocarbonyl)phenyl]propanamide. After stirring at 100° C. the reaction mixture was cooled to rt and a yellow solid precipitated out. Filtration on a fritté, washing with AcOH, water and drying under vacuo at 60° C. overnight gave 161 mg of the title compound (87%) as a yellow solid in 96% purity by HPLC (R_t: 3.56, gradient of 8 min, MaxPlot detection between 230 and 400 nm).

¹H NMR (DMSO-d₆, 300 MHz) δ 13.81 (s, 1H), 11.45 (s, 1H), 10.28 (s, 1H), 8.74 (s, 0.4H), 8.73 (s, 0.6H), 8.64 (s, 0.4H), 8.63 (s, 0.6H), 7.82 (m, 5H), 7.71 (dd, J=8.3, 1.5 Hz, 1H), 6.81 (d, J=8.3 Hz, 1H), 6.61 (m, 2H), 6.47 (d, J=7.9 Hz, 1H), 2.74 (t, J=7.4 Hz, 2H), 2.58 (t, J=7.4 Hz, 2H).

M⁻(ESI (LC/MS)⁻): 569.

Example 70

3-(3-Hydroxyphenyl)-N-(4-{[2-(5-iodo-2-oxo-1,2-dihydro-3H-indol-3-ylidene)hydrazino]carbonyl}phenyl)propanamide a) Preparation of methyl 4-{[3-(3-hydroxyphenyl)propanoyl]amino}benzoate (Compound C of Scheme 2)

To a solution of 3-(3-hydroxyphenyl)-propionic acid (198 mg, 1.19 mmol) in anhydrous THF (5 mL) were added N-methylmorpholine (1.2 equiv.) and isobutylchloroformate (1.2 equiv.) at 0° C. After 30 min, at 0° C., a solution of methyl 4-aminobenzoate (150 mg, 0.99 mmol) in anhydrous THF (1 mL) was added to the reaction mixture. After 5 min the temperature was allowed to warm up to rt and stir overnight. After extraction with EtOAc (100 mL), washing with HCl (0.1N, 50 mL) and a saturated aqueous solution of NaHCO₃ (50 mL), the organic layer was dryed over sodium sulfate and evaporated under vacuo to give a yellow oil. Purification by flash chromatography using EtOAc/cyclohexane as eluant and recrystallization from DCM/MeOH/TEA (10/0.4/0.1) gave the title compound as a white solid (32%) in 98.9% purity by HPLC (MaxPlot detection between 230 and 400 nm).

¹H NMR (300 MHz, DMSO-d₆) δ 10.24 (s, 1H), 9.25 (s, 1H), 7.89 (d, J=8.6 Hz, 2H), 7.71 (d, J=8.6 Hz, 2H), 7.05 (m, 1H), 6.64 (m, 2H), 6.56 (m, 1H), 3.80 (s, 3H), 2.81 (m, 2H), 2.61 (m, 2H).

b) Preparation of N-[4-hydrazinocarbonyl)phenyl]-3-(3-hydroxyphenyl)propanamide Compound C of Scheme 2)

To a suspension of methyl 4-{[3-(3-hydroxyphenyl)propanoyl]amino}benzoate (95 mg, 0.32 mmol) in EtOH (3 mL) was added hydrazine hydrate (0.9 mL). After stirring for 21 hrs at reflux, the reaction mixture was cooled to rt and a white solid precipitated out. Filtration, washing with water (3×1 mL), and drying under vacuo at 70° C. for 1 hr gave 46 mg of the title compound (480%) as a white solid in 91% purity by HPLC (MaxPlot detection between 230 and 400 nm).

¹H NMR (DMSO-d₆, 300 MHz) δ 10.09 (s, 1H), 9.61 (s, 1H), 9.25 (s, 1H), 7.75 (d, J=7.8 Hz, 2H), 7.62 (d, J=7.8 Hz, 2H), 7.05 (m, 1H), 6.59 (m, 3H), 4.40 (s, 2H), 2.81 (m, 2H), 2.59 (m, 2H).

c) Preparation of 3-(3-Hydroxyphenyl)-N-(4-{[2-(5-iodo-2-oxo-1,2-dihydro-3H-indol-3-ylidene)hydrazino]carbonyl}phenyl)propanamide Into a suspension of 5-iodo-1H-indole-2,3-dione in acetic acid was added N-[4-(hydrazinocarbonyl)phenyl]-3-(3-hydroxyphenyl)propanamide. After stirring at 100° C., the reaction mixture was cooled to rt and a yellow solid precipitated out. Filtration on a fritté, washing with AcOH, water and drying under vacuo at 60° C. overnight gave 45 mg of the title compound (63%) as a yellow solid in 92.4% purity by HPLC (R_t: 3.88, gradient of 8 min, MaxPlot detection between 230 and 400 nm).

¹H NMR (DMSO-d₆, 300 MHz) δ 13.81 (s, 1H), 11.45 (s, 1H), 10.31 (s, 1H), 9.26 (s, 1H), 7.82 (m, 5H), 7.71 (d, J=7.9 Hz, 1H), 7.06 (m, 1H), 6.81 (d, J=7.9 Hz, 1H), 6.65 (m, 2H), 6.57 (d, J=8.3 Hz, 1H), 2.83 (t, J=7.1 Hz, 2H), 2.64 (t, J=7.1 Hz, 2H).

M⁻(ESI (LC/MS)⁻): 553; M⁺(ESI (LC/MS)⁺): 555.

Example 71

4-Nitro-N'-(5-bromo-2-oxo-1,2-dihydro-3H-indol-3-ylidene)benzohydrazide

Following the general method as outlined in Example 1, into a suspension of 5-bromo-1H-indole-2,3-dione in acetic acid was added 4-nitrobenzohydrazide. After stirring at 100° C. the reaction mixture was cooled to rt and a yellow solid precipitated out. Filtration on a fritté, washing with AcOH, water and drying under vacuo at 60° C. overnight gave 165 mg of the title compound (85%) as a orange solid in 95.3% purity by HPLC (R_t: 4.80, 5.53, gradient of 10 min, MaxPlot detection between 230 and 400 nm).

M.p. 341° C. (decomp).
M⁺(APCI⁺): 389.

Example 72

Methyl 4-{2-[2-(5-bromo-2-oxo-1,2-dihydro-3H-indol-3-ylidene)hydrazino]-2-oxoethoxy}benzoate Following the general method as outlined in Example 1, into a suspension of 5-bromo-1H-indole-2,3-dione in acetic acid was added methyl 4(2-hydrazino-2-oxoethoxy)benzoate. After stirring at 100° C., the reaction mixture was cooled to rt and a yellow solid precipitated out. Filtration on a fritté, washing with AcOH, water and drying under vacuo at 60° C. overnight gave 86 mg of the title compound (80%) as a orange powder in 94% purity by HPLC (R$_t$: 4.17, gradient of 8 min, MaxPlot detection between 230 and 400 nm).

M$^-$(APCI$^-$): 432.

Example 73

4-Methoxy-N'-(5-bromo-2-oxo-1,2-dihydro-3H-indol-3-ylidene)benzohydrazide

Following the general method as outlined in Example 1, into a suspension of 5-bromo-1H-indole-2,3-dione in acetic acid was added 4-methoxybenzohydrazide. After stirring at 100° C., the reaction mixture was cooled to rt and a yellow solid precipitated out. Filtration on a fritté, washing with AcOH, water and drying under vacuo at 60° C. overnight gave 53 mg of the title compound (57%) as a orange powder in 93% purity by HPLC (R$_t$: 4.11, gradient of 8 min, MaxPlot detection between 230 and 400 nm).

M$^-$(APCI$^-$): 374; M$^+$(APCI$^+$): 376.

Example 74

N-(4-{[2-(5-bromo-2-oxo-1,2-dihydro-3H-indol-3-ylidene)hydrazino]-carbonyl}phenyl)-3-phenylpropanamide a) Preparation of methyl 4-[(3-phenylpropanoyl)amino]benzoate (Compound C of Scheme 2)

To a solution of methyl 4-aminobenzoate (825 mg, 5.46 mmol) in anydrous pyridine (16 mL) was added dropwise hydrocinnamoyl chloride (990 μL) at 0° C. After 5 min the temperature was allowed to warm up to rt. After 90 min aminomethyl resin (Polymers Laboratories PL-AMS, 1.93 mmol/g, 1200 mg) was added and the resulting mixture was stirred overnight at rt. After rinsing the resin and filtration, water (200 mL) was added to the filtrate and a white solid precipated out. Filtration and washing with water gave a solid which was dried under vacuo at 60° C. overnight. The title compound (1.40 g) was obtained as a white solid (90%) in 98.2% purity by HPLC (MaxPlot detection between 230 and 400 nm).

$^1$H NMR (300 MHz, DMSO-d$_6$) δ 10.25 (s, 1H), 7.89 (d, J=8.9 Hz, 2H), 7.71 (d, J=8.9 Hz, 2H), 7.26 (m, 4H), 7.17 (m, 1H), 3.80 (s, 3H), 2.91 (t, J=7.6 Hz, 2H), 2.66 (t, J=7.6 Hz, 2H).

M$^-$(APCI$^-$): 282.

b) Preparation of N-[4-(hydrazinocarbonyl)phenyl]-3-phenylpropanamide (Scheme 2, compound B)

To a suspension of methyl 4-[(3-phenylpropanoyl)amino] benzoate (1.40 g, 4.94 mmol) in EtOH (16 mL) was added hydrazine hydrate (3.6 mL). After stirring for 16 h at reflux, the reaction mixture was cooled to rt and a white solid precipitated out. Filtration, washing with water (4×5 mL) and drying under vacuo at 60° C. for 2 hrs gave 1.08 g of the title compound (77%) as a white solid in 99.1% purity by HPLC (MaxPlot detection between 230 and 400 nm).

$^1$H NMR (DMSO-d$_6$, 300 MHz) δ 10.06 (s, 1H), 9.56 (s, 1H), 7.71 (d, J.=8.7Hz, 2H), 7.57 (d, J=8.7 Hz, 2H), 7.21 (m, 4H), 7.12 (m, 1H), 4.37 (s, 2H), 2.85 (t, J=7.7 Hz, 2H), 2.59 (t, J=7.7 Hz, 2H).

c) Preparation of N-(4-{[2-(5-bromo-2-oxo-1,2-dihydro-3H-indol-3-ylidene)hydrazino]-carbonyl}phenyl)-3-phenylpropanamide Into a suspension of 5-bromo-1H-indole-2,3-dione in acetic acid was added N-[4-(hydrazinocarbonyl)phenyl]-3-phenylpropanamide. After stirring at 100° C. the reaction mixture was cooled to rt and a yellow solid precipitated out. Filtration on a fritté, washing with AcOH, water and drying under vacuo at 60° C. overnight gave 621 mg of the title compound (79%) as a yellow powder in 99.3% purity by HPLC (R$_t$: 4.33, gradient of 8 mm, MaxPlot detection between 230 and 400 nm).

M.p. 326° C.

IR (neat) v 3181, 1667, 1595, 1497, 1251, 1149, 1120, 917, 756 cm$^{-1}$.

$^1$H NMR (DMSO-d$_6$, 300 MHz) δ 13.82 (s, 1H), 11.48 (s, 1H), 10.32 (s, 1H), 7.85 (d, J=9.1 Hz, 2H), 7.79 (d, J=9.1 Hz, 2H), 7.69 (d, J=2.1 Hz, 1H), 7.56 (dd, J=8.3, 2.1 Hz, 1H), 7.27 (m, 4H), 7.18 (m, 1H), 6.93 (d, J=8.3 Hz, 1H), 2.92 (t, J=7.7 Hz, 2H), 2.68 (t, J=7.7 Hz, 2H).

M$^-$(APCI$^-$): 491.

Example 75

N'-(5-Bromo-2-oxo-1,2-dihydro-3H-indol-3-ylidene)-4-{3-[2-(5-bromo-2-oxo-1,2-dihydro-3H-indol-3-ylidene)hydrazino]-3-oxopropyl}benzohydrazide A suspension of 5-bromo-1H-indole-2,3-dione (67 mg, 0.30 mmol and) and 4-(3-hydrazino-3-oxopropyl)benzohydrazide (0.03 mg, 0.13 mmol) in acetic acid (2 mL) was heated at 100° C. for 80 min. The reaction mixture was cooled to rt and a yellow solid precipitated out. Filtration, washing with AcOH (3×1 mL) and with AcOH/water (2×1 mL) and water (3×1 mL) and drying in vacuo at 70° C. for 4 hrs gave 68 mg of the title compound in a 79% yield as a yellow solid.

M$^-$(APCI$^-$): 637.

Example 76

N-(4-{[2-(5-Bromo-2-oxo-1,2-dihydro-3H-indol-3-ylidene)hydrazino]carbonyl}phenyl)-2-phenoxyacetamide a) Preparation of N-[4-hydrazinocarbonyl)phenyl]-2-phenoxyacetamide (Scheme 2, compound B)

To a suspension of methyl 4-[(phenoxyacetyl)amino]benzoate (843 mg, 2.95 mmol) in EtOH (10 mL) was added hydrazine hydrate (2.15 mL). After stirring for 15 hrs at reflux, the reaction mixture was cooled to rt. Water (10 mL) was added to the reaction mixture and a white solid precipitated out. Filtration, washing with EtOH/water (2×2 mL) and water (3×1 mL), and drying under vacuo at 70° C. for 6 hrs gave 389 mg of the title compound (46%) as a white solid in 95.4% purity by HPLC (MaxPlot detection between 230 and 400 nm).

$^1$H NMR (DMSO-d$_6$, 300 MHz) δ 10.28 (s, 1H), 9.65 (s, 1H), 7.79 (d, J=8.3 Hz, 2H), 7.69 (d, 8.3 Hz, 2H), 7.31 (m, 2H), 6.98 (m, 3H), 4.71 (s, 2H), 4.42 (s, 2H).

b) Preparation of N-(4-{[2-(5-Bromo-2-oxo-1,2-dihydro-3H-indol-3-ylidene)hydrazino]carbonyl}phenyl)-2-phenoxyacetamide Following the general method as outlined in Example 1, into a suspension of 5-bromo-1H-indole-2,3-dione in acetic acid was added N-[4-(hydrazinocarbonyl)phenyl]-2-phenoxyacetamide. After stirring at 100° C. the reaction mixture was cooled to rt and a yellow solid precipitated out. Filtration on a fritté, washing with AcOH, water and drying under vacuo at 60° C. overnight gave 2.4 mg of the title compound (2%) as a yellow powder in 86.4% purity by HPLC ($R_t$: 4.41, gradient of 8 min, MaxPlot detection between 230 and 400 nm).

M$^-$(ESI (LC/MS)$^-$): 493; M$^+$(ESI (LC/MS)$^+$): 495.

Example 77

N-(4-{[2-(5-Bromo-2-oxo-1,2-dihydro-3H-indol-3-ylidene)hydrazino]-carbonyl}benzyl)-3-nitrobenzamide a) Preparation of methyl 4-{[(3-nitrobenzoyl)amino]methyl}benzoate (Compound C of Scheme 2)

Under an inert atmosphere, to a stirred solution of methyl 4-(aminomethyl)benzoate (50 g, 0.436 mol) and TEA (210 mL, 1.5 mol) in anhydrous DCM (1.0 L) was added a solution of freshly prepared 3-nitro benzoyl chloride (0.59 mol) in DCM (250 mL). The resulting mixture was allowed to stir for 2 hrs. The reaction was quenched with a 10% aqueous solution of sodium hydrogenocarbonate. The organic layer was washed with a 1.5N HCl solution and water. After drying over MgSO$_4$ and evaporation of the solvent in vacuo, a solid was obtained and purified by flash chromatography to give the title compound (50 g) in a 52% yield as a white powder.

$^1$H NMR (300 MHz, DMSO-d$_6$) δ 9.51 (t, J=5.7 Hz, 1H), 8.73 (t, J=1.9 Hz, 1H), 8.41 (ddd, J=8.3, 2.0, 0.7 Hz, 1H), 8.34 (d, J=7.9 Hz, 1H), 7.93 (d, J=8.3 Hz, 2H), 7.79 (t, J=8.1 Hz, 1H), 7.47 (d, J=8.3 Hz, 2H), 4.59 (d, J=5.7Hz, 2H), 3.83 (s, 3H).

b) Preparation of N-[4-(hydrazinocarbonyl)benzyl]-3-nitrobenzamide (Scheme 2, compound B)

To a suspension of 4-{[(3-nitrobenzoyl)amino]methyl}benzoate (500 mg, 1.59 mmol) in EtOH (6 mL) was added hydrazine hydrate (1.16 mL). After stirring for 15 h at reflux, the reaction mixture was cooled to rt and a white solid precipitated out. Filtration, washing with EtOH (2×2 mL), EtOH/water (2×2 mL) and water (2×2 mL), and drying under vacuo at 70° C. for 5 hrs gave 379 mg of the title compound (76%) as a pale yellow solid in 96.5% purity by HPLC (MaxPlot detection between 230 and 400 nm).

$^1$H NMR (300 MHz, DMSO-d$_6$) δ 9.71 (s, 1H), 9.47 (t, J=5.7 Hz, 1H), 8.73 (s, 1H), 8.40 (d, J=8.3 Hz, 1H), 8.33 (d, J=7.5 Hz, 1H), 7.79 (m, 3H), 7.39 (d, J=8.3 Hz, 2H), 4.55 (d, J=5.7 Hz, 2H), 4.45 (s, 2H).

c) Preparation of N-(4-{[2-5-Bromo-2-oxo-1,2-dihydro-3H-indol-3-ylidene)hydrazino]-carbonyl}benzyl)-3-nitrobenzamide Into a suspension of 5-bromo-1H-indole-2,3-dione in acetic acid was added N-[4-(hydrazinocarbonyl)benzyl]-3-nitrobenzamide. After stirring at 100° C., the reaction mixture was cooled to rt and a yellow solid precipitated out Filtration on a fritté, washing with AcOH, water and drying under vacuo at 60° C. overnight gave 95 mg of the title compound (69%) as a orange powder in 88.9% purity by HPLC ($R_t$: 4.14, gradient of 8 min, MaxPlot detection between 230 and 400 nm).

M$^-$(ESI (LC/MS)$^-$): 522; M$^+$(ESI (LC/MS)$^+$): 524.

Example 78

Methyl 3-{2-[2-(5-bromo-2-oxo-1,2-dihydro-3H-indol-3-ylidene)hydrazino]-2-oxoethoxy}benzoate a) Preparation of methyl 3-(2-hydrazino-2-oxethoxy)benzoate (Compound C of Scheme 2)

To a suspension of methyl 3-(2-methoxy-2-oxoethoxy)benzoate (887 mg, 3.96 mmol) in MEOH (50 mL) was added hydrazine hydrate (1.92 mL). After stirring for 0.5 h at rt, water (50 mL) was added and the reaction mixture was filtered. Washing with water (3×5 mL) and drying under vacuo at 70° C. overnight gave 713 mg of the title compound (80%) as a white solid in 98.3% purity by HPLC (MaxPlot detection between 230 and 400 nm).

$^1$H NMR (DMSO-d$_6$, 300 MHz) δ 9.38 (s, 1H), 7.56 (d, J=7.5 Hz, 1H), 7.50 (br s, 1H), 7.44 (dd, J=8.3, 7.5 Hz, 1H), 7.24 (dd, J=8.3, 1.5 Hz, 1H), 4.55 (s, 2H), 4.32 (s, 2H), 3.84 (s, 3H).

b) Preparation of methyl 3-{2-[2-(5-bromo-2-oxo-1,2-dihydro-3H-indol-3-ylidene)hydrazino]-2-oxoethoxy}benzoate (Scheme 2, compound B)

Following the general method as outlined in Example 1, into a suspension of 5-bromo-1H-indole-2,3dione in acetic acid was added methyl 3-(2-hydrazino-2-oxoethoxy)benzoate. After stirring at 100° C., the reaction mixture was cooled to rt and a yellow solid precipitated out. Filtration on a fritté, washing with AcOH, water and drying under vacuo at 60° C. overnight gave 39 mg of the title compound (34%) as a orange powder in 97.5% purity by HPLC ($R_t$: 4.26, gradient of 8 min, MaxPlot detection between 230 and 400 nm).

M$^-$(ESI (LC/MS)$^-$): 432; M$^+$(ESI (LC/MS)$^+$): 434.

Example 79

N'-(5-Bromo-2-oxo-1,2-dihydro-3H-indol-3-ylidene)-2-[4-(1H-tetrazol-5-yl)phenoxy]acetohydrazide a) Preparation of methyl [4-(2H-tetrazol-5-yl)phenoxy]acetate (Compound C of Scheme 2)

A solution of methyl (4-F)acetate (70 g, 0.36 mol), TEA.Hcl (125 g, 0.91 mol) and NaN3 (60 g, 0.91 mol) in dry toluene (1.5 L) was stirred under reflux for 72 hrs. After cooling to rt, the reaction mixture was quenched with water (400 mL). After extraction, the aqueous layer was washed with toluene (2×250 mL). Then the organic layer was treated with a 1.5N solution of HCl until pH=2-3. A white solid precipitated out. Drying under vacuo gave the hydrochloride salt of the title compound (43 g) in a 50% yield.

$^1$H NMR (300 MHz, DMSO-d$_6$) δ 8.1 (d, J=8.6 Hz, 2H), 7.2 (d, J=8.6 Hz, 2H), 4.96 (s, 2H), 3.76 (s, 3H).

M$^-$(APCI$^-$): 233.

b) Preparation of 2-[4-(1H-tetrazol-5-yl)phenoxy]acetohydrazide (Scheme 2, compound B)

To a suspension of methyl [4-(2H-tetrazol-5-yl)phenoxy] acetate (1.10 g, 4.06 mmol) in MeOH (30 mL) was added hydrazine hydrate (2.0 mL). After stirring for 90 min at rt, the reaction mixture was evaporated off. The residue was taken up with MeOH (10 mL) and a white solid precipitated out. Filtration, washing with MeOH (2×3 mL) and drying under vacuo at 70° C. for 16 hrs gave 741 mg of the title compound (78%) as a white solid in 99.9% purity by HPLC (MaxPlot detection between 230 and 400 nm).

$^1$H NMR (DMSO-$d_6$, 300 MHz) δ 9.41 (br s, 1H), 7.96 (d, J=8.7 Hz, 2H), 7.16 (d, J=8.7 Hz, 2H), 4.58 (s, 2H).

c) Preparation of N'-(5-bromo-2-oxo-1,2-dihydro-3H-indol-3-ylidene)-2-[4-(1H-tetrazol-5-yl)phenoxy]acetohydrazide Following the general method as outlined in Example 1, into a suspension of 5-bromo-1H-indole-2,3-dione in acetic acid was added 2-[4-(1H-tetrazol-5-yl)phenoxy]acetohydrazide. After stirring at 100° C., the reaction mixture was cooled to rt and a yellow solid precipitated out. Filtration on a fritté, washing with AcOH, water and drying under vacuo at 60° C. overnight gave 40 mg of the title compound (68%) as a orange Solid in 94.9% purity by HPLC ($R_t$: 3.34, gradient of 8 mini, MaxPlot detection between 230 and 400 nm).

$^1$H NMR (DMSO-$d_6$, 300 MHz) δ 13.66 (br s, 0.6H), 12.50 (br s, 0.4H); 11.39 (s, 1H), 8.00 (d, J=8.3 Hz, 2H), 7.70 (br s, 1H), 7.56 (dd, J=8.3, 1.5 Hz, 1H), 7.26 (d, J=8.3 Hz, 2H), 6.92 (d, J=8.3 Hz, 1H), 5.42 (br s, 0.8H), 5.00 (br s, 1.2H).

M$^-$(APCI$^-$): 442.

Example 80

N'-(5-Bromo-2-oxo-1,2-dihydro-3H-indol-3-ylidene)-4-(1H-tetrazol-5-yl)benzohydrazide a) Preparation of 4-(1H-tetrazol-5-yl)benzohydrazide (Scheme 2, compound B)

To a suspension of methyl 4-(1H-tetrazol-5-yl)benzoate (1.00 g, 4.16 mmol) in EtOH (15 mL) was added hydrazine hydrate (3.0 mL). After stirring for 15 hrs at reflux, the reaction mixture was allowed to warm up to rt. A white solid precipitated out. Filtration, washing with EtOH (2×3 mL), EtOH/water (2×3 mL) and water (2×3 mL) and drying under vacuo at 70° C. for 5 hrs gave 677 mg of the title compound as a white solid in a 80% yield.

$^1$H NMR (DMSO-$d_6$, 300 MHz) δ 9.95 (br s, 1H), 8.10 (d, J=8.3 Hz, 2H), 8.01 (d, J=8.3 Hz, 2H).

b) Preparation of N'-(5-bromo-2-oxo-1,2-dihydro-3H-indol-3-ylidene)-4-(1H-tetrazol-5-yl)benzohydrazide Following the general method as outlined in Example 1, into a suspension of 5-bromo-1H-indole-2,3dione in acetic acid was added 4-(1H-tetrazol-5-yl)benzohydrazide. After stirring at 100° C., the reaction mixture was cooled to rt and a yellow solid precipitated out. Filtration on a fritté, washing with AcOH, water and drying under vacuo at 60° C. overnight gave 29 mg of the title compound (53%) as a orange Solid in 89.1% purity by HPLC ($R_t$: 3.29, gradient of 8 min, MaxPlot detection between 230 and 400 nm).

$^1$H NMR (DMSO-$d_6$, 300 MHz) δ 13.89 (s, 1H), 11.52 (s, 1H), 8.26 (d, J=8.3 Hz, 2H), 8.10 (d, J=8.3 Hz, 2H), 7.70 (s, 1H), 7.57 (d, J=8.2 Hz, 1H), 6.93 (d, J=8.2 Hz, 1H).

M$^-$(APCI$^-$): 412.

Example 81

N'-(5-Iodo-2-oxo-1,2-dihydro-3H-indol-3-ylidene)-6-methoxy-5-nitronicotinohydrazide Following the general method as outlined in Example 1, into a suspension of 5-bromo-1H-indole-2,3-dione in acetic acid was added 6-methoxy-5-nitronicotinohydrazide. After stirring at 100° C., the reaction mixture was cooled to rt and a yellow solid precipitated out. Filtration on a fritté, washing with AcOH, water and drying under vacuo at 60° C. overnight gave 81 mg of the title compound (87%) as a orange solid in 98.7% purity by HPLC ($R_t$: 4.56, gradient of 8 min, MaxPlot detection between 230 and 400 nm).

M.p. 345° C. (decomp).

IR (neat) ν 3164, 1695, 1612, 1439, 1290, 1243, 1202, 1140, 119, 814, 762, 726 cm$^{-1}$.

$^1$H NMR (DMSO-$d_6$, 300 MHz) δ 14.61 (s, 1H), 11.39 (s, 1H), 9.16 (d, J=1.9 Hz, 1H), 8.86 (d, J=1.9 Hz, 1H), 7.82 (br s, 1H), 7.70 (dd, J=8.1, 1.5 Hz, 1H), 6.81 (d, J=8.1 Hz, 1H), 3.92 (s, 3H).

M$^-$(APCI$^-$): 466; M$^+$(APCI$^+$): 468.

Analysis calculated for $C_{15}H_{10}IN_5O_5 \cdot H_2O$: C,38.73; H,2.68; N,13.28%. Found: C,38.72; H,2.80; N,13.48%.

Example 82

3-{[2-(5-Iodo-2-oxo-1,2-dihydro-3H-indol-3-ylidene)hydrazino]-sulfonyl}benzoic acid Following the general method as outlined in Example 1, into a suspension of 5-iodo-1H-indole-2,3-dione in acetic acid was added 3-(hydrazinosulfonyl)benzoic acid. After stirring at 100° C., the reaction mixture was cooled to rt and a yellow solid precipitated out. Filtration on a fritté, washing with AcOH, water and drying under vacuo at 60° C. overnight gave 131 mg of the title compound (71%) as a yellow solid in 87.8% purity by HPLC ($R_t$: 4.71, gradient of 10 min, MaxPlot detection between 230 and 400 nm).

M.p. 233° C. (decomp).

$^1$H NMR (DMSO-$d_6$, 300 MHz) δ 11.23 (s, 1H), 8.47 (s, 1H), 8.23 (m, 2H), 7.77 (t, J=7.9 Hz, 1H), 7.65 (m, 2H), 6.72 (d, J=8.7 Hz, 1H).

Example 83

2-Hydroxy-5-{[2-(5-iodo-2-oxo-1,2-dihydro-3H-indol-3-ylidene)hydrazino]sulfonyl}benzoic acid Following the general method as outlined in Example 1, into a suspension of 5-iodo-1H-indole-2,3-dione in acetic acid was added 5-(hydrazinosulfonyl)-2-hydroxybenzoic acid. After stirring at 100° C., the reaction mixture was cooled to rt and a yellow solid precipitated out. Filtration on a fritté, washing with AcOH, water and drying under vacuo at 60° C. overnight gave 108 mg of the title compound (59%) as a yellow solid in 92.8% purity by HPLC ($R_t$: 4.85, gradient of 10 min, MaxPlot detection between 230 and 400 mn).

M.p. 240° C. (decomp).

$^1$H NMR (DMSO-$d_6$, 300 MHz) δ 12.45 (br s, 1H), 11.25 (s, 1H), 8.33 (d, J=2.4 Hz, 1H), 8.04 (dd, J=8.9,2.4 Hz, 1H), 7.65 (m, 2H), 7.17 (d, J=8.9 Hz, 1H), 6.73 (d, J=8.3 Hz, 1H).

Example 84

N'-(5-Iodo-2-oxo-1,2-dihydro-3H-indol-3-ylidene)-5-(2-pyridinyl)-2-thiophenesulfonohydrazide Following the general method as outlined in Example 1, into a suspension of 5-iodo-1H-indole-2,3-dione in acetic acid was added 5-(2-pyridinyl)-2-thiophenesulfonohydrazide. After stirring at 100° C., the reaction mixture was cooled to rt and a yellow solid precipitated out. Filtration on a fritté, washing with AcOH, water and drying under vacuo at 60° C. overnight gave 23 mg of the title compound (23%) as a yellow solid in 94.8% purity by HPLC ($R_t$: 3.68, 5.13, gradient of 8 min, MaxPlot detection between 230 and 400 nm).

M.p. 162° C. (decomp).

$M^+(APCI^+)$: 511.

Example 85

4-Chloro-N'-(5-iodo-2-oxo-1,2-dihydro-3H-indol-3-ylidene)-3-nitrobenzenesulfonohydrazide Following the general method as outlined in Example 1, into a suspension of 5-iodo-1H-indole-2,3-dione in acetic acid was added 4-chloro-3-nitrobenzenesulfonohydrazide. After stirring at 100° C., the reaction mixture was cooled to rt and a yellow solid precipitated out. Filtration on a fritté, washing with AcOH, water and drying under vacuo at 60° C. overnight gave 78 mg of the title compound (77%) as a yellow solid in 73% purity by HPLC ($R_t$: 3.65, 5.39, gradient of 8 min, MaxPlot detection between 230 and 400 nm).

M.p. 219° C. (decomp).

Example 86

N-Dodecyl-3-[(4-hydroxybenzoyl)hydrazono]-2-oxo-2,3-dihydro-1H-indole-7-carboxamide a) Preparation of N-dodecyl-2,3-dioxo-7-indolinecarboxamide

Into a solution of 2,3-dioxo-7-indolinecarboxylic acid (1000 mg, 5.23 mmol), 1-dodecanamine (1066 mg, 5.75 mmol), TEA (1.60 mL, 11.51 mmol), EDCI.HCl (1102 mg, 5.75 mmol) and HOBt (777 mg, 5.75 mmol) in DMF (60 mL). The resulting mixture was allowed to stir at rt for 24 hrs. The solvent was evaporated off and the residue was taken up in DCM to be purified by flash chromatography using DCM/MeOH (98/2) as eluant. A gummy orange solid was collected to be identified as the title compound (44%) in a 96.0% purity by HPLC (MaxPlot detection between 230 and 400 nm).

$M^-(APCI^-)$: 357; $M^+(APCI^+)$: 359.

b) Preparation of N-dodecyl-3-[(4-hydroxybenzovyl)hydrazono]-2-oxo-2,3-dihydro-1H-indole-7-carboxamide Following the general method as outlined in Example 1, into a suspension of N-dodecyl-2,3-dioxo-7-indolinecarboxamide in acetic acid was added 4-hydroxybenzohydrazide. After stirring at 100° C., the reaction mixture was cooled to rt and a yellow solid precipitated out. Filtration on a fritté, washing with AcOH, water and drying under vacuo at 60° C. overnight gave 46 mg of the title compound (33%) as a yellow powder in 99.8% purity by HPLC ($R_t$: 5.95, gradient of 8 min, MaxPlot detection between 230 and 400 nm).

$M^-(ESI^-)$: 491.

Example 87

Methyl {3-[(4-hydroxybenzoyl)hydrazono]-5-iodo-2-oxo-2,3-dihydro-1H-indol-1-yl}acetate Into a solution of 4-hydroxy-N-(5-iodo-2-oxo-1,2-dihydro-3H-indol-3-ylidene)benzohydrazide (200 mg, 0.49 mmol) in anhydrous DMF (4 mL) were added DBU (0.11 mL, 0.73 mmol) and methyl bromoacetate (0.95 mL, 0.98 mmol). The resulting mixture was stirred at rt for 1 hr and quenched with water. Upon addition of 1N HCl a yellow solid precipitated out. Filtration and washing with water gave a yellow solid which was recrystallized from AcOH to give the title compound as a yellow powder (79 mg, 34%) in 97.0% purity by HPLC (MaxPlot detection between 230 and 400 nm).

Example 88

N-Dodecyl-3-[(4-hydroxybenzoyl)hydrazono]-5-iodo-2-oxo-2,3-dihydro-1H-indole-1-carboxamide a) Preparation of N-dodecyl-2,3-dioxo-7-indolinecarboxamide

Into a solution of 2,3-dioxo-7-indolinecarboxylic acid (1000 mg, 5.23 mmol), 1-dodecanamine (1066 mg, 5.75 mmol), TEA (1.60 mL, 11.51 mmol), EDCI.HCl (1102 mg, 5.75 mmol) and HOBt (777 mg, 5.75 mmol) in DMF (60 mL). The resulting mixture was allowed to stir at rt for 24 hrs. The solvent was evaporated off and the residue was taken up in DCM to be purified by flash chromatography using DCM/MeOH (98/2) as eluant. A gummy orange solid was collected to be identified as the title compound (44%) in a 96.0% purity by HPLC (MaxPlot detection between 230 and 400 nm).

$M^-(APCI^-)$: 357; $M^+(APCI^+)$: 359.

b) Preparation of N-Dodecyl-3-[(4-hydroxybenzoyl)hydrazono]-5-iodo-2-oxo-2,3-dihydro-1H-indole-1-carboxamide Following the general method as outlined in Example 1, into a suspension of N-dodecyl-2,3-dioxo-7-indolinecarboxamide in acetic acid was added 4-hydroxybenzohydrazide. After stirring at 100° C., the reaction mixture was cooled to rt and a yellow solid precipitated out. Filtration on a fritté, washing with AcOH, water and drying under vacuo at 60° C. overnight gave 26 mg of the title compound (68%) as a yellow powder in 96.3% purity by HPLC ($R_t$: 7.25, gradient of 8 min, MaxPlot detection between 230 and 400 nm).

$M^-(APCI^-)$: 617; $M^+(APCI^+)$: 619.

Example 89

Methyl (3-{[4-(hexanoylamino)benzoyl]hydrazono}-5-iodo-2-oxo-2,3-dihydro-1H-indol-1-yl)acetate a) Preparation of methyl 4-(hexanoylamino)benzoate (Compound C of Scheme 2)

To a solution of methyl 4-aminobenzoate (500 mg, 3.31 mmol) in anhydrous pyridine (10 mL) was added dropwise hexanoyl chloride (550 µL) at 0° C. After 5 min the temperature was allowed to warm up to rt. After 90 min aminomethyl resin (Polymers Laboratories PL-AMS, 1.93 mmol/g, 720 mg) was added and the resulting mixture was stirred overnight at rt. After filtration and rinsing the resin, water (125 mL) was added to the filtrate and a white solid precipated out. Filtration and washing with water gave a solid which was dried under vacuo at 60° C. overnight. The title compound (699 mg) was obtained as a white solid (85%) in 96.9% purity by HPLC (MaxPlot detection between 230 and 400 nm).

$^1$H NMR (300 MHz, DMSO-$d_6$) δ 10.20 (s, 1H), 7.89 (d, J=8.7 Hz, 2H), 7.72 (d, J=8.7 Hz, 2H), 3.80 (s, 3H), 2.32 (t, J=7.4 Hz, 2H), 1.58 (m, 2H), 1.28 (m, 4H), 0.86 (t, J=6.8 Hz, 3H).

M$^-$(APCI$^-$): 248.

b) Preparation of
N-[4(hydrazinocarbonyl)phenyl]hexanamide
(Scheme 2, Compound B)

To a suspension of methyl 4-(hexanoylamino)benzoate (583 mg, 2.34 mmol) in ETOH (8 mL) was added hydrazine hydrate (1.8 mL). After stirring for 15 h at reflux, the reaction mixture was cooled to rt and a white solid precipitated out. Filtration, washing with water (2×2 mL), and drying under vacuo at rt for 72 hrs gave 321 mg of the title compound (55%) as a white solid in 96.6% purity by HPLC (MaxPlot detection between 230 and 400 nm).

$^1$H NMR (DMSO-$d_6$, 300 MHz) δ 10.06 (s, 1H), 9.60 (s, 1H), 7.75 (d, J=8.5 Hz, 2H), 7.62 (d, J=8.5 Hz, 2H), 4.42 (s, 2H), 2.30 (t, J=7.2 Hz, 2H), 1.58 (m, 2H), 1.28 (m, 4H), 0.86 (m, 3H).

c) Preparation of Methyl (3-{[4-(hexanoylamino)
benzoyl]hydrazono}-5-iodo-2-oxo-2,3-dihydro-1H-
indol-1-yl)acetate Following the general method as outlined in Example 1, into a suspension of methyl (5-iodo-2,3-dioxo-2,3-dihydro-1H-indol-1-yl)acetate in acetic acid was added N-[4-(hydrazinocarbonyl)phenyl]hexamide. After stirring at 100° C., the reaction mixture was cooled to rt and a yellow solid precipitated out. Filtration on a fritté, washing with AcOH, water and drying under vacuo at 60° C. overnight gave 183 mg of the title compound (91%) as a yellow powder in 99.4% purity by HPLC (R$_t$: 4.97, gradient of 8 min, MaxPlot detection between 230 and 400 nm).

$^1$H NMR (DMSO-$d_6$, 300 MHz) δ 13.56 (s, 1H), 10.28 (s, 1H), 7.91 (d, J=1.5 Hz, 1H), 7.83 (m, 5H), 7.11 (d, J=8.6 Hz, 1H), 4.74 (s, 2H), 3.70 (s, 3H), 2.34 (t, J=7.4 Hz, 2H), 1.60 (m, 2H), 1.29 (m, 4H), 0.87 (t, J=6.8 Hz, 3H).

M$^-$(APCI$^-$): 575; M$^+$(APCI$^+$): 577.

Example 90

(3-{[4-(Hexanoylamino)benzoyl]hydrazono}-5-iodo-
2-oxo-2,3dihydro-1H-indol-1-yl)acetic acid Into a suspension of methyl (3-{([4-(hexanoylamino)benzoyl]hydrazono}-5-iodo-2-oxo-2,3-dihydro-1H-indol-1-yl)acetate (650 mg, 1.13 mmol) in THF/H$_2$O (2/1) (25 mL) was added NaOH (1.0 N, 5.6 mL). The resulting solution was stirred at rt for 0.5 hr and quenched with HCl (5 N, 5 mL) and water (25 mL). A yellow solid precipitated out. Filtration, washing with water (4×10 mL) and drying under vacuo at 60° C. for 15 hrs gave a yellow solid. Recrystallization from AcOH (60 mL) gave the title compound as a yellow powder (411 mg, 64%) in 99.9% purity by HPLC (MaxPlot detection between 230 and 400 nm).

M.p. 298° C. (decomp).

$^1$H NMR (300 MHz, DMSO-$d_6$) δ 13.60 (s, 1H), 13.36 (s, 1H), 10.29 (s, 1H), 7.85 (m, 6H), 7.10 (d, J=8.3 Hz, 1H), 4.61 (s, 2H), 2.34 (t, J=7.4 Hz, 2H), 1.59 (m, 2H), 1.29 (m, 4H), 0.87 (m, 3H).

M$^+$(APCI$^+$): 563.

Example 91

(3-{[4-(Hexanoylamino)benzoyl]hydrazono}-5-iodo-
2-oxo-2,3-dihydro-1H-indol-1-yl)acetic acid,
tromethanine (2-amino-2-hydroxymethyl-1,3-pro-
panediol) salt A solution of (3-{[4-(hexanoylamino)benzoyl]hydrazono}-5-iodo-2-oxo-2,3-dihydro-1H-indol-1-yl)acetic acid (22 mg, 0.039 mmol) and tris(hydroxymethyl)amino methane (4.8 mg, 1 equiv.) in MeOH/H$_2$O (4/1) (25 mL) was stirred for 15 min. The solvent was partially evaporated off under vacuo. Then the solution was lyophilized to give the title compound as a yellow solid (19 mg, 71%) in 98.7% purity by HPLC (detection at 254 nm).

M.p. 207-210° C. (decomp).

Example 92

(3-{[4-(Hexanoylamino)benzoyl]hydrazono}-5-iodo-
2-oxo-2,3-dihydro-1H-indol-1-yl)acetic acid, N-me-
thyl-D-glucamine (1-deoxy-1-(methylamino)gluci-
tol) salt Into a solution of N-methyl-D-glucamine (135 mg, 0.69 mmol) in MeOH (50 mL) at reflux was added a solution of (3-{[4-(hexanoylamino)benzoyl]hydrazono}-5-iodo-2-oxo-2,3-dihydro-1H-indol-1-yl)acetic acid (353 mg, 0.63 mmol) in warm DMSO (5 mL). After 10 min of stirring, the heating bath was removed and Et$_2$O (250 mL) was added. A yellow solid precipitated out. Filtration, washing with Et$_2$O (10×10 mL) and drying under vacuo at 60° C. for 24 hrs gave a title compound as a yellow solid (421 mg, 88%) in 99.7% purity by HPLC (MaxPlot detection between 230 and 400 nin).

M.p. 165-167° C. (decomp).

Example 93

2-(4-Cyanophenoxy)-N'-(5-iodo-2-oxo-1,2-dihydro-
3H-indol-3-ylidene)acetohydrazide a) Preparation of 2-(4cyanophenoxy)acetohydrazide
(Scheme 2, compound B)

To a solution of methyl (4-cyanophenoxy)acetate (3.52 g, 18.4 mmol) in MEOH (100 mL) was added hydrazine hydrate (8.9 mL). After stirring for 1 h at rt, a solid precipitated out. Filtration, washing with MeOH (5 mL) and water (4×10 mL) and drying under vacuo at 50° C. overnight gave the title compound (2.63 g, 75%) as a white solid in 98.4% purity by HPLC (MaxPlot detection between 230 and 400 nm).

$^1$H NMR (300 MHz, DMSO-$d_6$) δ 9.40 (s, 1H), 7.77 (d, J=8.7 Hz, 2H), 7.10 (d, J=8.7 Hz, 2H), 4.59 (s, 2H), 4.33 (s, 2H).

b) Preparation of 2-(4-cyanophenoxy)-N-(5-iodo-2-
oxo-1,2-dihydro-3H-indol-3-ylidene)acetohydrazide Following the general method as outlined in Example 1, into a suspension of 5-iodo-1H-indole-2,3dione in acetic acid was added 2-(4-cyanophenoxy)acetohydrazide. After stirring at 100° C., the reaction mixture was cooled to rt and a yellow solid precipitated out. Filtration on a fritté, washing with AcOH and water, drying under vacuo at 50° C. overnight and recrystallization from DMSO gave the title compound (642 mg, 60%) as an orange solid in 99.3% purity by HPLC (Max-Plot detection between 230 and 400 nm).

M.p. 330° C. (decomp).

IR (neat) ν 3174, 3067, 2224, 1693, 1501, 1206, 1171, 1136, 825 cm$^{-1}$.

$^1$H NMR (300 MHz, DMSO-d$_6$) δ 13.57 (br s, 0.5H), 12.45 (br s, 0.5H), 11.36 (s, 1H), 7.82 (m, 3H), 7.71 (dd, J=8.1, 1.7 Hz, 1H), 7.20 (d, J=8.3 Hz, 2H), 6.79 (d, J=8.1 Hz, 1H), 5.44 (br s, 1H), 5.02 (br s, 1H).

M$^-$(APCI$^-$): 445.

Analysis calculated for C$_{17}$H$_{11}$IN$_4$O$_3$.0.7 H$_2$O: C,44.50; H,2.72; N,12.21%. Found: C,44.47; H,2.53; N,12.15%.

Example 94

4-({2-[2-(5-Iodo-2-oxo-1,2-dihydro-3H-indol-3-ylidene)hydrazino]-2-oxoethyl}thio)-3-nitrobenzenesulfonamide Following the general method as outlined in Example 1, into a suspension of 5-iodo-1H-indole-2,3-dione in acetic acid was added 4-[(2-hydrazino-2-oxoethyl)thio]-3-nitrobenzenesulfonamide. After stirring at 100° C., the reaction mixture was cooled to rt and a yellow solid precipitated out. Filtration on a fritté, washing with AcOH, water and drying under vacuo at 60° C. overnight gave 24 mg of the title compound (61%) as a yellow solid in 99.3% purity by HPLC (R$_t$: 3.51, 4.17, gradient of 8 min, MaxPlot detection between 230 and 400 nm).

M.p. 282° C. (decomp).

M$^-$(ESI (LC/MS)$^-$): 560; M$^+$(ESI (LC/MS)$^+$): 562.

Example 95

N-(4-{[2-(5-Iodo-2-oxo-1,2-dihydro-3H-indol-3-ylidene)hydrazino]carbonyl}phenyl)-N-methyl-3-phenylpropanamide a) Preparation of methyl 4-[methyl(3-phenylpropanoyl)amino]benzoate (Compound C of Scheme 2)

To a solution of methyl 4-methylaminobenzoate (1.0 g, 6.05 mmol) in anhydrous pyridine (20 mL) was added dropwise hydrocinnamoyl chloride (1080 μL) at rt. After 16 hrs water (5 mL) was added and the resulting mixture was stirred for 1 hr at rt. The resulting mixture was poured into water (300 mL) and HCl (5 N, 50 mL) was added. The compound was extracted with AcOEt (2×300 mL) and washed with a saturated aqueous solution of NaHCO$_3$ (150 mL). The combined organic layers were dried over MgSO$_4$ and evaporated under vacuo to give the title compound (1.80 g) was obtained as a beige solid (95%) in 95.3% purity by HPLC (MaxPlot detection between 230 and 400 nm).

$^1$H NMR (300 MHz, DMSO-d$_6$) δ 7.96 (d, J=8.4 Hz, 2H), 7.38 (d, J=8.4 Hz, 2H), 7.24-7.07 (m, 5H), 3.84 (s, 3H), 3.19 (s, 3H), 2.78 (t, J=7.6 Hz, 2M), 2.42 (m, 2H).

b) Preparation of N-[4-(hydrazinocarbonyl)phenyl]-N-methyl-3-phenylpropanamide (Scheme 2, compound B)

To a solution of methyl 4-[methyl(3-phenylpropanoyl)amino]benzoate (1600 mg, 5.38 mmol) in EtOH (14 mL) was added hydrazine hydrate (4.0 mL). The resulting mixture was stirred for 16 h at reflux and evaporated under vacuo to give the title compound (1600 mg, 100%) as a gummy colorless oil, which was used in the next step without any further purification.

$^1$H NMR (300 MHz, DMSO-d$_6$) δ 9.78 (s, 1H), 7.82 (d, J=8.5 Hz, 2H), 7.30 (d, J=8.5 Hz, 2H), 7.24-7.06 (m, 5H), 4.51 (br s, 2H), 3.16 (s, 3H), 2.77 (t, J=7.7 Hz, 2H), 2.36 (m, 2H).

c) Preparation of N-(4-{[2-(5-iodo-2-oxo-1,2-dihydro-3H-indol-3-ylidene)hydrazino]carbonyl}phenyl)-N-methyl-3-phenylpropanamide Following the general method as outlined in Example 1, into a suspension of 5-iodo-1H-indole-2,3dione in acetic acid was added N-[4(hydrazinocarbonyl)phenyl]-N-methyl-3-phenylpropanamide. After stirring at 100° C., the reaction mixture was cooled to rt and a yellow solid precipitated out. Filtration on a fritté, washing with AcOH and water and drying under vacuo at 60° C. overnight gave the title compound (226 mg, 56%) as an orange solid in 96.7% purity by HPLC (MaxPlot detection between 230 and 400 nm).

M.p. 239° C.

$^1$H NMR (300 MHz, DMSO-d$_6$) δ 13.81 (s, 1H), 11.48 (s, 1H), 7.80 (m, 3H), 7.82 (s, 1H), 7.45 (m, 2H), 7.15 (m, 5H), 6.80 (m, 1H), 3.29 (s, 3H), 2.81 (m, 2H), 2.49 (m, 2H).

M$^-$(APCI$^-$): 551. M$^+$(APCI$^+$): 553.

Example 96

Methyl {3-[(4-{[3-(1,3-benzodioxol-5-yl)propanoyl]amino}benzoyl)hydrazono]-5-iodo-2-oxo-2,3-dihydro-1H-indol-1-yl}acetate a) Preparation of methyl (5-iodo-2,3-dioxo-2,3-dihydro-1H-indol-1-yl)acetate (Precursor of Compound A)

Into a solution of 5-iodo-1H-indole-2,3dione (10.0 g, 36.6 mmol) in anhydrous DMF (180 ml) were added DBU (8.2 mL, 54.9 mmol) and methyl bromoacetate (5.1 mL, 54.9 mmol). After stirring at rt for 45 min, the reaction mixture was quenched with water (600 mL) and HCl (1N, 100 mL). Extraction with EtOAc (3×500 mL), drying over MgSO$_4$ and evaporation under vacuo gave a residue. Recrystallization from AcOEt 150 mL) gave the title compound as an orange powder (6.45 g, 51%) in 99.1% purity by HPLC (MaxPlot detection between 230 and 400 nm).

$^1$H NMR (300 MHz, DMSO-d$_6$) δ 8.01 (dd, J=8.2, 1.8 Hz, 1H), 7.87 (d, J=1.8 Hz, 1H), 7.07 (d, J=8.2 Hz, 1H), 4.61 (s, 2H), 3.69 (s, 3H).

b) Preparation of methyl 4-{[3-(1,3-benzodioxol-5-yl)propanoyl]amino}benzoate (Compound C of Scheme 2)

To a solution of 3-(3,4-methylenedioxyphenyl)-propionic acid (501 mg, 2.58 mmol) in anhydrous THF (10 mL) were added N-methylmorpholine (0.28 mL, 2.58 mmol) and isobutylchloroformate (0.33 mL, 2.58 mmol) at 0° C. After 30 min, at 0° C., a solution of methyl 4-aminobenzoate (390 mg, 2.58 mmol) in anhydrous THF (2 mL) was added to the reaction mixture. After 30 min the temperature was allowed to warm up to rt and stir for 24 hrs. After extraction with EtOAc (100 mL), washing with HCl (0.1 N, 50 mL) and a saturated aqueous solution of NaHCO$_3$ (50 mL), the organic layer was dried over sodium sulfate and evaporated under vacuo to give a solid. The residue was taken up in Et$_2$O, filtrated and washed with Et$_2$O gave the title compound as a white solid (62%) in 99.4% purity by HPLC (MaxPlot detection between 230 and 400 nm).

¹H NMR (300 MHz, DMSO-d$_6$) δ 10.22 (s, 1H), 7.89 (d, J=8.7 Hz, 2H), 7.70 (d, J=8.7 Hz, 2H), 6.82 (d, J=1.6 Hz, 1H), 6.80 (d, J=7.9 Hz, 1H), 6.68 (dd, J=7.9, 1.6 Hz, 1H), 5.94 (s, 2H), 3.80 (s, 3H), 2.82 (t, J=7.5 Hz, 2H), 2.61 (t, J=7.5 Hz, 2H).

c) Preparation of 3-(1,3-benzodioxol-5-yl)-N-[4-(hydrazinocarbonyl)phenyl]propanamide (Scheme 2, compound B)

To a suspension of methyl 4-{[3-(1,3-benzodioxol-5-yl)propanoyl]amino}benzoate (200 mg, 0.61 mmol) in EtOH (3.5 mL) was added hydrazine hydrate (0.5 mL). After stirring for 15 hrs at reflux, the reaction mixture was cooled to rt and a white solid precipitated out. Filtration, washing with EtOH (2×1 mL) and water (3×1 mL), and drying under vacuo at 70° C. for 1 hr gave 130 mg of the title compound (65%) as a white solid in 95.5% purity by HPLC (MaxPlot detection between 230 and 400 nm).

¹H NMR (300 MHz, DMSO-d$_6$) δ 10.08 (s, 1H), 9.60 (s, 1H), 7.75 (d, J=8.5 Hz, 2H), 7.61 (d, J=8.5 Hz, 2H), 6.82 (d, J=1.5 Hz, 1H), 6.80 (d, J=7.9 Hz, 1H), 6.68 (dd, J=7.9, 1.5 Hz, 1H), 5.94 (s, 2H), 4.41 (s, 2H), 2.82 (t, J=7.6 Hz, 2H), 2.59 (t, J=7.6 Hz, 2H).

d) Preparation of methyl {3-[(4-{[3-1,3-benzo-dioxol-5-yl)propanoyl]amino}benzoyl)hydrazono]-5-iodo-2-oxo-2,3-dihydro-1H-indol-1-yl}acetate Following the general method as outlined in Example 1, into a suspension of methyl (5-iodo-2,3-dioxo-2,3-dihydro-1H-indol-1-yl)acetate in acetic acid was added 3-(1,3-benzodioxol-5-yl)-N-[4-(hydrazinocarbonyl)phenyl]propanamide. After stirring at 100° C., the reaction mixture was cooled to rt and a yellow solid precipitated out. Filtration on a fritté, washing with AcOH, water and drying under vacuo at 60° C. overnight gave 519 mg of the title compound (95%) as a yellow powder in 98.6% purity by HPLC (R$_t$: 4.44, 4.94 gradient of 8 min, MaxPlot detection between 230 and 400 nm).

M.p. 236° C.

¹H NMR (DMSO-d$_6$, 300 MHz) δ 13.56 (s, 1H), 10.30 (s, 1H), 7.91-7.78 (m, 6H), 7.11 (d, J=8.3 Hz, 1H), 6.81 (m, 2H), 6.70 (d, J=7.9 Hz, 1H), 5.95 (s, 2H), 4.74 (s, 2H), 3.70 (s, 3H), 2.84 (t, J=7.4 Hz, 2H), 2.63 (t, J=7.4 Hz, 2H).

M⁻(ESI (LC/MS)⁻): 653; M⁺(ESI (LC/MS)⁺): 655.

Example 97

Methyl 4-[(4-{[2-(5-iodo-2-oxo-1,2-dihydro-3H-indol-3-ylidene)hydrazino]-carbonyl}phenyl)amino]-4-oxobutanoate a) Preparation of tert-butyl 2-{4-[(4-methoxy-4-oxobutanoyl)amino]benzoyl}hydrazinecarboxylate (Compound B of Scheme 2)

To a solution of tert-butyl 2-(4-aminobenzoyl)hydrazinecarboxylate (500 mg, 1.99 mmol) in anhydrous pyridine (10 mL) was added dropwise 3-carbomethoxypropionyl chloride (Fluka) (300 μL) at rt. After 60 min, aminomethyl resin (Polymers Laboratories PL-AMS, 1.96 mmol/g, 400 mg) was added and the resulting mixture was stirred overnight at rt. After filtration and rinsing the resin, water (80 mL) was added into the filtrate and a white solid precipitated out. Filtration and washing with water gave a white solid, which was dried under vacuo at 70° C. for 2 hrs. The title compound (461 mg) was obtained as a white solid (63%) in 96.0% purity by HPLC (MaxPlot detection between 230 and 400 nm).

M.p. 111-113° C.

¹H NMR (300 MHz, DMSO-d$_6$) δ 10.25 (s, 1H), 10.05 (s, 1H), 8.84 (s, 1H), 7.80 (d, J=8.4 Hz, 2H), 7.65 (d, J=8.4 Hz, 2H), 3.59 (s, 3H), 2.62 (m, 4H), 1.42 (s, 9H).

M⁻(ESI (LC/MS)⁻): 364; M⁺(ESI (LC/MS)⁺): 366.

b) Preparation of methyl 4-[(4-{[2-(5-iodo-2-oxo-1,2-dihydro-3H-indol-3-ylidene)hydrazino]carbonyl}phenyl)amino]-4-oxobutanoate (Scheme 1)

Following the general method as outlined in Example 1, into a suspension of 5-iodo-1H-indole-2,3-dione in acetic acid in the presence of 5% TFA was added tert-butyl 2-{4-[(4-methoxy-4-oxobutanoyl)amino]benzoyl}hydrazinecarboxylate. After stirring at 100° C., the reaction mixture was cooled to rt and an orange solid precipitated out. Filtration on a fritté, washing with AcOH, water and drying under vacuo at 60° C. for 60 min gave 89 mg of the title compound (92%) as an orange solid in 98.8% purity by HPLC (MaxPlot detection between 230 and 400 nm).

M.p. 291° C. (decomp.).

¹H NMR (300 MHz, DMSO-d$_6$) δ 13.81 (s, 1H), 11.45 (s, 1H), 10.41 (s, 1H), 7.85 (m, 3H), 7.79 (d, J=8.7 Hz, 2H), 7.71 (dd, J=8.3, 1.8 Hz, 1H), 6.81 (d, J=8.3 Hz, 1H), 3.59 (s, 3H), 2.64 (m, 4H).

M⁻(APCI⁻): 519. M⁺(APCI⁺): 521.

Example 98

3-(1,3-Benzodioxol-5-yl)-N-(4-{[2-(5-bromo-2-oxo-1,2-dihydro-3H-indol-3-ylidene)hydrazino]carbonyl}phenyl)propanamide a) Preparation of methyl 4-{[3-(1,3-benzodioxol-5-yl)propanoyl]amino}benzoate (Compound C of Scheme 2)

To a solution of 3-(3,4-methylenedioxyphenyl)-propionic acid (501 mg, 2.58 mmol) in anhydrous THF (10 mL) were added N-methylmorpholine (0.28 mL, 2.58 mmol) and isobutylchloroformate (0.33 mL, 2.58 mmol) at 0° C. After 30 min, at 0° C., a solution of methyl 4-aminobenzoate (390 mg, 2.58 mmol) in anhydrous THF (2 mL) was added to the reaction mixture. After 30 min the temperature was allowed to warm up to rt and stir for 24 hrs. After extraction with EtOAc (100 mL), washing with HCl (0.1N, 50 mL) and a saturated aqueous solution of NaHCO$_3$ (50 mL), the organic layer was dryed over sodium sulfate and evaporated under vacuo to give a solid. The residue was taken up in Et$_2$O, filtrated and washed with Et$_2$O gave the title compound as a white solid (62%) in 99.4% purity by HPLC (MaxPlot detection between 230 and 400 nm).

¹H NMR (DMSO-d$_6$, 300 MHz) δ 10.22 (s, 1H), 7.89 (d, J=8.7 Hz, 2H), 7.70 (d, J=8.7 Hz, 2H), 6.82 (d, J=1.6 Hz, 1H), 6.80 (d, J=7.9 Hz, 1H), 6.68 (dd, J=7.9, 1.6 Hz, 1H), 5.94 (s, 2H), 3.80 (s, 3H), 2.82 (t, J=7.5 Hz, 2H), 2.61 (t, J=7.5 Hz, 2H).

b) Preparation of 3-(1,3-benzodioxol-5-yl)-N-[4-hydrazinocarbonyl)phenyl]propanamide (Scheme 2, compound B)

To a suspension of methyl 4-{[3-(1,3-benzodioxol-5-yl)propanoyl]amino}benzoate (200 mg, 0.61 mmol) in ETOH (3.5 mL) was added hydrazine hydrate (0.5 mL). After stirring for 15 hrs at reflux, the reaction mixture was cooled to rt and a white solid precipitated out. Filtration, washing with EtOH (2×1 mL) and water (3×1 mL), and drying under vacuo at 70° C. for 1 hr gave 130 mg of the title compound (65%) as a white solid in 95.5% purity by HPLC (MaxPlot detection between 230 and 400 nm).

$^1$H NMR (300 MHz, DMSO-$d_6$) δ 10.08 (s, 1H), 9.60 (s, 1H), 7.75 (d, J=8.5 Hz, 2H), 7.61 (d, J=8.5 Hz, 2H), 6.82 (d, J=1.5 Hz, 1H), 6.80 (d, J=7.9 Hz, 1H), 6.68 (dd, J=7.9, 1.5 Hz, 1H), 5.94 (s, 2H), 4.41 (s, 2H), 2.82 (t, J=7.6 Hz, 2H), 2.59 (t, J=7.6 Hz, 2H).

c) Preparation of 3-(1,3-Benzodioxol-5-yl)-N-(4-{[2-(5-bromo-2-oxo-1,2-dihydro-3H-indol-3-ylidene) hydrazino]carbonyl}phenyl)propanamide Following the general method as outlined in Example 1, into a suspension of 5-bromo-1H-indole-2,3dione in acetic acid was added 3-(1,3-benzodioxol-5-yl)-N-[4-(hydrazinocarbonyl)phenyl]propanamide. After stirring at 100° C., the reaction mixture was cooled to rt and a yellow solid precipitated out. Filtration on a fritté, washing with AcOH, water and drying under vacuo at 60° C. overnight gave 151 mg of the title compound (89%) as a yellow solid in 98.2% purity by HPLC (MaxPlot detection between 230 and 400 nm).

M.p. 325° C. (decomp.).

$^1$H NMR (300 MHz, DMSO-$d_6$) δ 13.83 (s, 1H), 11.48 (s, 1H), 10.30 (s, 1H), 7.86 (d, J=8.7 Hz, 2H), 7.79 (d, J=8.7 Hz, 2H), 7.70 (d, J=1.7 Hz, 1H), 7.56 (dd, J=8.3, 1.7 Hz, 1H), 6.93 (d, J=8.3 Hz, 1H), 6.81 (m, 2H), 6.70 (d, J=7.5 Hz, 1H), 5.95 (s, 2H), 2.84 (t, J=7.3 Hz, 2H), 2.63 (t, J=7.3 Hz, 2H).

M$^-$(ESI (LC/MS)): 535; M$^+$(ESI (LC/MS)$^+$): 537.

Example 99

{3-[(4-{[3-(1,3-benzodioxol-5-yl)propanoyl] amino}benzoyl)hydrazono]-5-iodo-2-oxo-2,3-dihydro-1H-indol-1-yl}acetic acid Into a suspension of methyl {3-[(4-{[3-(1,3-benzodioxol-5-yl)propanoyl]amino}benzoyl)hydrazono]-5-iodo-2-oxo-2,3-dihydro-1H-indol-1-yl) acetate (419 mg, 0.64 mmol) in THF/H$_2$O (10/1) (200 mL) was added NaOH (1 N, 2 mL). The resulting solution was stirred at rt for 1 hr and quenched with HCl (5 N, 5 mL) and water (300 mL). A yellow solid precipitated out. Filtration, washing with water (3×10 mL) and drying under vacuo at 70° C. for 15 hrs gave the title compound as a yellow solid (264 mg, 64%) in 99.6% purity by HPLC (MaxPlot detection between 230 and 400 nm).

M.p. 297° C. (decomp).

$^1$H NMR (300 MHz, DMSO-$d_6$) δ 13.60 (s, 1H), 13.35 (s, 1H), 10.31 (s, 1H), 7.85 (m, 6H), 7.11 (m, 1H), 6.83 (m, 2H), 6.71 (m, 1H), 5.94 (s, 2H), 4.61 (s, 2H), 2.83 (m, 2H), 2.64 (m, 2H).

M$^-$(ESI (LC/MS)$^-$): 639; M$^+$(ESI (LC/MS)$^+$): 641.

Example 100

{3-[(4-{[3-(1,3-Benzodioxol-5-yl)propanoyl] amino}benzoyl)hydrazono]-5-iodo-2-oxo-2,3-dihydro-1H-indol-1-yl}acetic acid, N-methyl-D-glucamine (1-deoxy-1-(methylamino)glucitol) salt The same procedure as employed in the preparation of Example 92 but using {3-[(4-{[(3-(1,3-benzodioxol-5-yl) propanoyl]amino benzoyl)hydrazono]-5-iodo-2-oxo-2,3-dihydro-1H-indol-1-yl}acetic acid gave the title compound (179 mg, 80%) as a yellow solid in 99.9% purity by HPLC (MaxPlot detection between 230 and 400 nm).

M.p. 140-145° C. (decomp).

Example 101

Methyl 6-[(4-{[2-(5-iodo-2-oxo-1,2-dihydro-3H-indol-3-ylidene)hydrazino]-carbonyl}phenyl)amino]-6-oxohexanoate a) Preparation of tert-butyl 2-{4-[(6-methoxy-6-oxohexanoyl)amino]benzoyl}hydrazinecarboxylate (Compound B of Scheme 2)

To a solution of tert-butyl 2-(4-aminobenzoyl)hydrazinecarboxylate (1.0 g, 3.98 mmol) in anhydrous pyridine (20 mL) was added dropwise methyl 6-chloro-6-oxohexanoate (Fluka) (750 µL) at rt. After 30 min, aminomethyl resin (Polymers Laboratories PL-AMS, 1.96 mmol/g, 970 mg) was added and the resulting mixture was stirred overnight at rt. After filtration and rinsing the resin, water (160 mL) was added into the filtrate and a white solid precipitated out. Filtration and washing with water gave a white solid, which was dried under vacuo at 50° C. for 5 hrs. The title compound (981 mg) was obtained as a white solid (63%) in 99.8% purity by HPLC (MaxPlot detection between 230 and 400 nm).

M.p. 163° C.

$^1$H NMR (300 MHz, DMSO-$d_6$) δ 10.13 (s, 1H), 10.05 (s, 1H), 8.84 (s, 1H), 7.81 (d, J=8.5 Hz, 2H), 7.66 (d, J=8.4 Hz, 2H), 357 (s, 3H), 2.34 (m, 4H), 1.58 (m, 4H), 1.14 (s, 9H).

M$^-$(ESI (LC/MS)$^-$): 392; M$^+$(ESI (LC/MS)$^+$): 394.

b) Preparation of methyl 6-[(4-{[2-(5-iodo-2-oxo-1, 2-dihydro-3H-indol-3-ylidene)hydrazino] carbonyl}phenyl)amino]-6-oxohexanoate (Scheme 1)

Following the general method as outlined in Example 1, into a suspension of 5-iodo-1H-indole-2,3-dione in acetic acid in the presence of 5% TFA was added tert-butyl 2-{4-[(6-methoxy-6-oxohexanoyl)amino]benzoyl}hydrazinecarboxylate. After stirring at 100° C., the reaction mixture was cooled to rt and a yellow solid precipitated out. Filtration on a fritté, washing with AcOH, water and drying under vacuo at 70° C. for 15 hrs gave 496 mg of the title compound (82%) as a yellow solid in 99.5% purity by HPLC (MaxPlot detection between 230 and 400 nm).

M.p. 277° C.

$^1$H NMR (300 MHz, DMSO-$d_6$) δ 13.81 (s, 1H), 11.46 (s, 1H), 10.29 (s, 1H), 7.82 (m, 5H), 7.71 (d, J=7.9 Hz, 1H), 6.81 (d, J=7.9 Hz, 1H), 3.58 (s, 3H), 2.35 (m, 4H), 1.58 (m, 4H).

M$^-$(APCI$^-$): 547. M$^+$(APCI$^+$): 549.

Example 102

Methyl 4-{[(4-{[2-(5-iodo-2-oxo-1,2-dihydro-3H-indol-3-ylidene)-hydrazino]carbonyl}phenyl)amino] carbonyl}benzoate a) Preparation of tert-butyl 2-(4-{[4-(methoxycarbonyl)benzoyl]amino}benzoyl)hydrazinecarboxylate (Compound B of Scheme 2)

To a solution of tert-butyl 2-(4-aminobenzoyl)hydrazinecarboxylate (1.0 g, 3.98 mmol) in anhydrous pyridine (20 mL) was added dropwise methyl 4-(chlorocarbonyl)benzoate (TCI) (948 mg, 4.78 mmol) at rt. After 50 min, aminomethyl resin (Polymers Laboratories PL-AMS, 1.96 mmol/g, 960 mg) was added and the resulting mixture was stirred for 22 hrs at rt After filtration and rinsing the resin, water (160 mL) was added into the filtrate and a white solid precipitated out. Filtration and washing with water gave a white solid, which was dried under vacuo at 60° C. for 15 hrs. The title compound (1.41 g) was obtained as a white solid (85%) in 98.7% purity by HPLC (MaxPlot detection between 230 and 400 mn).

$^1$H NMR (300 MHz, DMSO-$d_6$) δ 10.66 (s, 1H), 10.12 (s, 1H), 8.87 (s, 1H), 8.09 (m, 4H), 7.87 (m, 4H), 3.89 (s, 3H), 1.42 (s, 9H).

M$^-$(APCI$^-$): 412.

b) Preparation of methyl 4-{[(4-{[2-(5-iodo-2-oxo-1, 2dihydro-3H-indol-3-ylidene)hydrazino] carbonyl}phenyl)amino]carbonyl}benzoate (Scheme 1)

Following the general method as outlined in Example 1, into a suspension of 5-iodo-1H-indole-2,3-dione in acetic acid in the presence of 5% TFA was added tert-butyl 24-{[4-(methoxycarbonyl)benzoyl]amino}benzoyl)hydrazinecarboxylate. After stirring at 100° C., the reaction mixture was cooled to rt and a yellow solid precipitated out. Filtration on a fritté, washing with AcOH, water and drying under vacuo at 60° C. for 72 hrs gave 636 mg of the title compound (97%) as a yellow solid in 95.3% purity by HPLC (MaxPlot detection between 230 and 400 nm).

M.p. 361° C. (decomp.).

$^1$H NMR (300 MHz, DMSO-$d_6$) δ 13.84 (s, 1H), 11.47 (s, 1H), 10.81 (s, 1H), 8.05 (s, 4H), 8.02 (d, J=8.66 Hz, 2H), 7.91 (d, J=8.29 Hz, 2H), 7.83 (s, 1H), 7.71 (d, J=8.29 Hz, 1H), 6.81 (d, J=8.29 Hz, 1H), 3.90 (s, 3H).

M$^-$(APCI$^-$): 567. M$^+$(APCI$^+$): 569.

Example 103

Methyl 8-[(4-{[2-(5-iodo-2-oxo-1,2-dihydro-3H-indol-3-ylidene)hydrazino]-carbonyl}phenyl)amino]-8-oxooctanoate a) Preparation of tert-butyl 2-{4-[(9-methoxy-9-oxononanoyl)amino]benzoyl}hydrazinecarboxylate (Compound B of Scheme 2)

To a solution of tert-butyl 2-(4-aminobenzoyl)hydrazinecarboxylate (1.0 g, 3.98 mmol) in anhydrous pyridine (20 mL) was added dropwise methyl 8-chloro-8-oxo-octanoate (Aldrich) (680 μL, 4.78 mmol) at rt. After 90 min, aminomethyl resin (Polymers Laboratories PL-AMS, 1.96 mmol/g, 960 mg) was added and the resulting mixture was stirred for 20 hrs at rt. After filtration and rinsing the resin, water (160 mL) was added into the filtrate and a white solid precipitated out. Filtration and washing with water gave a white solid, which was dried undervacuo at 70° C. for 3 hrs. The title compound (1.11 g) was obtained as a white solid (65%) in 98.7% purity by HPLC (MaxPlot detection between 230 and 400 nm).

M.p. 106-109° C. (decomp.).

$^1$H NMR (300 MHz, DMSO-$d_6$) δ 10.11 (s, 1H), 10.04 (s, 1H), 8.83 (s, 1H), 7.78 (d, J=8.4 Hz, 2H), 7.66 (d, J=8.4 Hz, 2H), 3.56 (s, 3H), 2.30 (m, 4H), 1.57 (m, 4H), 1.14 (s, 9H), 1.28 (m, 4H).

M$^-$(APCI$^-$): 420.

b) Preparation of methyl 8-[(4-{[2-(5-iodo-2-oxo-1, 2-dihydro-3H-indol-3-ylidene)hydrazino] carbonyl}phenyl)amino]-8-oxooctanoate (Scheme 1)

Following the general method as outlined in Example 1, into a suspension of 5-iodo-1H-indole-2,3-dione in acetic acid in the presence of 5% TFA was added tert-butyl 2-{4-[(9-methoxy-9-oxononanoyl)amino]benzoyl)hydrazinecarboxylate. After stirring at 100° C., the reaction mixture was cooled to rt and a yellow solid precipitated out. Filtration on a fritté, washing with AcOH, water and drying under vacuo at 70° C. for 21 hrs gave 611 mg of the title compound (95%) as a yellow solid in 98.1% purity by HPLC (MaxPlot detection between 230 and 400 nm).

M.p. 268° C.

$^1$H NMR (300 MHz, DMSO-$d_6$) δ 13.81 (s, 1H), 11.45 (s, 1H), 10.27 (s, 1H), 7.81 (m, 5H), 7.69 (d, J=7.9 Hz, 1H), 6.80 (d, J=7.9 Hz, 1H), 3.56 (s, 3H), 2.29 (m, 4H), 1.57 (m, 4H), 1.29 (m, 4H).

M$^-$(APCI$^-$): 575.

Example 104

Methyl 5-[(4-{2-(5-iodo-2-oxo-1,2-dihydro-3H-indol-3-ylidene)hydrazino]-carbonyl}phenyl)amino]-5-oxopentanoate a) Preparation of tert-butyl 2-{4-[(6-methoxy-6-oxohexanoyl)amino]benzoyl}hydrazinecarboxylate (Compound B of Scheme 2)

To a solution of tert-butyl 2-(4-aminobenzoyl)hydrazinecarboxylate (1.0 g, 3.98 mmol) in anhydrous pyridine (20 mL) was added dropwise methyl 6-chloro-6-oxohexanoate (Aldrich) (660 μL, 4.78 mmol) at rt. After 90 min, aminomethyl resin (Polymers Laboratories PL-AMS, 1.96 mmol/g, 960 mg) was added and the resulting mixture was stirred for 20 hrs at rt. After filtration and rinsing the resin, water (200 mL) was added into the filtrate and a white solid precipitated out. Filtration and washing with water gave a white solid, which was dried under vacuo at 70° C. for 3 hrs. The title compound (1.27 g) was obtained as a white solid (80%) in 95.1% purity by HPLC (MaxPlot detection between 230 and 400 nm).

M.p. 125-127° C. (decomp.).

$^1$H NMR (300 MHz, DMSO-$d_6$) δ 10.15 (s, 1H), 10.05 (s, 1H), 8.84 (s, 1H), 7.80 (d, J=8.5 Hz, 7.65 (d, J=8.5 Hz, 2H), 3.58 (s, 3H), 2.40 (m, 4H), 1.8 (m, 2H), 1.78 (s, 9H).

M$^-$(APCI$^-$): 378.

b) Preparation of methyl 5-[(4-{[2-(5-iodo-2-oxo-1, 2-dihydro-3H-indol-3-ylidene)hydrazino]carbonyl) phenyl)amino]-5-oxopentanoate (Scheme 1)

Following the general method as outlined in Example 1, into a suspension of 5-iodo-1H-indole-2,3one in acetic acid in the presence of 5% TFA was added tert-butyl 2-{4-[(6-methoxy-6-oxohexanoyl)amino]benzoyl}hydrazinecarboxylate. After stirring at 100° C., the reaction mixture was cooled to rt and a yellow solid precipitated out. Filtration on a fritté, washing with AcOH, water and drying under vacuo at 70° C. for 21 hrs gave 546 mg of the title compound (93%) as a yellow solid in 99.2% purity by HPLC (MaxPlot detection between 230 and 400 nm).

M.p. 282° C.

¹H NMR (300 MHz, DMSO-d₆) δ 13.81 (s, 1H), 11.45 (s, 1H), 10.31 (s, 1H), 7.86-7.78 (m, 5H), 7.70 (d, J=8.29 Hz, 1H), 6.80 (d, J=8.29 Hz, 1H), 3.59 (s, 3H), 2.35 (m, 4H), 1.80 (m, 2H).

M⁻(APCI⁻): 533.

Example 105

8-[(4-{(2-(5-Iodo-2-oxo-1,2-dihydro-3H-indol-3-ylidene)hydrazino]-carbonyl}phenyl)amino]-8-oxooctanoic acid Into a suspension of methyl 8-[(4-{[2-(5-iodo-2-oxo-1,2-dihydro-3H-indol-3-ylidene)hydrazino]carbonyl}phenyl)amino]-8-oxooctanoate (420 mg, 0.73 mmol) in THF/H₂O (2/1) (15 mL) was added NaOH (1.0 N, 3.6 mL). The resulting solution was stirred at rt for 2.5 hr and quenched with HCl (5 N, 2 mL). A yellow solid precipitated out. Filtration, washing with water (4×5 mL) and drying under vacuo at 70° C. for 20 hrs gave the title compound as a yellow powder (340 mg, 82%) in 99.1% purity by HPLC (MaxPlot detection between 230 and 400 nm).

M.p. 276° C. (decomp).

¹H NMR (300 MHz, DMSO-d₆) δ 13.81 (s,1H), 11.97 (s, 1H), 11.46 (s, 1H), 10.27 (s, 1H), 7.82 (m, 5H), 7.70 (d, J=7.9 Hz, 1H), 6.80 (d, J=7.9 Hz, 1H), 2.36 (m, 2H), 2.20 (m, 2H), 2.20 (m, 4H), 1.29 (m, 4H).

M⁻(APCI⁻): 561.

Example 106

8-[(4-{[2-(5-Iodo-2-oxo-1,2-dihydro-3H-indol-3-ylidene)hydrazino]-carbonyl}phenyl)amino]-8-oxooctanoic acid, N-methyl-D-glucamine (1-deoxy-1-(methylamino)glucitol) salt A solution of N-methyl-D-glucamine (127 mg, 0.66 mmol) and 8-[(4-{[2-(5-iodo-2-oxo-1,2dihydro-3H-indol-3-ylidene)hydrazino]carbonyl}phenyl)amino]-8-oxooctanoic acid (331 mg, 0.55 mmol) in MeOH/DMSO (5/1) (120 mL) was stirred at 70° C. for 15 min. The heating bath was removed and Et₂O (500 mL) was added. A yellow solid precipitated out. Filtration, washing with Et₂O (5×10 mL) and drying under vacuo at 40° C. for 96 hrs gave a title compound as a yellow solid (331 mg, 79%) in 98.9% purity by HPLC (MaxPlot detection between 230 and 400 nm).

M.p. 238° C. (decomp).

Example 107

6-[(4-{[2-(5-Iodo-2-oxo-1,2-dihydro-3H-indol-3-ylidene)hydrazino]-carbonyl}phenyl)amino]-6-oxohexanoic acid Into a suspension of methyl 6-[(4-{[2-(5-iodo-2-oxo-1,2-dihydro-3H-indol-3-ylidene)hydrazino]carbonyl}phenyl)amino]-6-oxohexanoate (405 mg, 0.74 mmol) in THF/H₂O (2/1) (15 mL) was added NaOH (1.0 N, 3.7 mL). The resulting solution was stirred at rt for 2.5 hr and quenched with HCl (5 N, 2 mL). A yellow solid precipitated out. Filtration, washing with water (4×5 mL) and drying under vacuo at 70° C. for 20 hrs gave the title compound as a yellow powder (363 mg, 91%) in 99.0% purity by HPLC (MaxPlot detection between 230 and 400 mn).

M.p. 286° C.

¹H NMR (300 MHz, DMSO-d₆) δ 13.81 (s, 1H), 12.03 (s, 1H), 11.45 (s, 1H), 10.29 (s, 1H), 7.70 (m, 6H), 6.82 (m, 1H), 2.36 (m, 2H), 2.24 (m, 2H), 1.75 (m, 2H), 1.58 (m, 2H).

M⁻(APCI⁻): 533.

Example 108

6-[(4-{[2-(5-Iodo-2-oxo-1,2-dihydro-3H-indol-3-ylidene)hydrazino]-carbonyl}phenyl)amino]-6-oxohexanoic acid, N-methyl-D-glucamine (1-deoxy-1-(methylamino)glucitol) salt A solution of N-methyl-D-glucamine (125 mg, 0.64 mmol) and 6-[(4-{[2-(5-iodo-2-oxo-1,2-dihydro-3H-indol-3-ylidene)hydrazino]carbonyl}phenyl)amino]-6-oxohexanoic acid (297 mg, 0.56 mmol) in MeOH/DMSO (5/1) (60 mL) was stirred at 70° C. for 15 min. The heating bath was removed and Et₂O (250 mL) was added. A yellow solid precipitated out Filtration, washing with Et₂O (6×10 mL) and drying under vacuo at 60° C. for 15 hrs gave a title compound as a yellow solid (311 mg, 76%) in 99.3% purity by HPLC (MaxPlot detection between 230 and 400 nm).

M.p. 223° C. (decomp).

Example 109

4-[(4-{[2-(5-Iodo-2-oxo-1,2-dihydro-3H-indol-3-ylidene)hydrazino]-carbonyl}phenyl)amino]-4-oxobutanoic acid Into a suspension of methyl 4-[(4-{[2-(5-iodo-2-oxo-1,2-dihydro-3H-indol-3-ylidene)hydrazino]carbonyl}phenyl)amino]4-oxobutanoate (250 mg, 0.48 mmol) in THF/H₂O (2/1) (10 mL) was added NaOH (1.0 N, 2.4 mL). The resulting solution was stirred at rt for 1.5 hr and quenched with HCl (5 N, 2 mL). A yellow solid precipitated out. Filtration, washing with water (2×5 mL) and drying under vacuo at 70° C. for 20 hrs gave the title compound as a yellow powder (83 mg, 34%) in 99.2% purity by HPLC (MaxPlot detection between 230 and 400 nm).

M.p. 299° C. (decomp.).

¹H NMR (300 MHz, DMSO-d₆) δ 13.82 (s, 1H), 12.16 (s, 1H), 11.46 (s, 1H), 10.38 (s, 1H), 7.82 (m, 5H), 7.70 (d, J=7.9 Hz, 1H), 6.81 (d, J=7.9 Hz, 1H), 2.60 (d, J=5.3 Hz, 2H), 2.54 (d, J=5.7 Hz, 2H).

M⁻(APCI⁻): 505.

Example 110

4-[(4-{[2-(5-Iodo-2-oxo-1,2-dihydro-3H-indol-3-ylidene)hydrazino]-carbonyl}phenyl)amino]-4-oxobutanoic acid, N-methyl-D-glucamine (1-deoxy-1-(methylamino)glucitol) salt Into a solution of N-methyl-D-glucamine (30 mg, 0.15 mmol) in MeOH (10 mL) at reflux was added a solution of 4-[(4-{[2-(5-iodo-2-oxo-1,2-dihydro-3H-indol-3-ylidene)hydrazino]carbonyl}phenyl)amino]oxobutanoic acid (70 mg, 0.14 mmol) in warm DMSO (2 mL). After 10 min of stirring, the heating bath was removed and Et₂O (50 mL) was added. A yellow solid precipitated out Filtration, washing with Et₂O (6×3 mL) and drying under vacuo at 60° C. for 15 hrs gave a title compound as a yellow solid (75 mg, 77%) in 99.5% purity by HPLC (MaxPlot detection between 230 and 400 nm).

M.p. 203° C.

Example 111

5-[(4-{[(2-(5-Iodo-2-oxo-1,2-dihydro-3H-indol-3-ylidene)hydrazino]-carbonyl}phenyl)amino]-5-oxopentanoic acid Into a suspension of methyl 5-[(4-{[2-(5-iodo-2-oxo-1,2-dihydro-3H-indol-3-ylidene)hydrazino]carbonyl}phenyl)amino]-5-oxopentanoate (502 mg, 0.94 mmol) in THF/H$_2$O (2/1) (20 mL) was added NaOH (1.0 N, 4.7 mL). The resulting solution was stirred at rt for 2 hr and quenched with HCl (5 N, 4 mL). A yellow solid precipitated out. Filtration, washing with water (4×5 mL) and drying under vacuo at 70° C. for 20 hrs gave the title compound as a yellow powder (381 mg, 77%) in 98.3% purity by HPLC (MaxPlot detection between 230 and 400 mn).

M.p. 296° C. (decomp.).

$^1$H NMR (300 MHz, DMSO-d$_6$) δ 13.81 (s, 1H), 12.09 (s, 1H), 11.46 (s, 1H), 10.31 (s, 1H), 7.86-7.78 (m, 5H), 7.70 (d, J=8.29 Hz, 1H), 6.80 (d, J=8.29 Hz, 1H), 2.43 (m, 2H), 2.30 (m, 2H), 1.8 (m, 2H).

M$^-$(APCI$^-$): 519.

Example 112

5-[(4-{[(2-(5-Iodo-2-oxo-1,2-dihydro-3H-indol-3-ylidene)hydrazino]-carbonyl}phenyl)amino]-5-oxopentanoic acid, N-methyl-D-glucamine (1-deoxy-1-(methylamino)glucitol) salt Into a solution of N-methyl-D-glucamine (128 mg, 0.66 mmol) in MeOH (50 mL) at reflux was added a solution of 5-[(4-{[(2-(5-iodo-2-oxo-1,2-dihydro-3H-indol-3-ylidene)hydrazino]carbonyl}phenyl)amino]-5-oxopentanoic acid (310 mg, 0.60 mmol) in DMSO (10 mL). After 10 min of stirring, the heating bath was removed and Et$_2$O (250 mL) was added. A yellow solid precipitated out. Filtration, washing with Et$_2$O (6×5 mL) and drying under vacuo at 60° C. for 15 hrs gave a title compound as a yellow solid (350 mg, 83%) in 99.9% purity by HPLC (MaxPlot detection between 230 and 400 nm).

M.p. 228° C. (decomp.).

Example 113

4-{[(4-{[2-(5-Iodo-2-oxo-1,2-dihydro-3H-indol-3-ylidene)hydrazino]-carbonyl}phenyl)amino]carbonyl}benzoic acid Into a suspension of methyl 4-{[(4-{[2-(5-iodo-2-oxo-1,2dihydro-3H-indol-3-ylidene)hydrazino]carbonyl}phenyl)amino]carbonyl)benzoate (546 mg, 0.96 mmol) in THF/H$_2$O (2/1) (20 mL) was added NaOH (1.0 N, 4.8 mL). The resulting solution was stirred at rt for 2 hr and quenched with HCl (5 N, 4 mL). A yellow solid precipitated out. Filtration, washing with water (4×5 mL) and drying under vacuo at 70° C. for 20 hrs gave the title compound as a yellow powder (451 mg, 86%) in 97.0% purity by HPLC (MaxPlot detection between 230 and 400 nm).

M.p. 362° C. (decomp.).

$^1$H NMR (300 MHz, DMSO-d$_6$) δ 13.85 (br s, 1H), 13.28 (br s, 1H), 11.47 (s, 1H), 10.78 (s, 1H), 8.07 (s, 4H), 8.03 (d, J=8.3 Hz, 2H), 7.92 (d, J=8.3 Hz, 2H), 7.83 (s, 1H), 7.71 (d, J=8.1 Hz, 1H), 6.81 (d, J=8.1 Hz, 1H).

M$^-$(APCI$^-$): 553.

Example 114

4-{[(4-{[2-(5-Iodo-2-oxo-1,2-dihydro-3H-indol-3-ylidene)hydrazino]-carbonyl}phenyl)amino]carbonyl}benzoic acid, N-methyl-D-glucamine (1-deoxy-1-(methylamino)glucitol) salt Into a solution of N-methyl-D-glucamine (204 mg, 1.05 mmol) in MeOH (80 mL) at reflux was added a solution of 4-{[(4-{[2-(5-iodo-2-oxo-1,2-dihydro-3H-indol-3-ylidene)hydrazino]carbonyl}phenyl)amino]carbonyl}benzoic acid (387 mg, 0.70 mmol) in warm DMSO (20 mL). After 10 min of stirring, the heating bath was removed and Et$_2$O (300 mL) was added. A yellow solid precipitated out. Filtration, washing with Et$_2$O (5×5 mL) and drying under vacuo at 40° C. for 15 hrs gave a title compound as a yellow solid (432 mg, 81%) in 97.9% purity by HPLC (MaxPlot detection between 230 and 400 nm).

M.p. 133° C. (decomp.).

Example 115

Methyl 4-{[(4-{[2-(5-iodo-2-oxo-1,2-dihydro-3H-indol-3-ylidene)hydrazino]carbonyl}benzyl)amino]carbonyl}benzoate a) Preparation of 4-({[4-(methoxycarbonyl)benzoyl]amino}methyl)benzoic acid (Compound C)

Into a solution of 4-(aminomethyl)amino benzoic acid (5.0 g, 33.1 mmol) in anhydrous THF (200 mL) were added DIEA (12.45 mL, 72.7 mmol) and tert-butyl dimethyl chlorosilane (5.48 g, 36.4 mmol). The resulting mixture was allowed to stir at rt for 1 hr and methyl 4-(chlorocarbonyl)benzoate (7.23 g, 36.4 mmol) was added neat. After overnight stirring at rt, the reaction mixture was quenched with HCl (0.1N, 250 mL) until pH=1. Extraction with EtOAc/THF (400 mL), drying over MgSO$_4$, evaporation under vacuo gave the title compound as a white powder (7.0 g, 67%).

$^1$H NMR (300 MHz, DMSO-d$_6$) δ 12.87 (s, 1H), 9.33 (t, J=5.8 Hz, 1H), 8.05 (m, 4H), 7.91 (d, J=8.3 Hz, 2H), 7.44 (d, J=8.3 Hz, 2H), 4.56 (d, J=5.8 Hz, 2H), 3.88 (s, 3H).

M$^+$(ESI (LC/MS)$^+$): 314. M$^-$(ESI (LC/MS)$^-$): 312.

b) Preparation of tert-butyl 2-[4-({[4-(methoxycarbonyl)benzoyl]amino}-methyl)-benzoyl]hydrazinecarboxylate (Compound B, Scheme 2)

Into a solution of 4-({[4-(methoxycarbonyl)benzoyl]amino}methyl)benzoic acid (1.0 g, 3.19 mmol) and N-methyl morpholine (420 µL, 3.83 mmol) in anhydrous THF (25 mL) at 0° C. was added isobutyl chloroformate (455 µL, 3.51 mmol) then tert-butyl hydrazine carboxylate (1.12 mg, 7.66 mmol). After stirring at 0° C. for 1 hr and overnight at rt, the reaction mixture was quenched with HCl (1N, 25 mL). Extraction with EtOAc (2×25 mL), drying over MgSO$_4$ and evaporation under vacuo gave a residue. Purification by flash chromatography (SiO$_2$, EtOAc) gave the title compound (773 mg, 55%) as a white powder.

$^1$H NMR (300 MHz, DMSO-d$_6$) δ 10.16 (s, 1H), 9.31 (t, J=5.9 Hz, 1H), 8.89 (s, 1H), 8.05 (m, 4H), 7.82 (d, J=7.7 Hz, 2H), 7.42 (d, J=7.7 Hz, 2H), 4.55 (d, J=5.9 Hz, 2H), 3.88 (s, 3H), 1.42 (s, 9H).

M$^-$(ESI (LC/MS)$^-$): 426.

c) Preparation of methyl 4-{[(4-{[2-(5-iodo-2-oxo-1, 2-dihydro-3H-indol-3-ylidene)hydrazino] carbonyl}benzyl)amino]carbonyl}benzoate Following the general method as outlined in Example 1, into a suspension of 5-iodo-1H-indole-2,3-dione in acetic acid in the presence of 5% TFA was added tert-butyl 2-[4-({[4-(methoxycarbonyl)benzoyl]amino}methyl)benzoyl]hydrazinecarboxylate. After stirring at 100° C., the reaction mixture was cooled to rt and a yellow solid precipitated out. Filtration on a fritté, washing with AcOH, water and drying under vacuo at 70° C. for 15 hrs gave 614 mg of the title compound (86%) as a yellow solid in 97.9% purity by HPLC (MaxPlot detection between 230 and 400 nm).

M.p. 323° C. (decomp.).

$^1$H NMR (300 MHz, DMSO-$d_6$) δ 13.83 (s, 1H), 11.46 (s, 1H), 9.34 (t, J=7.5 Hz, 1H), 8.04 (m, 4H), 7.84 (m, 3H), 7.71 (d, J=8.3 Hz, 1H), 7.55 (d, J=7.9 Hz, 2H), 6.80 (d, J=8.3 Hz, 1H), 4.58 (d, J=7.5 Hz, 2H), 3.87 (s, 3H).

M$^-$(APCI$^-$): 581. M$^+$(APCI$^+$): 583.

Example 116

4-{[(4-{[2-(5-Iodo-2-oxo-1,2-dihydro-3H-indol-3-ylidene)hydrazino]-carbonyl}benzyl)amino] carbonyl}benzoic acid Into a suspension of methyl 4-{[(4-{[2-(5-iodo-2-oxo-1, 2dihydro-3H-indol-3-ylidene)hydrazino]carbonyl}benzyl) amino]caxbonyl}benzoate (510 mg, 0.88 mmol) in THF/H$_2$O (2/1) (20 mL) was added NaOH (1.0 N, 4.4 mL). The resulting solution was stirred at rt for 1.5 hr and quenched with HCl (5 N, 4 mL). An orange solid precipitated out. Filtration, washing with water (4×5 mL) and drying under vacuo at 70° C. for 20 hrs gave the title compound as a yellow powder (436 mg, 84%) in 96.3% purity by HPLC (MaxPlot detection between 230 and 400 nm).

$^1$H NMR (300 MHz, DMSO-$d_6$) δ 13.83 (s, 1H), 13.21 (s, 1H),11.46 (s, 1H), 9.33 (br s, 1H), 8.02 (m, 4H), 7.85 (m, 3H), 7.70 (d, J=8.3 Hz, 1H), 7.55 (d, J=7.2 Hz, 2H), 6.79 (d, J=8.3 Hz, 1H), 4.60 (br s, 2H).

M$^-$(APCI$^-$): 567.

Example 117

4-{[(4-{[2-(5-Iodo-2-oxo-1,2-dihydro3H-indol-3-3-ylidene)hydrazino]-carbonyl}benzyl)amino] carbonyl}benzoic acid, N-methyl-D-glucamine (1-deoxy-1-(methylamino)glucitol) salt Into a solution of N-methyl-D-glucamine (157 mg, 0.80 mmol) in MeOH (50 mL) at reflux was added a solution of 4-{[(4-{[2-(5-iodo-2-oxo-1,2dihydro-3H-indol-3-ylidene) hydrazino]carbonyl}benzyl)amino]carbonyl}benzoic acid (380 mg, 0.67 mmol) in THF (10 mL). After 10 min of stirring, the heating bath was removed and Et$_2$O (50 mL) was added. A yellow solid precipitated out. Filtration, washing with Et$_2$O (3×50 mL) and drying under vacuo at 60° C. for 24 hrs gave a title compound as a yellow solid (400 mg, 78%) in 98.9% purity by HPLC (MaxPlot detection between 230 and 400 nm).

M.p. 301° C.

Example 118

Benzyl (2S)-2-(4-{[2-(5-iodo-2-oxo-1,2-dihydro-3H-indol-3-ylidene)hydrazino]carbonyl}phenoxy)-3-phenylpropanoate a) Preparation of tert-butyl 2-(4-hydroxybenzoyl)hydrazinecarboxylate (Precursor of Compound B)

Into a solution of 4-hydroxybenzo hydrazide (5.0 g, 32.86 mmol) in anhydrous THF (200 mL) was added a solution of di-tert-butyl dicarbonate (Aldrich) (7.53 g, 34.51 mmol) in anhydrous THF (10 mL). The resulting mixture was stirred at rt for 6 d. After addition of Et$_2$O (800 ml), a white solid precipitated out. Filtration, washing with Et$_2$O (3×20 mL) and drying under vacuo at 50° C. for 5 hr gave the title compound (5.32 g, 64%) as a white powder in a in 99.9% purity by HPLC (MaxPlot detection between 230 and 400 nm).

$^1$H NMR (300 MHz, DMSO-$d_6$) δ 10.05 (s, 1H), 9.91 (s, 1H), 8.77 (s, 1H), 7.72 (d, J=8.5 Hz, 2H), 6.80 (d, J=8.5 Hz, 2H), 1.41 (s, 9H).

b) Preparation of tert-butyl 2-{4-[(1S)-1-benzyl-2-(benzyloxy)-2-oxoethoxy] benzoyl}hydrazinecarboxylate (Compound B)

Into a solution of tert-butyl 2(4-hydroxybenzoyl)hydrazinecarboxylate (200 mg, 0.79 mmol) and benzyl (R)-(+)-2-hydroxy-3-phenylpropionate (Aldrich) (270 μL, 1.19 mmol) were added triphenylphosphine polymer bound (Fluka, 3 mmol/g, 400 mg) and diethyl azodicarboxylate (190 μL) at 0° C. The resulting mixture was allowed to stir for 2 hr at 0° C. After filtration and rinsing the resin with DCM, the filtrate was evaporated off under vacuo to give a brown residue. Purification by flash chromatography (SiO2, AcOEt/chexanes (2/3)) gave the title compound as a white powder (216 mg, 56%) in 99.4% purity by HPLC (MaxPlot detection between 230 and 400 nm).

$^1$H NMR (300 MHz, DMSO-$d_6$) δ 10.04 (s, 1H), 8.83 (s, 1H), 7.76 (d, J=8.5 Hz, 2H), 7.33-7.20 (m, 10H), 6.94 (d, J=8.7 Hz, 2H), 5.32 (t, J=6.4 Hz, 1H), 5.13 (d, J=12.4 Hz, 1H), 5.08 (d, J=12.4 Hz, 1H), 3.22 (d, J=6.4 Hz, 2H), 1.41 (s, 9H).

M$^-$(APCI$^-$): 489.

c) Preparation of benzyl (2S)-2-(4-{[2-(5-iodo-2-oxo-1,2-dihydro-3H-indol-3-ylidene)hydrazino] carbonyl}phenoxy)-3-phenylpropanoate Following the general method as outlined in Example 1, into a suspension of 5-iodo-1H-indole-2,3-dione in acetic acid in the presence of 5% TFA was added tert-butyl 2-{4-[(1S)-1-benzyl-2-(benzyloxy)-2-oxoethoxy] benzoyl}hydrazinecarboxylate. After stirring at 100° C., the reaction mixture was cooled to rt and a yellow solid precipitated out. Filtration on a fritté, washing with AcOH, water and drying under vacuo at 60° C. for 15 hrs gave 164 mg of the title compound (76%) as a yellow solid in 98.8% purity by HPLC (MaxPlot detection between 230 and 400 nm).

M.p. 194° C.

$^1$H NMR (300 MHz, DMSO-$d_6$) δ 13.76 (s, 1H), 11.46 (s, 1H), 7.80 (m, 3H), 7.71 (d, J=8.1 Hz, 1H), 7.28 (m, 10H), 7.08 (d, J=8.3 Hz, 2H), 6.80 (d, J=8.1 Hz, 1H), 5.39 (br s, 1H), 5.13 (s, 2H), 3.26 (br s, 2H).

M$^-$(APCI$^-$): 644. M$^+$(APCI$^+$): 646.

Example 119

(2S)-2-(4-{[2-(5-Iodo-2-oxo-1,2-dihydro-3H-indol-3-ylidene)hydrazino]-carbon}phenoxy)-3-phenylpropanoic acid Into a suspension of benzyl (2S)-2-(4-{[2-(5-iodo-2-oxo-1,2-dihydro-3H-indol-3-ylidene)hydrazino]carbonyl}phenoxy)-3-phenylpropanoate (132 mg, 0.20 mmol) in THF/H$_2$O (2/1) (5 mL) was added NaOH (1.0 N, 0.5 mL). The resulting solution was stirred at rt for 1 hr and quenched with HCl (5 N, 0.5 mL). After addition of water (15 mL), a yellow solid precipitated out. Filtration, washing with water (3×2 mL) and drying under vacuo at 60° C. for 15 hrs gave the title compound as a yellow powder (83 mg, 73%) in 99.4% purity by HPLC (MaxPlot detection between 230 and 400 nm).

M.p. 285° C. (decomp.).

$^1$H NMR (300 MHz, DMSO-d$_6$) δ 13.76 (s, 1H), 13.31 (s, 1H), 11.45 (s, 1H), 7.81 (m, 3H), 7.70 (d, J=7.8 Hz, 1H), 7.32-7.21 (m, 5H), 7.06 (d, J=8.3 Hz, 2H), 6.80 (d, J=7.8 Hz, 1H), 5.17 (m, 1H), 3.21 (m, 2H).

M$^-$(APCI$^-$): 554.

Example 120

(2S)-2-(4-{[2-(5-iodo-2-oxo-1,2-dihydro-3H-indol-3-ylidene)hydrazino]-carbonyl}phenoxy)-3-phenylpropanoic acid, N-methyl-D-glucamine (1-deoxy-1-(methylamino)glucitol) salt Into a solution of N-methyl-D-glucamine (160 mg, 0.82 mmol) in MeOH (50 mL) at reflux was added (2S)-2-(4-{[2-(5-iodo-2-oxo-1,2-dihydro-3H-indol-3-ylidene)hydrazino]carbonyl}phenoxy)-3-phenylpropanoic acid (396 mg, 0.71 mmol). After 10 min of stirring, the heating bath was removed and Et$_2$O (400 mL) was added. A yellow solid precipitated out. Filtration, washing with Et$_2$O (4×5 mL) and drying under vacuo at 40° C. for 72 hrs gave a title compound as a yellow solid (346 mg, 64%) in 99.4% purity by HPLC (MaxPlot detection between 230 and 400 nm).

M.p. 130° C. (decomp).

Example 121

Methyl 4-{3-[(4-{[3-(1,3-benzodioxol-5-yl)propanoyl]amino}-benzoyl)hydrazono]-5-iodo-2-oxo-2,3-dihydro-1H-indol-1-yl}butanoate a) Preparation of methyl 4-(5-iodo-2,3-dioxo-2,3-dihydro-1H-indol-1-yl)butanoate (Precursor of Compound A)

Into a solution of 5-iodo-1H-indole-2,3-dione (1.0 g, 3.66 mmol) in anhydrous THF (18 ml) were added DBU (0.82 mL, 5.49 mmol) and methyl 4-bromobutanoate (0.6 mL, 5.49 mmol). After stirring at rt for 2 hrs, the reaction mixture was quenched with water (60 mL) and HCl (IN, 10 mL). Extraction with EtOAc (3×50 mL), drying over MgSO$_4$ and evaporation under vacuo gave a residue. Purification by flash chromatography (chexanes/Et$_2$O (1/3)) gave the title compound as an orange powder (1.10 g, 71%) in 90.1% purity by HPLC (MaxPlot detection between 230 and 400 nm).

$^1$H NMR (300 MHz, DMSO-d$_6$) δ 7.97 (dd, J=8.3, 1.9 Hz, 1H), 7.79 (d, J=1.9 Hz, 1H), 7.05 (d, J=8.3 Hz, 1H), 3.66 (t, J=6.8 Hz, 2H), 3.55 (s, 3H), 2.42 (t, J=7.4 Hz, 2H), 1.81 (m, 2H); M$^+$(ESI (LC/MS)$^+$): 374.

b) Preparation of methyl 4-{[3-(1,3-benzodioxol-5-yl)propanoyl]amino}benzoate (Compound C of Scheme 2)

To a solution of 3-(3,4methylenedioxyphenyl)-propionic acid (501 mg, 2.58 mmol) in anhydrous THF (10 mL) were added N-methylmorpholine (0.28 mL, 2.58 mmol) and isobutylchloroformate (0.33 mL, 2.58 mmol) at 0° C. After 30 min, at 0° C., a solution of methyl 4-aminobenzoate (390 mg, 2.58 mmol) in anhydrous THF (2 mL) was added to the reaction mixture. After 30 min the temperature was allowed to warm up to rt and stir for 24 hrs. After extraction with EtOAc (100 mL), washing with HCl (0.1 N, 50 mL) and a saturated aqueous solution of NaHCO$_3$ (50 mL), the organic layer was dryed over sodium sulfate and evaporated under vacuo to give a solid. The residue was taken up in Et$_2$O, filtrated and washed with Et$_2$O gave the title compound as a white solid (62%) in a 99.4% purity by HPLC (MaxPlot detection between 230 and 400 nm).

$^1$H NMR (DMSO-d$_6$, 300 MHz) δ 10.22 (s, 1H), 7.89 (d, J=8.7 Hz, 2H), 7.70 (d, J=8.7 Hz, 2H), 6.82 (d, J=1.6 Hz, 1H), 6.80 (d, J=7.9 Hz, 1H), 6.68 (dd, J=7.9, 1.6 Hz, 1H), 5.94 (s, 2H), 3.80 (s, 3H), 2.82 (t, J=7.5 Hz, 2H), 2.61 (t, J=7.5 Hz, 2H).

c) Preparation of 3-(1,3-benzodioxol-5-yl)-N-[4-(hydrazinocarbonyl)phenyl]propanamide (Scheme 2, compound B)

To a suspension of methyl 4-{[3-(1,3-benzodioxol-5-yl)propanoyl]amino}benzoate (200 mg, 0.61 mmol) in EtOH (3.5 mL) was added hydrazine hydrate (0.5 mL). After stirring for 15 hrs at reflux, the reaction mixture was cooled to rt and a white solid precipitated out. Filtration, washing with EtOH (2×1 mL) and water (3×1 mL), and drying under vacuo at 70° C. for 1 hr gave 130 mg of the title compound (65%) as a white solid in 95.5% purity by HPLC (MaxPlot detection between 230 and 400 nm).

$^1$H NMR (DMSO-d$_6$, 300 MHz) δ 10.08 (s, 1H), 9.60 (s, 1H), 7.75 (d, J=8.5 Hz, 2H), 7.61 (d, J=8.5 Hz, 2H), 6.82 (d, J=1.5 Hz, 1H), 6.80 (d, J=7.9 Hz, 1H), 6.68 (dd, J=7.9, 1.5 Hz, 1H), 5.94 (s, 2H), 4.41 (s, 2H), 2.82 (t, J=7.6 Hz, 2H), 2.59 (t, J=7.6 Hz, 2H).

d) Preparation of methyl 4-{3-[(4-{[3-(1,3-benzodioxol-5-yl)propanoyl]amino}benzoyl)hydrazono]-5-iodo-2-oxo-2,3-dihydro-1H-indol-1-yl}butanoate Following the general method as outlined in Example 1, into a suspension of methyl 4-(5-iodo-2,3oxo-2,3 dihydro-1H-indol-1-yl)butanoate in acetic acid was added 3-(1,3-benzodioxol-5-yl)-N-[4-(hydrazinocarbonyl)phenyl]propanamide. After stirring at 100° C., the reaction mixture was cooled to rt and a yellow solid precipitated out. Filtration on a fritté, washing with AcOH, water and drying under vacuo at 60° C. overnight gave 188 mg of the title compound (49%) as a yellow solid in 94.3% purity by HPLC (MaxPlot detection between 230 and 400 mn).

M.p. 230° C. (decomp).

M$^-$(APCI$^-$): 681.

$^1$H NMR (DMSO-d$_4$, 300 MHz) δ 13.75 (s, 1H), 10.32 (s, 1H), 7.84 (m, 6H), 7.12 (d, J=8.3 Hz, 1H), 6.82 (m, 2H), 6.70

(d, J=7.9 Hz, 1H), 5.95 (s, 2H), 3.79 (m, 2H), 3.55 (s, 3H), 2.84 (t, J=7.4 Hz, 2H), 2.64 (t, J=7.4 Hz, 2H), 2.43 (t, J=7.0 Hz, 2H), 1.88 (m, 2H).

Example 122

4-{(3Z)-3-[(4-{[3-(1,3-Benzodioxol-5-yl)propanoyl] amino}benzoyl)-hydrazono]-5-iodo-2-oxo-2,3-dihydro-1H-indol-1-yl}butanoic acid Into a suspension of methyl 4-{3-[(4-{[3-(1,3-benzodioxol-5-yl)propanoyl]amino}benzoyl)hydrazono]-5-iodo-2-oxo-2,3-dihydro-1H-indol-1-yl}butanoate (150 mg, 0.22 mmol) in THF/$H_2O$ (2/1) (10 mL) was added NaOH (1.0 N, 1.1 mL). The resulting solution was stirred at rt for 2 hr and quenched with HCl (5 N, 4 mL). A yellow solid precipitated out. Filtration, washing with water (4×10 mL) and drying under vacuo at 60° C. for 15 hrs gave the title compound as a yellow powder (90 mg, 58%) in 95.5% purity by HPLC (MaxPlot detection between 230 and 400 nm).
$^1$H NMR (DMSO-$d_6$, 300 MHz) δ 13.77 (s, 1H), 12.11 (s, 1H), 10.32 (s, 1H), 7.84 (m, 6H), 7.12 (d, J=8.3 Hz, 1H), 6.82 (m, 2H), 6.71 (d, J=7.9 Hz, 1H), 5.96 (s, 2H), 3.79 (t, J=6.2 Hz, 2H), 2.85 (t, J=7.4 Hz, 2H), 2.64 (t, J=7.4 Hz, 2H), 2.33 (t, J=7.0 Hz, 2H), 1.80 (m, 2H).
M$^-$(ESI (LC/MS)$^-$): 667. M$^+$(ESI (LC/MS)$^+$): 669.

Example 123

4-{3-[(4-{[3-(1,3-Benzodioxol-5-yl)propanoyl] amino}benzoyl)hydrazono]-5-iodo-2-oxo-2,3-dihydro-1H-indol-1-yl}butanoic acid, N-methyl-D-glucamine (1-deoxy-1-(methylamino)glucitol) salt Into a solution of N-methyl-D-glucamine (161 mg, 0.83 mmol) in MeOH (120 mL) at reflux was added a solution of 4-{3-[(4-{[3-(1,3-benzodioxol-5-yl)propanoyl] amino}benzoyl)hydrazono]-5-iodo-2-oxo-2,3-dihydro-1H-indol-1-yl}butanoic acid (460 mg, 0.69 mmol) in DMSO (12 mL). After 10 min of stirring, the heating bath was removed and Et$_2$O (1000 mL) was added. A yellow solid precipitated out. Filtration, washing with Et$_2$O (3×50 mL) and drying under vacuo at 60° C. for 24 hrs gave a title compound as a yellow solid (424 mg, 71%) in 99.9% purity by HPLC (MaxPlot detection between 230 and 400 nm).
M.p. 135-140° C.

Example 124

Methyl 3-(4-{[(4-{[2-(5-iodo-2-oxo-1,2-dihydro-3H-indol-3-ylidene)hydrazino]carbonyl}phenyl)amino] sulfonyl}phenyl)propanoate a) Preparation of tert-butyl 2-[4-({[4-(3-methoxy-3-oxopropyl)phenyl]sulfonyl}amino)benzoyl]hydrazinecarboxylate (Compound B)

To a solution of tert-butyl 2-(4-aminobenzoyl)hydrazinecarboxylate (200 mg, 0.80 mmol) in anhydrous pyridine (4 mL) was added dropwise methyl 3-(4-chlorosulfonylphenyl) propionate (251 mg, 0.96 mmol) at rt. After 60 min, aminomethyl resin (Polymers Laboratories PL-AMS, 1.96 mmol/g, 200 mg) was added and the resulting mixture was stirred for 1 hr at rt. After filtration and rinsing the resin, water (100 mL) was added into the filtrate. Extraction with EtOAc (100 mL), washing with HCl (1N, 60 mL) and an aqueous saturated solution of NaHCO$_3$ (50 mL), drying over MgSO$_4$ and evaporation under vacuo gave a yellow oil. The residue was taken up in Et$_2$O and a white solid precipitated out. Filtration and washing with Et$_2$O gave the title compound (214 mg) was obtained as a white solid (56%) in 99.3% purity by HPLC (MaxPlot detection between 230 and 400 nm).
$^1$H NMR (300 MHz, DMSO-$d_6$) δ 10.67 (s, 1H), 10.02 (s, 1H), 8.83 (s, 1H), 7.70 (m, 4H), 7.40 (d, J=8.3 Hz, 2H), 7.16 (d, J=8.6 Hz, 2H), 3.52 (s, 3H), 2.86 (t, J=7.5 Hz, 2H), 2.63 (t, J 7.5 Hz, 2H), 1.39 (s, 9H).
M$^-$(APCI$^-$): 476.

b) Preparation of methyl 3-(4-{[(4-{[2-(5-iodo-2-oxo-1,2-dihydro-3H-indol-3-ylidene)hydrazino] carbonyl}phenyl)amino]sulfonyl}phenyl)propanoate (Scheme 1)

Following the general method as outlined in Example 1, into a suspension of 5-iodo-1H-indole-2,3-dione in acetic acid in the presence of 5% TFA was added tert-butyl 2-[4-({[4-(3-methoxy-3-oxopropyl)phenyl]sulfonyl}amino)benzoyl]hydrazinecarboxylate. After stirring at 100° C., the reaction mixture was cooled to rt and a yellow solid precipitated out. Filtration on a fritté, washing with AcOH, water and drying under vacuo at 60° C. for 60 min gave 206 mg of the title compound (87%) as a yellow solid in 98.2% purity by HPLC (MaxPlot detection between 230 and 400 nm).
M.p. 316° C. (decomp.).
$^1$H NMR (300 MHz, DMSO-$d_6$) δ 13.72 (s, 1H), 11.45 (s, 1H), 10.91 (s, 1H), 7.78 (m, 5H), 7.70 (d, J=8.1 Hz, 1H), 7.43 (d, J=7.9 Hz, 2H), 7.30 (d, J=8.3 Hz, 2H), 6.80 (d, J=8.1 Hz, 1H), 3.52 (s, 3H), 2.88 (t, J=7.3 Hz, 2H), 2.63 (t, J=7.3 Hz, 2H).
M$^-$(APCI$^-$): 631.

Example 125

3-(4-{[(4-{[2-(5-Iodo-2-oxo-1,2-dihydro-3H-indol-3-ylidene)hydrazino]-carbonyl}phenyl)amino] sulfonyl}phenyl)propanoic acid Into a suspension of methyl 3-(4-{[(4-{[2-(5-iodo-2-oxo-1,2-dihydro-3H-indol-3-ylidene)hydrazino] carbonyl}phenyl)amino]sulfonyl}phenyl)propanoate (166 mg, 0.26 mmol) in THF/$H_2O$ (2/1) (6 mL) was added NaOH (1.0 N, 1.3 mL). The resulting solution was stirred at rt for 1 hr and quenched with HCl (5 N, 1.3 mL). A yellow solid precipitated out. Filtration, washing with water (4×2 mL) and drying under vacuo at 60° C. for 18 hrs gave the title compound as a yellow powder (133 mg, 81%) in 99.3% purity by HPLC (MaxPlot detection between 230 and 400 nm).
M.p. 319° C. (decomp).
$^1$H NMR (300 MHz, DMSO-$d_6$) δ 13.71 (s, 1H), 12.16 (s, 1H), 11.44 (s, 1H), 10.90 (s, 1H), 7.77 (m, 5H), 7.70 (d, J=8.1 Hz, 1H), 7.43 (d, J=7.9 Hz, 2H), 7.29 (d, J=8.3 Hz, 2H), 6.79 (d, J=8.1 Hz, 1H), 2.84 (t, J=7.4 Hz, 2H), 2.53 (t, J=7.4 Hz, 2H).
M$^-$(APCI$^-$): 617.

Example 126

3-(4-{[(4-{[2-(5-Iodo-2-oxo-1,2-dihydro-3H-indol-3-ylidene)hydrazino]-carbonyl}phenyl)amino] sulfonyl}phenyl)propanoic acid, N-methyl-D-glucamine(1-deoxy-1-(methylamino)glucitol)salt Into a solution of N-methyl-D-glucamine (38 mg, 0.19 mmol) in MeOH (15 mL) at reflux was added a solution of 3-(4-{[(4-{[2-(5-Iodo-2-oxo-1,2dihydro-3H-indol-3-yl-idene)hydrazino]carbonyl}phenyl)amino]sulfonyl}phenyl) propanoic acid (109 mg, 0.18 mmol) in warm DMSO (1.5 mL). After 10 min of stirring, the heating bath was removed and Et$_2$O (75 mL) was added. A yellow solid precipitated out. Filtration, washing with Et$_2$O/MeOH (5/1) (4×2 mL) and Et$_2$O (4×2 mL) and drying under vacuo at 60° C. for 15 hrs gave a title compound as a yellow solid (115 mg, 80%) in 99.5% purity by HPLC (MaxPlot detection between 230 and 400 nm).

M.p. 160° C. (decomp).

Example 127

Preparation of a Pharmaceutical Formulation

Pharmaceutical formulations using the compounds of formula (I) may be prepared according to standard procedures known to a person skilled in the art.

The following formulation examples illustrate representative pharmaceutical compositions using compounds of formula (I), while it is emphasised that the present invention is not to be construed as being limited to said the below formulations.

Formulation 1—Tablets

An oxindole hydrazine derivative of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active oxindole hydrazide compound per tablet) in a tablet press.

Formulation 2—Capsules

An oxindole hydrazide derivative of formula (I) is admixed as a dry powder with a starch diluent in an approximate 1:1 weight ratio. The mixture is filled into 250 mg capsules (125 mg of active oxindole hydrazide compound per capsule).

Formulation 3—Liquid

An oxindole hydrazide derivative of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added.

Formulation 4—Tablets

An oxindole hydrazide derivative of formula (I), is admixed as a dry powder with a dry gelatin binder in an approximate 1:2 weight ratio. A minor amount of magnesium stearate is added as a lubricant. The mixture is formed into 450-900 mg tablets (150-300 mg of active oxindole hydrazide compound) in a tablet press.

Formulation 5—Injection

An oxindole hydrazide derivative of formula (I), is dissolved in a buffered sterile saline injectable aqueous medium to a concentration of approximately 5 mg/ml.

Example 128

Biological Assays

The compounds of formula (I), may be subjected to the following assays:
(1) The PTP Enzyme Assay
(2) The in vivo assay in db/db mice (1) The PTP Enzyme Assay (In Vitro Assay)

The PTP Enzyme Assay aims at determining the extent of inhibition of the examined PTP (e.g. PTP1B, TC-PTP, PTP-β, DEP-1, LAR, SHP-1, SHP-2, GLEPP-1, PTP-κ, PTP-μ, VHR, hVH5) in the presence of a test compound. The inhibition is illustrated by IC$_{50}$ values which denote the concentration necessary to achieve an inhibition of 50% of the given PTP.

a) PTPs Cloning

The cloning and expression of the catalytic domain of PTPs (e.g. PTP1B, TC-PTP, PTP-β, DEP-1, LAR, SHP-1, SHP-2, GLEPP-1, PTP-κ, PTP-μ, VHR, hVH5) maybe performed as described in *J. Biol. Chem.* 2000, 275(13), pp 9792-9796.

b) Materials and Methods

Assays were performed in a 96 well plate format, using the catalytic core of a human recombinant PTP, as an enzyme and 6,8-DiFluoro-4-MethylUmbelliferyl Phosphate (DiFMUP, Molecular Probes, D-6567) as a substrate at the Km value which was predetermined for each enzyme. Compounds to be tested were dissolved in 100% DMSO at a concentration of 2 mM. Subsequent dilutions of the test compounds (to yield a concentration of 100, 30, 10,.3, 1,0.3, 0.1,0.03, 0.01, 0.001 μM) were performed in 100% DMSO using a Tecan Stand Alone Workstation. 5 μl of diluted compound or vehicle (100% DMSO) was distributed to a black Costar 96 well plate. 25 μl of DiFMUP diluted in the assay buffer (20 mM Tris HCl pH 7.5, 0.01% IGEPAL CA-630, 0.1 mM ethylenediaminetetracetic acid, 1 mM DL-Dithiothreitol) were added, followed by 20 μl of human recombinant PTP enzyme diluted in assay buffer in order to start the reaction. The reaction ran for 30 minutes at room temperature before reading the fluorescence intensity on a Perkin-Elmer Victor 2 spectrofluorimeter (excitation at 355 nm, emission at 460 nm, for 0.1 s). The percentage of inhibition relative to the fluorescence observed in the presence of solvent (5% DMSO) alone was determined. The IC50 values for inhibition were determined in triplicates on at least 3 separate occasions.

The tested compounds according to formula (I), displayed an inhibition (illustrated by IC$_{50}$ values) with regard to PTP1B, TC-PTP, SHP and GLEPP-1 of less than 30 μM, in an embodiment an inhibition (illustrated by IC$_{50}$ values) of less than 10 μM.

The compound of Example no. 1 for instance displays an inhibition (IC$_{50}$) with regard to PTP1B of 340 nM, and of about 496 nM with regard to GLEPP-1. The compound mentioned in Example no. 70 displays an inhibition (IC$_{50}$) with regard to PTP1B of 770 nM.

(2) In Vivo Assay in db/db Mice

The following assay aims at determining the anti-diabetic effect of the test compounds of formula (I), in vivo in db/db mice using either fasted (to determine the postprandial glycemia right after a predetermined diet), or fed animals, to determine glycemia after a predetermined period of treatment.

The assays were performed as follows:

2 groups of db/db mice, 6 animals each, were formed, in the first one mice were fasted during 20 hours, the second one comprises fed (ad libitum) mice.

Group 1: The fasted animals (6) were administered (per os) a dose of 100 mg/kg of the test compound according to formula (I).

After oral administration with compounds of formula (I), they had access to commercial food (ad libitum). Blood glucose (postprandial glycemia) was determined before and 4 hrs after drug administration. Treatment decreased the blood glucose level induced by food intake by about 20-40%.

For example the compounds of Example 1 (N-(4-{[2-(5-Iodo-2-oxo-1,2-dihydro-3H-indol-3-ylidene)hydrazino]carbonyl)phenyl)-3-phenylpropanamide) and of Example 50 (N-4-{[2-(5-Iodo-2-oxo-1,2-dihydro-3H-indol-3-ylidene)hydrazino]-carbonyl}phenyl)benzamide) caused a reduction of blood glucose level of 30%, while the compound of Example no 18 (N'-(5-Iodo-2-oxo-1,2-dihydro-3H-indol-3-ylidene)-2-(4-nitrophenoxy)aceto-hydrazide) yielded a corresponding reduction of 34%.

Group 2: The fed animals (6) were administered (per os) a dose of 5×50 mg/kg of the test compound according to formula (I).

Mice were orally treated once daily during 5 days with compounds of formula (I). Blood glucose was determined before drug administration and 16 hrs after the last drug administration. A repeated oral administration (per os) using said compounds decreased the blood glucose level by about 10-30%.

The compounds of Example 1 (N-(4-([2-(5-Iodo-2-oxo-1,2-dihydro-3H-indol-3-ylidene)hydrazino]carbonyl}phenyl)-3-phenylpropanamide), 23 (Methyl 4-{2-[2-(5-iodo-2-oxo-1,2 dihydro-3H-indol-3-ylidene)hydrazino]-2-oxoethoxy}benzoate) and 26 (N-(5-Iodo-2-oxo-1,2hydro-3H-indol-3-ylidene)-3-phenoxybenzohydrazide), for instance, caused a reduction of the blood glucose level of 22%, 30% and 17% respectively.

The invention claimed is:
1. An oxindole hydrazide of formula (II)

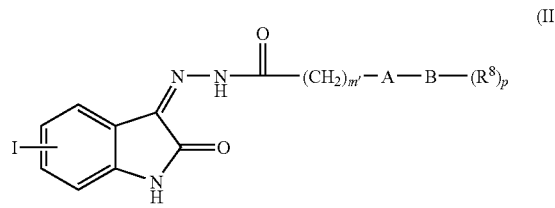

(II)

wherein A is O or a bond;

B is independently optionally substituted phenyl, naphthyl, phenantrenyl, pyrrolyl, furyl, thienyl, imidazolyl, oxazolyl, isoxazolyl, thiazolyl, isothiazolyl, pyrazolyl, [1,3]thiazolo [3,2-b][1,2,4]triazolyl, carbazolyl, 1,2,3-triazolyl, 1,2,4-triazolyl, 1,2,3-oxadiazolyl, benzo (2, 1, 3) oxadiazolyl, benzo (1,2,5) oxadiazolyl, 1,2,4-oxadiazolyl, 1,2, 5-oxadiazolyl, 1,3,4-oxadiazolyl, tetrazolyl, 1,3,4-triazinyl, 1,2,3-triazinyl, benzofuryl, [2,3- dihydro]benzofuryl, isobenzofuryi, benzothienyl, benzotriazolyl, isobenzothienyl, indolyl, isoindolyl, 3H-indolyl, benzimidazolyl, benzothiazolyl, benzoxazolyl, pyridazinyl, pyrirnidyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, cyclopropyl, cyclobutyl, cyclopentyl, cyclohexyl, cycloheptyl, cyclooctyl, oxolanyl, pyrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl or morpholinyl;

$R^8$ is selected in the group consisting of H, halogen, cyano, $(C_1-C_6)$alkyl, aryl, heteroaryl, —SO—$R^9$, —$SO_2$—$R^9$, $(C_1-C_6)$alkyl-$SO_2$—$R^9$, —$NO_2$, —$N(R^9)_2$, $(C_1-C_6)$-alkyl-O—$R^9$, —$SR^9$, —$SO_2$—$R^9$, —(C=O)O—$R^9$, —(C=O)—$R^9$, —(C=O)N(R^9)_2$, —(C=O)NH—$R^9$, —(C=O)NR^9$—N(R^9)_2$, —$NR^9$—(C=O)—N(R^9)_2$, —$NR^9$—(SO_2$—$R^9$), —NH—(C=O)—$R^9$, $(C_1-C_6)$-alkyl-NH—(C=O)—$R^9$, —$NR^9$—(C=O)—$R^9$ wherein $R^9$ is selected from the group consisting of H, $C_3-C_8$ cycloalkyl, 3-8 membered heterocycloalkyl which may contain 1-2 further heteroatoms selected from O, N or S, $(C_1-C_6)$-alkyl-heterocycloalkyl wherein said heterocycloalkyl may contain 1-2further heteroatoms selected from O, N or S, aryl, $(C_1-C_6)$-alkyl-aryl, $(C_1-C_6)$-alkoxy-aryl, heteroaryl, $(C_1-C_6)$-alkyl-heteroaryl or $(C_1-C_6)$-alkoxy-heteroaryl, $(C_1-C_6)$-alkyl, $(C_1-C_6)$-alkyl-$COOR^{10}$ wherein $R^{10}$ is H or $(C_1-C_6)$ alkyl or —$NH_2$ m' is 0 or 1;

p is an integer from 1 to 3;

with the proviso that the following compounds are excluded:

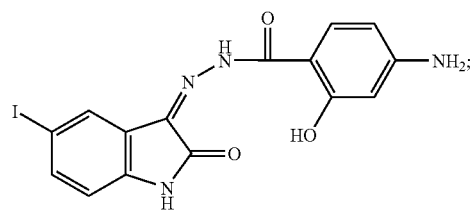

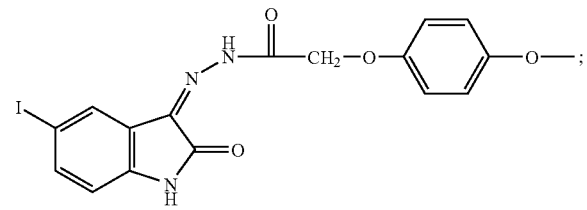

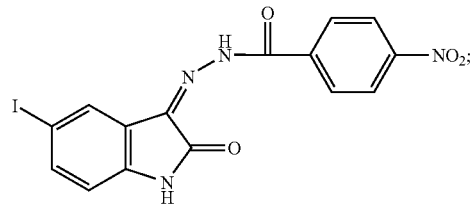

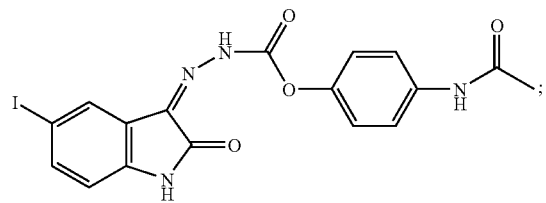

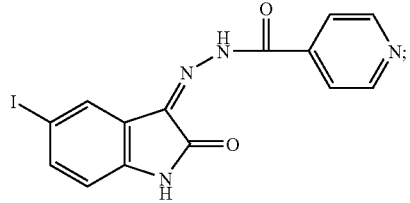

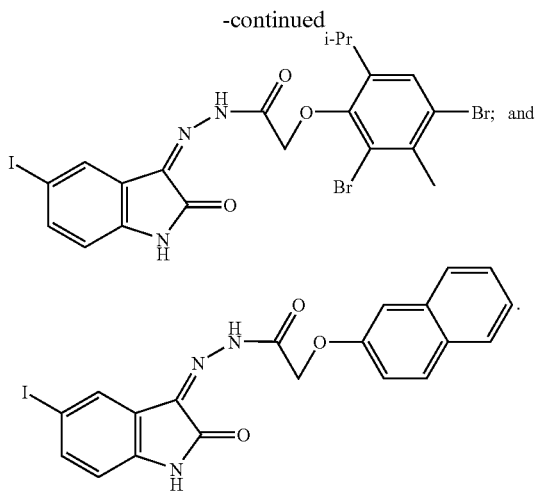

2. An oxindole hydrazide according to claim 1, wherein B is a phenyl group and m' is 0.

3. An oxindole hydrazide according to claim 2 wherein m' is 0, p is 0 or 1, A is a bond or O, B is a phenyl group and $R^8$ is selected in the group consisting of —$O_2$, —$CO_2$—$R^9$ and —NH—(C=O)—$R^9$ wherein $R^9$ is selected from the group consisting of H, $C_3$-$C_8$ cycloalkyl, 3-8 membered heterocycloalkyl which may contain 1-2 further heteroatoms selected from O, N or S, ($C_1$-$C_6$)-alkyl-heterocycloalkyl wherein said heterocycloalkyl may contain 1-2 further heteroatoms selected from O, N or S, aryl, ($C_1$-$C_6$)-alkyl-aryl, ($C_1$-$C_6$)-alkoxy-aryl, heteroaryl, ($C_1$-$C_6$)-alkyl-heteroaryl or ($C_1$-$C_6$)-alkoxy-heteroaryl, ($C_1$-$C_6$)-alkyl, ($C_1$-$C_6$)-alkyl-$COOR^{10}$ wherein $R^{10}$ is H or ($C_1$-$C_6$)alkyl or —$NH_2$.

4. An oxindole hydrazide according to claim 1, wherein said oxindole hydrazide is selected from the group consisting of:

N-(4-{[2-(5-Iodo-2-oxo-1,2-dihydro-3H-indol-3-ylidene)hydrazino]carbonyl}phenyl)-3-phenylpropanamide;
3,5-Dichloro-N'-(5-iodo-2-oxo-1,2-dihydro-3H-indol-3-ylidene)benzohydrazide;
N'-(5-Iodo-2-oxo-1,2-dihydro-3H-indol-3-ylidene)benzohydrazide;
N'-(5-Iodo-2-oxo-1,2-dihydro-3H-indol-3-ylidene)-4-methylbenzohydrazide;
4-Hydroxy-N'-(5-iodo-2-oxo-1,2-dihydro-3H-indol-3-ylidene)benzohydrazide;
3-Hydroxy-N'-(5-iodo-2-oxo-1,2-dihydro-3H-indol-3-ylidene)benzohydrazide;
N'-(5-Iodo-2-oxo-1,2-dihydro-3H-indol-3-ylidene)-2-nitrobenzohydrazide;
N'-(5-Iodo-2-oxo-1,2-dihydro-3H-indol-3-ylidene)-4-phenoxybenzohydrazide;
N'-(5-Iodo-2-oxo-1,2-dihydro-3H-indol-3-ylidene)-4-(trifluoromethyl) benzohydrazide;
4-tert-Butyl-N'-(5-Iodo-2-oxo-1,2-dihydro-3H-indol-3-ylidene)benzohydrazide;
N'-(5-Iodo-2-oxo-1,2-dihydro-3H-indol-3-ylidene)[1,1'-biphenyl]-4-carbohydrazide;
4-Bromo-N'-(5-iodo-2-oxo-1,2-dihydro-3H-indol-3-ylidene)benzohydrazide;
N'-(5-Iodo-2-oxo-1,2-dihydro-3H-indol-3-ylidene)-3-nitrobenzohydrazide;
N'-(5-Iodo-2-oxo-1,2-dihydro-3H-indol-3-ylidene)-4-methoxybenzohydrazide;
N'-(5-Iodo-2-oxo-1,2-dihydro-3H-indol-3-ylidene)-3-methoxybenzohydrazide;
4-Amino-N'-(5-iodo-2-oxo-1,2-dihydro-3H-indol-3-ylidene)benzohydrazide;
4-(Dimethylamino)-N'-(5-iodo-2-oxo-1,2-dihydro-3H-indol-3-lidene)benzohydrazide;
N'-(5-Iodo-2-oxo-1,2-dihydro-3H-indol-3-ylidene)-2-(4-nitrophenoxy) acetohydrazide;
N'-(5-Iodo-2-oxo-1,2-dihydro-3H-indol-3-ylidene)-4-(trifluoromethoxy) benzohydrazide;
N'-(5-Iodo-2-oxo-1,2-dihydro-3H-indol-3-ylidene)-2,1,3-benzoxadiazole-5-carbohydrazide;
N'-(5-Iodo-2-oxo-1,2-dihydro-3H-indol-3-ylidene)-((5-nitro)-2-furohydrazide);
Methyl 4-{[2-(5-iodo-2-oxo-1,2-dihydro-3H-indol-3-ylidene)hydrazino]carbonyl}benzoate;
Methyl 4-{2-[2-(5-iodo-2-oxo-1,2-dihydro-3H-indol-3-ylidene)hydrazino]-2-oxoethoxy}benzoate;
4-{[2-(5-Iodo-2-oxo-1,2-dihydro-3H-indol-3-ylidene)hydrazino]carbonyl}benzoic acid;
4-Iodo-N'-(5-Iodo-2-oxo-1,2-dihydro-3H-indol-3-ylidene)benzohydrazide;
N'-(5-Iodo-2-oxo-1,2-dihydro-3H-indol-3-ylidene)-3-phenoxybenzohydrazide;
N'-(5-Iodo-2-oxo-1,2-dihydro-3H-indol-3-ylidene)-2-(4-iodophenoxy)acetohydrazide;
N'-(5-Iodo-2-oxo-1,2-dihydro-3H-indol-3-ylidene)-2-[(4-methylphenyl) sulfonyl]acetohydrazide;
2-{[(2-Furylmethyl)sulfonyl]methyl}-N'-(5-iodo-2-oxo-1,2-dihydro-3H-indol-3-ylidene)-1,3-thiazole-4-carbohydrazide;
2-Hydroxy-N'-(-5-iodo-2-oxo-1,2-dihydro-3H-indol-3-ylidene)benzohydrazide;
N-(2-Furylmethyl)-N'-{2-[2-(5-iodo-2-oxo-1,2-dihydro-3H-indol-3-ylidene) hydrazino]-2-oxoethyl}urea;
N'-(5-Iodo-2-oxo-1,2-dihydro-3H-indol-3-ylidene)-4-(methylsulfanyl) benzohydrazide;
Methyl 6-{[2-(5-iodo-2-oxo-1,2-dihydro-3H-indol-3-ylidene) hydrazino]carbonyl}nicotinate;
Benzyl 4-{2-[2-(5-iodo-2-oxo-1,2-dihydro-3H-indol-3-ylidene)hydrazine]-2-oxoethoxy}benzoate;
N-(4-{[2-(5-Iodo-2-oxo-1,2-dihydro-3H-indol-3-ylidene) hydrazino]carbonyl}phenyl)-2-furamide;
N-(4-{[2-(5-Iodo-2-oxo-1,2-dihydro-3H-indol-3-ylidene) hydrazino]carbonyl}phenyl)hexanamide;
4-Cyano-N-(4-{[2-(5-iodo-2-oxo-1,2-dihydro-3H-indol-3-ylidene)hydrazino]carbonyl}phenyl)benzamide;
4-(Hexyloxy)-N-(4-{[2-(5-iodo-2-oxo-1,2-dihydro-3H-indol-3-ylidene)hydrazino]carbonyl}phenyl)benzamide;
4-Heptyl-N-(4-{[2-(5-iodo-2-oxo-1,2-dihydro-3H-indol-3-ylidene)hydrazino]carbonyl}phenyl)benzamide;
2-{2-Nitro-4,5-dimethoxyphenyl}-N'-[5-iodo-2-oxo-1,2-dihydro-3H-indol-3-yliden)acetohydrazide;
N'-(5-Iodo-2-oxo-1,2-dihydro-3H-indol-3-ylidene)-1-(3-pyridinylmethyl)-4-piperidinecarbohydrazide;
2-Amino-5-nitro-N'-(5-iodo-2-oxo-1,2-dihydro-3H-indol-3-ylidene)benzohydrazide;
2-[5-(3-Nitrophenyl)-2H-tetrazol-2-yl]-N'-(5-iodo-2-oxo 1,2-dihydro-3H-indol-3-ylidene)acetohydrazide;
N'-(5-Iodo-2-oxo-1,2-dihydro-3H-indol-3-ylidene)-2-[5-(1-pyrrolidinyl)-2H-tetrazol-2-yl]acetohydrazide;
N'-(5-Iodo-2-oxo-1,2-dihydro-3H-indol-3-ylidene)-2-[5-(4-morpholinyl)-2H-tetrazol-2-yl]acetohydrazide;
4-{2-[2-(5-Iodo-2-oxo-1,2-dihydro-3H-indol-3-ylidene) hydrazino]-2-oxoethoxy}benzoic acid;

4-{[2-(5-Iodo-2-oxo-1,2-dihydro-3H-indol-3-ylidene)hydrazino]carbonyl}-N-phenylbenzamide;
4-Cyano-N-(3-{[2-(5-iodo-2-oxo-1,2-dihydro-3H-indol-3-ylidene) hydrazino]carbonyl}phenyl)benzamide;
N'-[5-Iodo-2-oxo-1,2-dihydro-3H-indol-3-ylidene]-4-[4-(4-morpholinylmethyl) phenoxy]benzohydrazide;
N-(4-{[2-(5-Iodo-2-oxo-1,2-dihydro-3H-indol-3-ylidene) hydrazino]carbonyl}phenyl) benzamide;
4-(Benzyloxy)-N'-(5-iodo-2-oxo-1,2-dihydro-3H-indol-3-ylidene)benzohydrazide;
N-(3-{[2-(5-Iodo-2-oxo-1,2-dihydro-3H-indol-3-ylidene) hydrazino]carbonyl}phenyl)-3-phenyipropanamide;
4-{[2-(5-Iodo-2-oxo-1,2-dihydro-3H-indol-3-ylidene)hydrazino]carbonyl}-N-{3-[(trifluoromethyl)sulfonyl] phenyl}benzamide;
4-Chloro-N-(4-{[2-(5-iodo-2-oxo-1,2-dihydro-3H-indol-3-ylidene)hydrazino]-carbonyl }benzyl)benzamide;
Methyl 4-{3-[2-(5-iodo-2-oxo-1,2-dihydro-3H-indol-3-ylidene)hydrazino]-3-oxopropyl }benzoate;
2-[(2-Chlorophenoxy)methyl]-N'-(5-iodo-2-oxo-1,2-dihydro-3H-indol-3-ylidene)-1,3-thiazole-4-carbohydrazide;
N'-(5-Iodo-2-oxo-1,2-dihydro-3H-indol-3-ylidene)-2-(2-phenyl[1,3]thiazolo[3,2-b][1,2,4]triazol-6-yl)acetohydrazide;
4-{[3-Chloro-5-(trifluoromethyl)-2-pyridinyl]amino}-N'-[5-iodo-2-oxo-1,2-dihydro-3H-indol-3-ylidene]butanohydrazide;
2-{[3-Chloro-5-(trifluoromethyl)-2-pyridinyl]amino}-N'-(5-iodo-2-oxo-1,2-dihydro-3H-indol-3-ylidene)acetohydrazide;
1-Benzoyl-N'-(5-iodo-2-oxo-1,2-dihydro-3H-indol-3-ylidene)-4-piperidinecarbohydrazide;
N-(4-{[2-(5-Iodo-2-oxo-1,2-dihydro-3H-indol-3-ylidene) hydrazino]carbonyl}phenyl)-2-phenoxyacetamide;
N-(4-{[2-(5-Iodo-2-oxo-1,2-dihydro-3H-indol-3-ylidene)hydrazino]carbonyl}phenyl)-nicotinamide;
3-Nitro-N-(4-{[2-(5-iodo-2-oxo-1,2-dihydro-3H-indol-3-ylidene) hydrazino]carbonyl}-benzyl)benzamide;
N-(4-{[2-(5-Iodo-2-oxo-1,2-dihydro-3H-indol-3-ylidene) hydrazino]carbonyl}-phenyl)[1,1'-biphenyl]-4-carboxamide;
Methyl-3-{2-[2-(5-iodo-2-oxo-1,2-dihydro-3H-indol-3-ylidene)hydrazino]-2-oxoethoxy }benzoate;
Methyl-4-{[[2-(5-iodo-2-oxo-1,2-dihydro-3H-indol-3-ylidene)hydrazino](oxo)acetyl]-amino }benzoate;
3-(1,3-Benzodioxol-5-yl)-N-(4-{[2-(5-iodo-2-oxo-1,2-dihydro-3H-indol-3-ylidene)-hydrazine]carbonyl} phenyl)propanamide;
4-[(4-{[2-(5-Iodo-2-oxo-1,2-dihydro-3H-indol-3-ylidene)hydrazino]carbonyl}benzoyl)-amino]benzoic acid;
3-(3,4-Dihydroxyphenyl)-N-(4-{[2-(5-iodo-2-oxo-1,2-dihydro-3H-indol-3-ylidene)hydrazino]carbonyl} phenyl)propanamide;
3-(3-Hydroxyphenyl)-N-(4-{[2-(5-iodo-2-oxo-1,2-dihydro-3H-indol-3-ylidene)hydrazino]-carbonyl}phenyl) propanamide;
N'-(5-Iodo-2-oxo-1,2-dihydro-3H-indol-3-ylidene)-6-methoxy-5-nitronicotinohydrazide;
3-{[2-(5-Iodo-2-oxo-1,2-dihydro-3H-indol-3-ylidene)hydrazino]sulfonyl}benzoic acid;
2-Hydroxy-5-{[2-(5-iodo-2-oxo-1,2-dihydro-3H-indol-3-ylidene) hydrazino]sulfonyl}-benzoic acid;
N'-(5-Iodo-2-oxo-1,2-dihydro-3H-indol-3-ylidene)-5-(2-pyridinyl)-2-thiophenesulfono-hydrazide;
4-Chloro-N'-(5-iodo-2-oxo-1,2-dihydro-3H-indol-3-ylidene)-3-nitrobenzenesulfono-hydrazide;
Methyl-{3-[(4-hydroxybenzoyl)hydrazono]-5-iodo-2-oxo-2,3-dihydro-1H-indol-1-yl}acetate;
N-Dodecyl-3-[(4-hydroxybenzoyl)hydrazono]-5-iodo-2-oxo-2,3-dihydro-1H-indole-1-carboxamide;
Methyl-(3-{[4-(hexanoylamino)benzoyl]hydrazono}-5-iodo-2-oxo-2,3-dihydro-1H-indol-1-yl)acetate;
(3-{[4-(hexanoylamino)benzoyl]hydrazono}-5-iodo-2-oxo-2,3-dihydro-1H-indol-1-yl) acetic acid;
(3-{[4-(hexanoylamino)benzoyl]hydrazono}-5-iodo-2-oxo-2,3-dihydro-1H-indol-1-yl) acetic acid, tromethanine (2-amino-2-hydroxymethyl-1,3-propanediol) salt;
(3-{[4-(hexanoylamino)benzoyl]hydrazono}-5-iodo-2-oxo-2,3-dihydro-1H-indol-1-yl) acetic acid, N-methyl-D-glucamine (1-deoxy-1-(methylamino)glucitol) salt;
2-(4-cyanophenoxy)-N'-(5-iodo-2-oxo-1,2-dihydro-3H-indol-3-ylidene) acetohydrazide;
4-({2-[2-(5-iodo-2-oxo-1,2-dihydro-3H-indol-3-ylidene) hydrazino]-2-oxoethyl}thio)-3-nitrobenzenesulfonamide;
N-(4-{[2-(5-iodo-2-oxo-1,2-dihydro-3H-indol-3-ylidene) hydrazino]carbonyl}phenyl)-N-methyl-3-phenyipropanamide;
methyl-{3-[(4-{[3-(1,3-benzodioxol-5-yl)propanoyl] amino}benzoyl)hydrazono]-5-iodo-2-oxo-2,3-dihydro-1H-indol-1-yl}acetate;
methyl-4-[(4-{[2-(5-iodo-2-oxo-1,2-dihydro-3H-indol-3-ylidene)hydrazino]carbonyl}-phenyl)amino]-4-oxobutanoate;
3-(1,3-benzodioxol-5-yl)-N-(4-{[2-(5-bromo-2-oxo-1,2-dihydro-3H-indol-3-ylidene)-hydrazine]carbonyl} phenyl)propanamide;
{3-[(4-{[3-(1,3-benzodioxol-5-yl)propanoyl] amino}benzoyl)hydrazono]-5-iodo-2-oxo-2,3-dihydro-1H-indol-1-yl}acetic acid;
{3-[(4-{[3-(1,3-benzodioxol-5-yl)propanoyl] amino}benzoyl)hydrazono]-5-iodo-2-oxo-2,3-dihydro-1H-indol-1-yl}acetic acid, N-methyl-D-glucamine (1-deoxy-1-(methylamino) glucitol)salt;
methyl-6-[(4-{[2-(5-iodo-2-oxo-1,2-dihydro-3H-indol-3-ylidene)hydrazino]carbonyl}-phenyl)amino]-6-oxohexanoate;
methyl-4-{[(4-{[2-(5-iodo-2-oxo-1,2-dihydro-3H-indol-3-ylidene)hydrazino]carbonyl}-phenyl)amino] carbonyl}benzoate;
methyl-8-[(4-{[2-(5-iodo-2-oxo-1,2-dihydro-3H-indol-3-ylidene) hydrazino]carbonyl}-phenyl)amino]-8-oxooctanoate;
methyl-5-[(4-{[2-(5-iodo-2-oxo-1,2-dihydro-3H-indol-3-ylidene) hydrazino]carbonyl}-phenyl)amino]-5-oxopentanoate;
8-[(4-{[2-(5-iodo-2-oxo-1,2-dihydro-3H-indol-3-ylidene) hydrazino]carbonyl}phenyl)-amino]-8-oxooctanoic acid;
8-[(4-{[2-(5-iodo-2-oxo-1,2-dihydro-3H-indol-3-ylidene) hydrazino]carbonyl}phenyl)-amino]-8-oxooctanoic acid, N-methyl-D-glucamine (1-deoxy-1-(methylamino)glucitol) salt;
6-[(4-{[2-(5-iodo-2-oxo-1,2-dihydro-3H-indol-3-ylidene) hydrazino]carbonyl}phenyl)-amino]-6-oxohexanoic acid;
6-[(4-{[2-(5-iodo-2-oxo-1,2-dihydro-3H-indol-3-ylidene) hydrazino]carbonyl}phenyl)-amino]-6-oxohexanoic acid, N-methyl-D-glucamine (1-deoxy-1-(methylamino)glucitol) salt;

4-[(4-{[2-(5-iodo-2-oxo-1,2-dihydro-3H-indol-3-ylidene)hydrazino]carbonyl}phenyl)-amino]-4oxobutanoic acid;

4-{[(4-{[2-(5-iodo-2-oxo-1,2-dihydro-3H-indol-3-ylidene)hydrazine]carbonyl}benzyl)-amino]carbonyl}benzoic acid, N-methyl-D-glucamine (1-deoxy-1-(methylamino)-glucitol) salt;

5-[(4-{[(2-(5-iodo-2-oxo-1,2-dihydro-3H-indol-3-ylidene)hydrazino]carbonyl}phenyl)-amino]-5-oxopentanoic acid;

5-[(4-{[(2-(5-iodo-2-oxo-1,2-dihydro-3H-indol-3-ylidene) hydrazino]carbonyl}phenyl)-amino]-5-oxopentanoic acid, N-methyl-D-glucamine (1-deoxy-1-(methylamino)glucitol) salt;

4-{[(4-{[2-(5-iodo-2-oxo-1,2-dihydro-3H-indol-3-ylidene)hydrazino]carbonyl}phenyl)-amino]carbonyl}benzoic acid;

4-{[(4-{[2-(5-iodo-2-oxo-1,2-dihydro-3H-indol-3-ylidene) hydrazino]carbonyl}phenyl)-amino]carbonyl}benzoic acid, N-methyl-D-giucamine (1-deoxy-1-(methylamino)-glucitol) salt;

methyl-4-{[(4-{[2-(5-iodo-2-oxo-1,2-dihydro-3H-indol-3-ylidene) hydrazino]carbonyl}-benzyl)amino]carbonyl}benzoate;

4-{[(4-{[2-(5-iodo-2-oxo-1,2-dihydro-3H-indol-3-ylidene) hydrazino]carbonyl}benzyl)-amino]carbonyl}benzoic acid;

4-{[(4-{[2-(5-iodo-2-oxo-1,2-dihydro-3H-indol-3-ylidene)hydrazine]carbonyl}benzyl)-amino]carbonyl}benzoic acid, N-methyl-D-glucamine (1-deoxy-1-(methylamino)-glucitol) salt;

benzyl-(2S)-2-(4-{[2-(5-iodo-2-oxo-1,2-dihydro-3H-indol-3-ylidene)hydrazino]-carbonyl}phenoxy)-3-phenylpropanoate;

(2S)-2-(4-{[2-(5-iodo-2-oxo-1,2-dihydro-3H-indol-3-ylidene)hydrazino]carbonyl}-phenoxy)-3-phenyipropanoic acid;

(2S)-2-(4-{[2-(5-iodo-2-oxo-1,2-dihydro-3H-indol-3-ylidene)hydrazino]carbonyl}-phenoxy)-3-phenyipropanoic acid, N-methyl-D-glucamine (1-deoxy-1-(methylamino) glucitol) salt;

methyl-4-{3-[(4-{[3-(1,3-benzodioxol-5-yl)propanoyl]amino}benzoyl)hydrazonoll-5-iodo-2-oxo-2,3-dihydro-1H-indol-1-yl}butanoate;

4-{3-[(4-{[3-(1,3-benzodioxol-5-yl)propanoyl]amino}benzoyl)hydrazono]-5-odo-2-oxo-2,3-dihydro-1H-indol-1-yl}butanoic acid;

4-{3-[(4-{[3-(1,3-benzodioxol-5-yl)propanoyl]amino}benzoyl)hydrazono]-5-iodo-2-oxo-2,3-dihydro-1H-indol-1-yl}butanoic acid, N-methyl-D-glucamine (1-deoxy-1-(methylamino)glucitol) salt;

methyl-3-(4-{[(4-{[2-(5-iodo-2-oxo-1,2-dihydro-3H-indol-3-ylidene)hydrazino]-carbonyl}phenyl)amino]sulfonyl}phenyl)propanoate;

3-(4-{[(4-{[2-(5-iodo-2-oxo-1,2-dihydro-3H-indol-3-ylidene)hydrazino]carbonyl}-phenyl)amino]sulfonyl}phenyl) propanoic acid; and 3-(4-{[(4-{[2-(5-iodo-2-oxo-1,2-dihydro-3H-indol-3-ylidene)hydrazino]carbonyl}-phenyl)amino]sulfonyl}phenyl) propanoic acid, N-methyl-D-glucamine (1-deoxy-1-(methylamino) glucitol) salt.

5. An oxindole hydrazide selected from the group consisting of:

4-Nitro-N'-(5-bromo-2-oxo-1,2-dihydro-3H-indol-3-ylidene)benzohydrazide;

Methyl-4-{2-[2-(5-bromo-2-oxo-1,2-dihydro-3H-indol-3-ylidene)hydrazino]-2-oxoethoxy}benzoate;

4-Methoxy-N'-(5-bromo-2-oxo-1,2-dihydro-3H-indol-3-ylidene)benzohydrazide;

N-(4-{[2-(5-Bromo-2-oxo-1,2-dihydro-3H-indol-3-ylidene)hydrazino]carbonyl}phenyl)-3-phenylpropanamide;

N'-(5-Bromo-2-oxo-1,2-dihydro-3H-indol-3-ylidene)-4-{3-[2-(5-bromo-2-oxo-1,2-dihydro-3H-indol-3-ylidene)hydrazino]-3-oxopropyl}benzohydrazide;

N-(4-{[2-(5-Bromo-2-oxo-1,2-dihydro-3H-indol-3-ylidene)hydrazino]carbonyl}-phenyl)-2-phenoxyacetamide;

N-(4-{[2-(5-Bromo-2-oxo-1,2-dihydro-3H-indol-3-ylidene)hydrazino]carbonyl}-benzyl)-3-nitrobenzamide;

Methyl 3-{2-[2-(5-bromo-2-oxo-1,2-dihydro-3H-indol-3-ylidene)hydrazino]-2-oxoethoxy}benzoate;

N'-(5-Bromo-2-oxo-1,2-dihydro-3H-indol-3-ylidene)-2-[4-(1H-tetrazol-5-yl)phenoxy]acetohydrazide; and N'-(5-Bromo-2-oxo-1,2-dihydro-3H-indol-3-ylidene)-4-(1H-tetrazol-5-yl)benzohydrazide.

6. An oxindole hydrazide of formula (II):

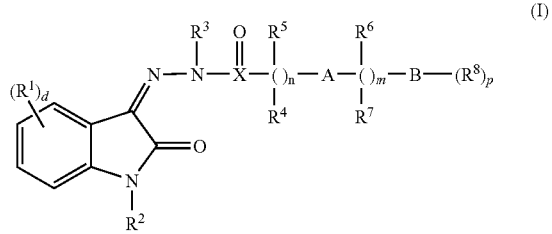

wherein A is O or a bond;

wherein B is selected from the group consisting of phenyl, biphenyl, benzo (1,2,5) oxadiazolyl, furyl, thiadiazolyl, thienyl, thiazolyl, indolyl, piperidinyl, tetrazolyl, 1,2,3-triazolyl, 1,2,4-triazolyl and pyridyl;

$R^8$ is selected in the group consisting of H, halogen, cyano, $(C_1-C_6)$alkyl, aryl, heteroaryl, —SO—$R^9$, —SO$_2$—$R^9$, $(C_1-C_6)$alkyl-SO$_2$—$R^9$, —NO$_2$, —N$(R^9)_2$, $(C_1-C_6)$-alkyl-O—$R^9$, —SR$^9$, —SO$_2$—$R^9$, —(C=O)O—$R^9$, —(C=O)—$R^9$, —(C=O)N$(R^9)_2$, —(C=O)NH—$R^2$, —(C=O)NR$^9$—N$(R^9)_2$, —NR$^9$—(C=O)—N$(R^9)_2$, —NR$^9$—(SO$_2$—$R^9$), —NH—(C=O)—$R^9$, $(C_1-C_6)$-alkyl-NH—(C=O)-$R^9$, —NR$^9$—(C=O)—$R^9$ wherein $R^9$ is selected from the group consisting of H, $C_3-C_8$ cycloalkyl, 3-8 membered heterocycloalkyl which may contain 1-2 further heteroatoms selected from O, N or S, $(C_1-C_6)$-alkyl-heterocycloalkyl wherein said heterocycloalkyl may contain 1-2 further heteroatoms selected from O, N or S, aryl, $(C_1-C_6)$-alkyl-aryl, $(C_1-C_6)$-alkoxy-aryl, heteroaryl, $(C_1-C_6)$-alkyl-heteroaryl or $(C_1-C_6)$-alkoxy-heteroaryl, $(C_1-C_6)$-alkyl, $(C_1-C_6)$-alkyl-COOR$^{10}$ wherein $R^{10}$ is H or $(C_1-C_6)$ alkyl or —NH$_2$ m' is 0 or 1;

p is an integer from 1 to 3;

with the proviso that the following compounds are excluded:

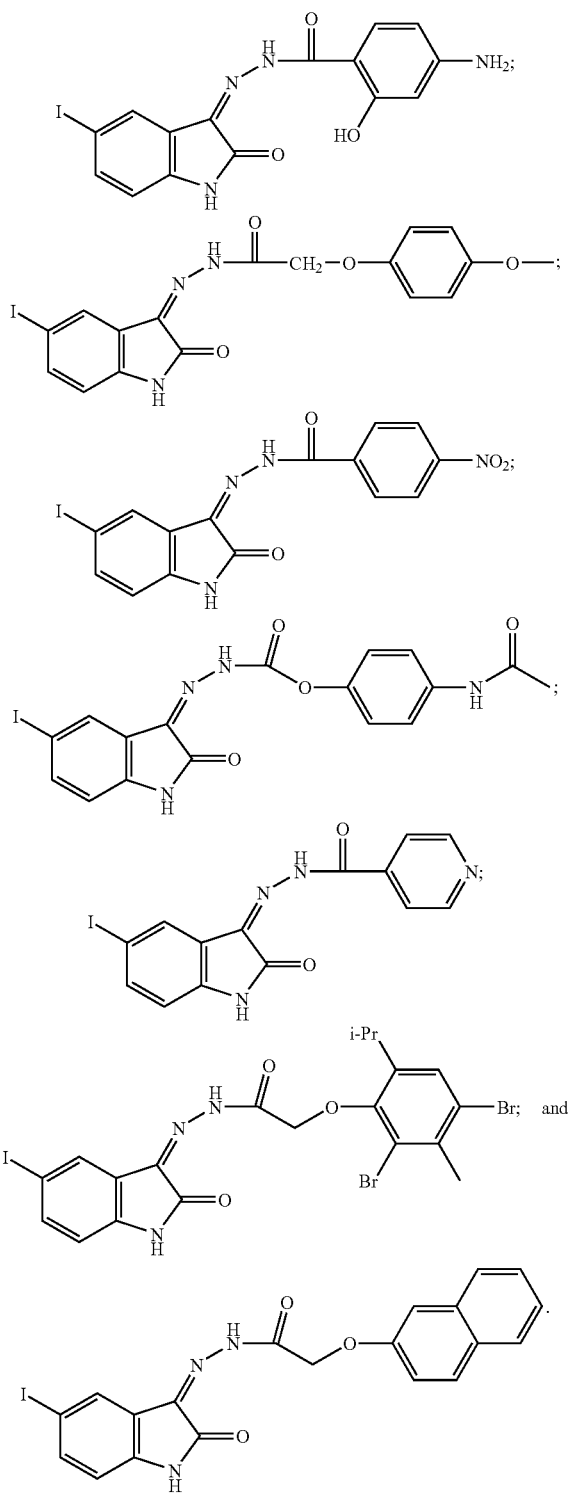

7. A pharmaceutical composition comprising at least one oxindole hydrazide according to claim 1, and a pharmaceutically acceptable carrier, diluent or excipient thereof.

8. A method of preparing an oxindole of formula (I) according to claim 1, which comprises:

reacting A and B as follows:

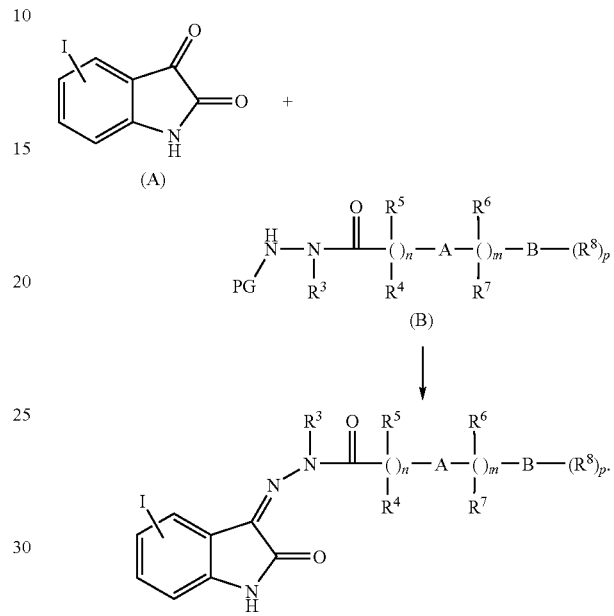

9. A method according to claim 8, wherein compound B is prepared by a process, which comprises:

reacting (C) with PG-NH—NH—$R^3$ as follows:

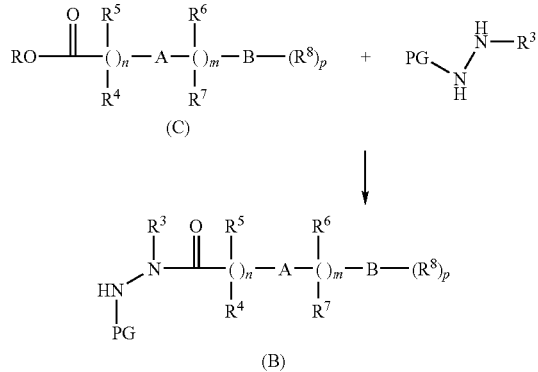

wherein R is $C_1$-$C_6$ alkyl group and PG, R, A, B, $R^8$ m, n and p are as above defined.

* * * * *